United States Patent
Schwob et al.

(10) Patent No.: US 9,080,172 B2
(45) Date of Patent: Jul. 14, 2015

(54) TARGETING P63 TO RE-ACTIVATE DORMANT RESERVE STEM CELLS IN OLFACTORY EPITHELIUM

(75) Inventors: James E. Schwob, West Roxbury, MA (US); Nikolai Schnittke, Brooklyn, NY (US); Adam I. Packard, Bronx, NY (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 14/122,024

(22) PCT Filed: May 25, 2012

(86) PCT No.: PCT/US2012/039688
§ 371 (c)(1),
(2), (4) Date: Apr. 14, 2014

(87) PCT Pub. No.: WO2012/166646
PCT Pub. Date: Dec. 6, 2012

(65) Prior Publication Data
US 2014/0221456 A1  Aug. 7, 2014

Related U.S. Application Data

(60) Provisional application No. 61/491,099, filed on May 27, 2011, provisional application No. 61/493,243, filed on Jun. 3, 2011.

(51) Int. Cl.
*C12Q 1/68* (2006.01)
*C12N 15/113* (2010.01)
*C12N 5/0793* (2010.01)
*A61K 35/36* (2015.01)

(52) U.S. Cl.
CPC .............. *C12N 15/113* (2013.01); *C12N 5/062* (2013.01); *A61K 35/36* (2013.01); *C12N 2501/40* (2013.01); *C12N 2501/998* (2013.01)

(58) Field of Classification Search
None
See application file for complete search history.

(56) References Cited

U.S. PATENT DOCUMENTS 7,294,459 B1  11/2007  Yang et al.

FOREIGN PATENT DOCUMENTS

WO  2010/039679 A1  8/2010

OTHER PUBLICATIONS

Chen et al., J Comp Neurol, 2004. http://www.ncbi.nlm.nih.gov/pubmed/14755529. "Multipotency of purified, transplanted globose basal cells in olfactory epithelium." Abstract only.

Iwai et al., Stem Cells, 2008. http://www.ncbi.nlm.nih.gov/pubmed/18308944. "Horizontal basal cells are multipotent progenitors in normal and injured adult olfactory epithelium." Abstract only.
Leung et al., Nat Neurosci, 10(6):720-6 (2007). "Contribution of olfactory neural stem cells to tissue maintenance and regeneration." Abstract only.
Packard et al., J Neurosci, 31(24):8748-8759 (2011). "DeltaNp63 regulates stem cell dynamics in the mammalian olfactory epithelium." Abstract only.
Packard et al., "ΔNp63 regulates stem cell dynamics in the mammalian olfactory epithelium", J. Neurosci, 31(24):8748-8759, (2011).
Packard et al., "The progenitor cell capacity of NeuroD1-expressing globose basal cells in the mouse olfactory epithelium" J. Comp. Neurol., 519(17): 3580-3596, (2011).
Pelligrini et al. "p63 identifies keratinocyte stem cells", Proc. Natl. Acad. Sci. U S A 98:3156-3161 (2001).
Rock et al., "Airway basal stem cells: a perspective on their roles in epithelial homeostasis and remodeling", Dis Model Mech 3:545-556 (2010).
Rodriguez-Gil et al., "Wnt/Frizzled family members mediate olfactory sensory neuron axon extension", J Comp Neurol 511:301-317 (2008).
Romano et al., "Defining the regulatory elements in the proximal promoter of DeltaNp63 in keratinocytes: Potential roles for Sp1/Sp3, NF-Y, and p63", J Invest Dermatol 126:1469-1479 (2006).
Romano et al., "An active role of the DeltaN isoform of p63 in regulating basal keratin genes K5 and K14 and directing epidermal cell fate", PLoS One, 4:e5623 (2009).
Schwob et al., Olfactory sensory neurons are trophically dependent on the olfactory bulb for their prolonged survival. J Neurosci 12:3896-3919. (1992).
Schwob et al., On the formation of neuromata in the primary olfactory projection. J. Comp. Neurol., 340:361-380. (1994).
Schwob et al., "Reconstitution of the rat olfactory epithelium after methyl bromide-induced lesion", J. Comp. Neurol., 359:15-37. (1995).
Shah et al., Wnt and Notch Pathways have Interrelated Opposing Roles on Prostate Progenitor Cell Proliferation and Differentiation. Stem Cells, 29(4): 678-688, (2011).
Signoretti et al., "p63 is a prostate basal cell marker and is required for prostate development", Am J Pathol., 157:1769-1775 (2000).
Snippert et al., "Intestinal crypt homeostasis results from neutral competition between symmetrically dividing Lgr5 stem cells", Cell, 143:134-144 (2010).

(Continued)

*Primary Examiner* — Kimberly Chong
(74) *Attorney, Agent, or Firm* — Nixon Peabody LLP; David S. Resnick

(57) ABSTRACT

Disclosed herein is a method for activating a dormant epithelial stem cell, or population thereof, to a state of multipotency comprising, reducing the level of ΔNp63 in the cell(s). The dormant epithelial stem cell(s) may be a horizontal basal cell (HBC) of the olfactory epithelium and the level of ΔNp63 may be reduced by contacting the cell or population with an effective amount of one or more agents that downmodulate ΔNp63. One example of an agent is an RNAi. Also disclosed is a method for treating olfactory dysfunction in a subject, comprising activating HBCs of the subject by reducing the level of ΔNp63 in one or more HBCs of the subject, to thereby treat the olfactory dysfunction. Activated horizontal basal cell (HBCs) are also disclosed.

4 Claims, 18 Drawing Sheets

(56) References Cited

OTHER PUBLICATIONS

Thepot et al., Intraepithelial p63-dependent expression of distinct components of cell adhesion complexes in normal esophageal mucosa and squamous cell carcinoma. Int J Cancer. 127: 2051-2062, (2010).
Truong et al., "p63 regulates proliferation and differentiation of developmentally mature keratinocytes", Genes & Dev., 20: 3185-3197 (2006).
Truong et al., "Control of keratinocyte proliferation and differentiation by p63", Cell Cycle 6:295-299 (2007).
Wang et al., "Activation of the Wnt/beta-catenin signaling reporter in developing mouse olfactory nerve layer marks a specialized subgroup of olfactory ensheathing cells", Dev Dyn., 237:3157-3168 (2008).
Wang et al., "Canonical Wnt signaling promotes proliferation and neurogenesis of peripheral olfactory stem cells/progenitors during postnatal development and adult regeneration", J Cell Sci 124: 1553-1556 (2011).
Weinmaster et al., "A garden of Notch-ly delights", Development, 133:3277-3282 (2006).
Wildner et al., "dILA neurons in the dorsal spinal cord are the product of terminal and non-terminal asymmetric progenitor cell divisions, and require Mash1 for their development", Development,133:2105-2113 (2006).
Yalcin-Ozuysal et al., "Antagonistic roles of Notch and p63 in controlling mammary epithelial cell fates", Cell Death Differentiation. 17:1600-1612 (2010).
Yang et al., "Relationships between p63 binding, DNA sequence, transcription activity, and biological function in human cells", Mol Cell 24:593-602, (2006).
Yang et al., "ΔNp63 versatilely regulates a Broad NF-κB gene program and promotes squamous epithelial proliferation, migration, and inflammation," Cancer Res., 71(10):3688-3700, (2011).
Yang et al., "p63, p53 homolog at 3q27-29, encodes multiple products with transactivating death-inducing, and dominant-negative activities", Molecular Cell, 2(3):305-316, (1998).
Yang et al., "p63 is essential for regenerative proliferation in limb, craniofacial and epithelial development" Nature 398:714-718 (1999).
Yi et al., "A skin microRNA promotes differentiation by repressing 'stemness'", Nature 452: 225-9 (2008).
Yuan et al., "MicroRNA-203 inhibits cell proliferation by repressing ΔNp63 expression in human esophageal squamous cell carcinoma", BMC Cancer, 11:57, (2011).
Osada et al., "Cloning and functional analysis of human p51, which structurally and functioonally resembles p53", Nat. Med. 4 (7): 839-43 (1998).
Capel et al., "Heterogeneity of Human IgG Fc Receptors." Immunomethods. 4: 25-34 (1994).
Doty, A review of olfactory dysfunctions in Man. Am J Otolaryngology. 1(1): 57-79 (1979).
Krolewski et al., "Ascl1 (Mash1) Knockout perturbs differentiation of nonneuronal cells in Olfactory Epithelium." PLOS one. 7(12): e51737 (2012).
Leopold et al., "Congenital lack of olfactory ability." Ann Otol Rhinol Laryngol. 101: 229-236 (1992).
Naessen. "An enquiry on the morphological characteristics and possible changes with age in the olfactory region of man." Acta Otolaryngol. 71: 49-62 (1971).
Schwob et al., "Histopathology of olfactory mucosa in Kallmann's syndrome." Ann Otol Rhinol Laryngol. 102: 117-122 (1993).
Alonso et al., "Stem cells of the skin epithelium", Proc Natl Acad Sci U S A 100 Suppl 1, 11830-11835 (2003).
Alvarez-Buylla et al. "A unified hypothesis on the lineage of neural stem cells", Nat Rev Neurosci 2: 287-293 (2001).
Artavanis-Tsakona et al., "Notch Signaling: Cell fate control and signal integration in development", Science 284, 770-776 (1999).
Bagga et al. "Regulation by let-7 and lin-4 miRNAs results in target mRNA degradation", Cell, 122(4):553-63. (2005).
Barbieri et al., "IGFBP-3 is a direct target of transcriptional regulation by ΔNp63a in Squamous epithelium", Cancer Res 65:2314-2320 (2005).
Barker et al., "Tissue-resident adult stem cell populations of rapidly self-renewing organs." Cell Stem Cell 7:656-670 (2010).
Booker et al., "A unique cell population in the mouse olfactory bulb displays nuclear beta-catenin signaling during development and olfactory sensory neuron regeneration", Dev Neurobiol, 68:859-869 (2008).
Bray et al., "Notch signalling: a simple pathway becomes complex", Nat Rev Mol Cell Biol 7:678-689 (2006).
Caggiano et al., "Globose Basal Cells are neuronal progenitors in the olfactory epithelium: A lineage analysis using a replication-incompetent retrovirus", Neuron 13:339-352 (1994).
Calof et al., "Progenitor cells of the Olfactory Receptor Neuron Lineage", Microsc. Res. Tech. 58:176-188 (2002).
Candi et al., "Np63 regulates thymic development through enhanced expression of FgfR2 and Jag2", Proc Natl Acad Sci U S A 104:1999-12004 (2007).
Carlen et al., "Forebrain ependymal cells are Notch-dependent and generate neuroblasts and astrocytes after stroke", Nat Neurosci 12:259-267 (2009).
Carroll et al., "p63 regulates an adhesion programme and cell survival in epithelial cells", Nat Cell Biol 8:551-561, (2006).
Carter et al., Olfactory horizontal basal cells demonstrate a conserved multipotent progenitor phenotype. J Neurosci 24:5670-5683, (2004).
Cau et al., "Mash1 and Ngn1 control distinct steps of determination and differentiation in the olfactory sensory neuron lineage", Development 129:1871-1880 (2002).
Chen et al., "Multipotency of purified, transplanted globose basal cells in olfactory epithelium", J Comp Neurol 469:457-474, (2004).
Crum et al., p63 in epithelial survival, germ cell surveillance, and neoplasia:, Annu Rev Pathol Mech Dis. 5:349-371, (2010).
Delorme et al., "The human nose harbors a niche of olfactory ectomesenchymal stem cells displaying neurogenic and osteogenic properties", Stem Cells Dev 19:853-866, (2010).
Doty, "Influence of age and age-related diseases on olfactory function", Ann N Y Acad Sci., 561:76-86 (1989).
Goldstein et al., "Analysis of the globose basal cell compartment in rat olfactory epithelium using GBC-1, a new monoclonal antibody against globose basal cells", J. Neurosci., 16:4005-4016. (1996).
Goldstein et al., "Transplantation of multipotent progenitors from the adult olfactory epithelium", Neuroreport. 9:1611-1617. (1998).
Gordon et al., "Dynamics of MASH1 expression in vitro and in vivo suggest a non-stem cell site of MASH1 action in the olfactory receptor neuron lineage", Mol. Cell. Neurosci. 6:363-379 (1995).
Guo et al.,"Maintenance, Differentiation and Regulation of Multipotent Progenitor Cells in Olfactory Epithelium." Ph.D. Thesis in Cell, Molecular, and Developmental Biology (Tufts University, Boston, MA; 2008).
Hayward et al., "Wnt/Notch signalling and information processing during development", Development 135:411-424 (2008).
Holbrook et al., "Abnormalities of axon growth in human olfactory mucosa", Laryngoscope 115:2144-2154, (2005).
Huard et al., "Adult olfactory epithelium contains multipotent progenitors that give rise to neurons and non-neural cells", J. Comp. Neurol., 400:469-486 (1998).
Iwai et al., "Horizontal basal cells are multipotent progenitors in normal and injured adult olfactory epithelium", Stem Cells 26:1298-1306 (2008).
Jang et al., "Nonintegrin laminin receptor precursor protein is expressed on olfactory stem and progenitor cells", J. Comp. Neurol., 502:367-381 (2007).
Jang et al., "Maintaining epitheliopoietic potency when culturing olfactory progenitors." Exp. Neurol 214:25-36 (2008).
Jang et al., "Globose basal cells are required for reconstitution of olfactory epithelium after methyl bromide lesion", J. Comp. Neurol., 460:123-140 (2003).
Kikuchi et al., "Expression profiles and functional implications of p53-like transcription factors in thymic epithelial cell subtypes", Int Immunol 16:831-841, (2004).
Koster et al., "p63 induces key target genes required for epidermal morphogenesis", Proc Nati Acad Sci U S A 104:3255-3260, (2007).

(56) References Cited

OTHER PUBLICATIONS

Koster et al., "p63 is the molecular switch for initiation of an epithelial stratification program", Genes Dev 18:126-131 (2004).

Krolewski et al., "Expression Profiling and in Vitro Analysis fo Olfactory Epithelial Stem and Progenitor Cells", Ph. D. Thesis in Cell, Molecular and Developmental Biology (Tufts University, Boston, MA; 2010).

Krolewski et al., "The generation of olfactory epithelial neurospheres in vitro predicts engraftment." Exper NeuroIln 229(2): 308-323 (2011).

Kurita et al., "Role of p63 and basal cells in the prostate", Development, 131:4955-4964 (2004).

Largent et al., "Directed expression of an oncogene to the olfactory neuronal lineage in transgenic mice", J. Neurosci., 13:300-312. (1993).

Lena et al., "miR-203 represses 'stemness' by repressing ΔNp63", Cell Death Differentiation. 15:1187-1195, (2008).

Leung et al., "Contribution of olfactory neural stem cells to tissue maintenance and regeneration", Nat Neurosci 10:720-726, (2007).

Lim et al., "Microarray analysis shows that some microRNAs downregulate large numbers of target mRNAs", Nature, 433:769-73, (2005).

MacDonald et al., "Wnt/beta-catenin signaling: components, mechanisms, and diseases", Dev Cell 17:9-26 (2009).

Mackay-Sim et al., "Cell Dynamics in the adult mouse olfactory epithelium: A Quatitative autoradiographic study", J. Neurosci., 11:979-984 (1991).

Manglapus et al., "Expression patterns of basic helix-loop-helix transcription factors define subsets of olfactory progenitor cells", J Comp Neurol 479:216-233, (2004).

Mills et al., "p63 is a p53 homologue required for limb and epidermal morphogenesis", Nature 398:708-713 (1999).

Moran et al., "3rd Ultrastructural histopathology of human olfactory dysfunction", Microsc Res Tech 23:103-110, (1992).

Nakashima et al., "Olfactory marker protein in the human olfactory pathway", Arch Otolaryngol., 111:294-297 (1985).

Nakashima et al. "Structure of human fetal and adult olfactory neuroepithelium", Arch Otolaryngol 110:641-646 (1984).

Nguyen et al., "Cross-regulation between Notch and p63 in keratinocyte commitment to differentiation", Genes Dev 20:1028-1042, (2006).

Noszczyk et al., "p63 expression during normal cutaneous wound healing in humans", Plastic Reconstructive Surgery 108:1242-1247 (2001).

Packard, Regulation of Stem Cells and Neurogenesis in the Adult Olfactory Epithelium. Ph.D. Thesis in Cell, Molecular and Developmental Biology (Tufts University, Boston; 2010).

```
                        SEQUENCE LISTING

<160> NUMBER OF SEQ ID NOS: 6

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aacagccaug cccaguaugu a                                             21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uacauacugg gcauggcugu u                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
caaugcccag acucaauuut t                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
```

```
ttguuacggg ucugaguuaa a                                                21

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gugaaauguu uaggaccacu ag                                               22

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuaguggucc uaaacauuuc ac                                               22
```

US 9,080,172 B2

TARGETING P63 TO RE-ACTIVATE DORMANT RESERVE STEM CELLS IN OLFACTORY EPITHELIUM

CROSS REFERENCE TO RELATED APPLICATIONS

This application is a 35 U.S.C. §371 National Phase Entry Application of International Application No. PCT/US2012/039688 filed May 25,2012, which designates the U.S., and which claims the benefit under 35 U.S.C. §119(e) of U.S. Provisional Application Ser. No. 61/491,099, filed May 27, 2011, and of U.S. Provisional Ser. No. 61/493,243, filed Jun. 3, 2011, the contents of each of which are incorporated herein by reference in their entireties.

GOVERNMENTAL SUPPORT

This invention was made with Government support under RO1DC002167 and F30DC011241 awarded by the National Institutes of Health. The Government has certain rights in the invention.

SEQUENCE LISTING

The instant application contains a Sequence Listing which has been submitted electronically on ASCII format and is hereby incorporated by reference in its entirety. Said ASCII copy, created on Nov. 22,2013, is named 700355-070813-US_SL.txt and is 1,960 bytes in size.

FIELD OF THE INVENTION

The present invention relates to the field of adult stem cells and the therapeutic treatment of olfactory disorders.

BACKGROUND OF THE INVENTION

The human olfactory epithelium normally retains the lifelong capacity to make new olfactory sensory neurons to maintain sensory function or restore it after injury. In some aged individuals, that capacity is lost, because the normal stem cells responsible for neurogenesis become exhausted. There is also a population of reserve stem cells, called horizontal basal cells (HBCs), which are activated by injury to restore neurogenic capacity, but do not activate with mere stem cell exhaustion. A method to induce these reserve stem cells to replenish olfactory neuroepithelium under different circumstances would be useful in the treatment of various olfactory disorders.

SUMMARY OF THE INVENTION

Aspects of the invention relate to a method for activating a dormant epithelial stem cell, or population thereof, to a state of multipotency comprising, reducing the level of $\Delta$Np63 in the cell(s). In one embodiment, the dormant epithelial stem cell(s) is a horizontal basal cell (HBC) of the olfactory epithelium. In one embodiment, reducing the level of $\Delta$Np63 is by contacting the cell or population with an effective amount of one or more agents that downmodulate $\Delta$Np63. In one embodiment, the agent(s) is exogenous or endogenous to the organism in which the cell exists naturally. In one embodiment, the agent(s) inhibits $\Delta$Np63 gene expression, $\Delta$Np63 protein synthesis, $\Delta$Np63 protein function, $\Delta$Np63 protein activity, or combinations thereof. In one embodiment, the agent(s) is an RNAi. In one embodiment, the agent(s) is a micro RNA. In one embodiment, the microRNA is micro RNA 203. In one embodiment, the one or more agents is selected from the group consisting of a chemical, small molecule, nucleic acid sequence, nucleic acid analogue, protein, peptide, aptamer, antibody or fragment thereof, and combinations thereof. In one embodiment of any of the herein described methods, the cell(s) is a mammalian cell. In one embodiment, the cell(s) is a human cell. In one embodiment of any of the herein described methods, the cell(s) is in vitro or in vivo. In one embodiment of any of the herein described methods, the cell(s) is in vivo, and contacting is by administering the agent(s) in the form of a pharmaceutical composition to a subject to thereby contact the cell(s).

Another aspect of the invention relates to a method for treating olfactory dysfunction in a subject, comprising activating HBCs of the subject by reducing the level of $\Delta$Np63 in one or more HBCs of the subject, to thereby treat the olfactory dysfunction. In one embodiment, reducing the level of $\Delta$Np63 is by administering a therapeutically effective amount of a pharmaceutical composition that comprises one or more agents that downmodulate $\Delta$Np63, to the subject, to thereby contact the agent with the HBCs. In one embodiment, the agent(s) inhibits $\Delta$Np63 gene expression, $\Delta$Np63 protein synthesis, $\Delta$Np63 protein function, $\Delta$Np63 protein activity, or combinations thereof. In one embodiment of the herein described methods, the agent(s) is an RNAi. In one embodiment of the herein described methods, the agent(s) is a micro RNA. In one embodiment, the microRNA is micro RNA 203. In one embodiment, the one or more agents is selected from the group consisting of a chemical, small molecule, nucleic acid sequence, nucleic acid analogue, protein, peptide, aptamer, antibody or fragment thereof, and combinations thereof. In one embodiment of the herein described methods, the subject is a mammal. In one embodiment, the subject is a human. In one embodiment, the HBC is in vitro, and implanted into the subject following activation. In one embodiment of the herein described methods, the olfactory dysfunction is anosmia or hyposmia. In one embodiment of the herein described methods, the olfactory dysfunction is due to the degeneration of peripheral neurons in the olfactory epithelium of the subject. In one embodiment of the herein described methods, the olfactory dysfunction is due to age. In one embodiment of the herein described methods, the olfactory dysfunction is due to injury. In one embodiment of the herein described methods, the olfactory dysfunction is due to disease. In one embodiment of the herein described methods, administration is localized. In one embodiment of the herein described methods, administration is via nasal infusion.

Another aspect of the invention relates to an isolated activated horizontal basal cell (HBCs) or population thereof. In one embodiment, the cell is mammalian. In one embodiment, the cell is human. In one embodiment of any one of the isolated cells or populations thereof described herein, the cell or population exhibits reduced levels of $\Delta$Np63, as compared to non-activated HBCs, or exhibits reduced expression of $\Delta$Np63, as compared to non-activated HBCs. In one embodiment of any one of the isolated cells or populations thereof described herein, the reduced expression and/or reduced levels of $\Delta$Np63 results from contacting the cell or population with an effective amount of one or more exogenous agents that downmodulates $\Delta$Np63. In one embodiment of any one of the isolated cells or populations thereof described herein, the exogenous agent(s) inhibits $\Delta$Np63 gene expression, $\Delta$Np63 protein synthesis, $\Delta$Np63 protein function, $\Delta$Np63 protein activity, or combinations thereof. In one embodiment of any one of the isolated cells or populations thereof described herein, the agent(s) is an RNAi, such as a micro RNA (e.g., micro RNA 203).

BRIEF DESCRIPTION OF THE DRAWINGS

FIG. 1A depicts the olfactory epithelium. FIG. 1B depicts a schematic of cellular regeneration after MeBr injury, including the involvement of Notch signaling and the discrete stages in GBC progression.

FIG. 2A is a model of HBC development from Ascl1(+) and/or Hes1(+) OPPs/GBCs. FIG. 2B is a model of how HBC activate and return to quiescence after lesion, tested by experiments described herein.

FIG. 7A depicts the quantification of p63(+) cells that are also Hes1(+) or Ascl1(+). For Hes1 asterisks indicates $p<0.01$ compared to previous time point by ANOVA analysis. For Ascl1 one-way ANOVA analysis indicates a statistically significant trend over time. FIGS. 7B-C show quantification of acute pulse EdU incorporation as compared to p63 expression at E16, P0, and P10. Analysis of the number of EdU(+) and p63(+) cells/mm of OE (7B) and the percentage of p63(+) that incorporate EdU (14C) reveal no significant differences during development by ANOVA analysis.

FIG. 10A depicts a model of how HBCs develop from OPPs/GBCs in the embryo. OPPs/GBCs may transiently express Ascl1 in some cases before turning on p63 and Hes1 to become HBC progenitors. HBC progenitors then turn on expression of K5/K14 and flatten against the basal lamina. FIG. 10B depicts a model of how after severe injury to the OE, such as caused by MeBr expression, HBCs down-regulate p63 as they become multipotent progenitor cells.

FIG. 11A depicts the total number of cells per clone and FIG. 11B depicts the proportion of cell types within each clonal population.

FIGS. 12B and 12D are magnified images of the areas demarcated by the black boxes in FIGS. 12A and 12C, respectively. FIGS. 12A-12B depict epithelium from mice that did not receive tamoxifen treatment to knock-out p63. Cells with Cre-ERT2 recombination of R26R tracer locus remain as HBCs, plastered against the basal lamina (arrowheads). FIGS. 12C-12D depict epithelium where p63 has been eliminated by tamoxifen treatment. In these mice, HBCs activate and differentiate into multiple other cell types located in the upper parts of the epithelium.

FIG. 13A depicts the floxed p63 construct. FIG. 13B depicts a model of the HBC response to MeBr and the question that Example 3 addresses.

FIG. 18A is a schematic of retrovirally derived vectors used to transduce gene expression in individual basal cell progenitors: MIG encodes GFP only; MIG-p63 encodes bicistronic message of p63 and GFP. FIG. 18B is a data chart of p63 over expression (MIG-p63, squares on the right) prevents the formation of large clones. Clone composition was studied. Without overexpression of p63 (MIG), the clones generated from the individual clonal progenitors in the lesioned OE were highly complex in composition as well as large, and includes neurons HBCs, GBCs, and sus cells (CK14 was used to identify HBCs, PGP9.5 was used to identify neurons, GBCs were located in between HBCs and neurons, and sus cell were located superficial to neurons). When p63 was overexpressed (MIG-p63), mostly HBCs were seen. FIG. 18C and FIG. 18D are compiled data from all clones.

DETAILED DESCRIPTION OF THE INVENTION

Figure 1A:
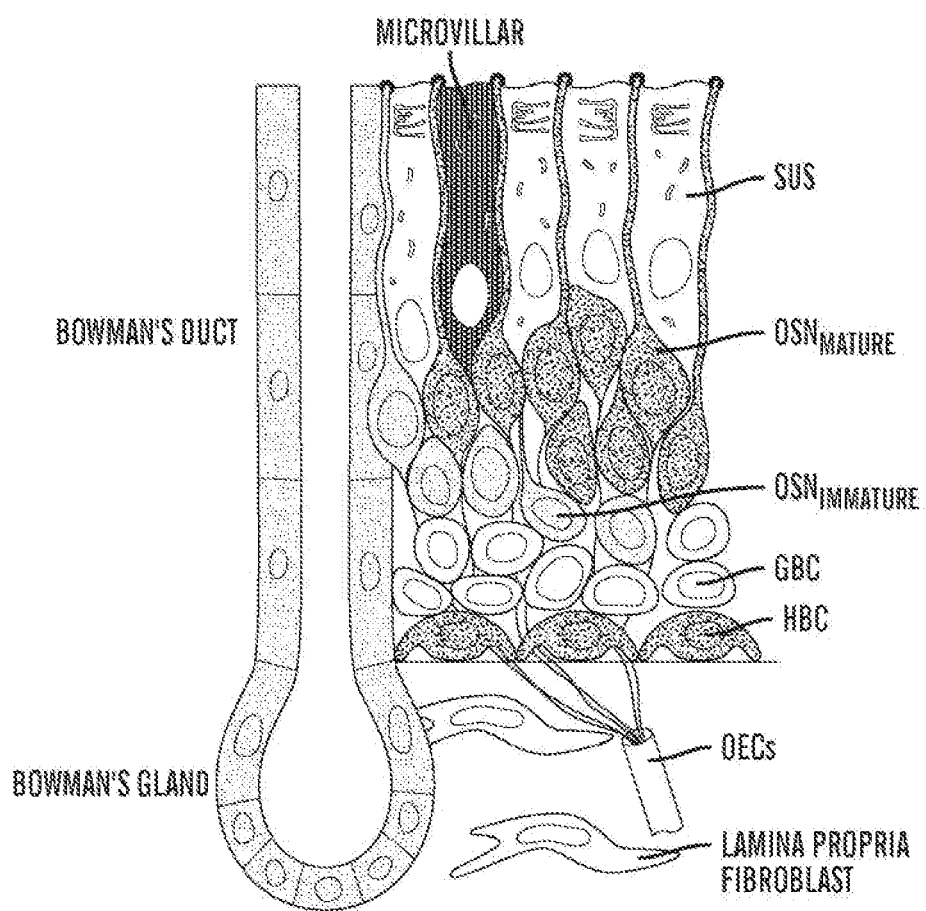
FIG. 1A-FIG. 1B are diagrams of tissue organization and regeneration.

Aspects of the present invention arise from the finding that a reduction in the amount of ΔNp63 in dormant epithelial stem cells (e.g., horizontal basal cells (HBCs) of the olfactory epithelium) is necessary and sufficient for release of those cells from dormancy into an activated state. Such activated cells are in a proliferative state, are multipotent, and can serve to repopulate neuronal and non-neuronal cell types of an epithelium (such as the olfactory epithelium). For example, HBCs activated by the methods described herein can differentiate into both neuronal and non-neuronal (e.g., glial) cell types in the olfactory epithelium, and serve to repopulate those cells in a damaged or otherwise dysfunctional olfactory epithelium. As such, one aspect of the present invention relates to a method to induce a dormant or reserve epithelial stem cell, or population thereof, to a proliferative and multipotent state by reducing the amount of ΔNp63 in the cells (e.g., horizontal basal cells).

In one embodiment, the amount or level of ΔNp63 in the cell is reduced by contacting the cell or population of cells with an effective amount of one or more agents that downmodulate ΔNp63. The method can be performed in vitro (e.g. on isolated dormant epithelial stem cells) or in vivo, as described herein.

Activation of a dormant epithelial stem cell, as the term is used herein, refers to an induced ability to serve as a multipotent stem cell. Such activation is typically concurrent with the expression of cell type specific markers for the activated cells. In one embodiment, activation is concurrent with a change in the amount of cell adhesion molecules (e.g. a reduction). A reduction in adhesion molecules allows the migration of the cells, which is typically required for multipotency. A change in the expression of other such molecules may also occur. In one embodiment, activation of an HBC can be detected by a reduction in the detectable level of ICAM 1 (CD54) and/or cytokeratins 5 and 14.

The cell that is suitable for activation is competent in its ability to serve as an epithelial stem cell, but otherwise is dormant (e.g., quiescent). The cell necessarily expresses significant levels of ΔNp63 and has not otherwise received stimulation (e.g, endogenous stimulation such as olfactory injury to activate HBCs). For example, HBCs in an adult subject are dormant yet competent upon activation by the methods described herein. As such activation of the HBCs by the methods described herein serve to induce multipotency of HBCs.

A reduction in the amount of the p63, and/or another marker, is in relation to the amount expressed by that cell prior to performance of the methods described herein. Such a determination can be made by comparison to an appropriate control cell or population thereof. Such an appropriate control cell is, for example, the same type of cell (e.g., a HBC), that has been exposed to the same conditions, but in the absence of the activation (e.g., exposure to the downmodulatory agent). When making an in vitro determination, the cells can be derived from the same origin to ensure that they are comparable.

Another aspect of the invention relates to a method of treating a subject for olfactory dysfunction (e.g., degeneration or injury) by activating the dormant stem cells of the subject (e.g., HBCs that express p63). Such cells are activated, for example, by reducing the level of p63 therein. In one embodiment, the reduction is accomplished by contacting the dormant stem cells (e.g., HBCs) of the subject with an agent that downmodulates p63. The agent can be administered to the subject in the form of a pharmaceutical composition that comprises one or more agents, in a therapeutically effective amount. Since the activated epithelial stem cells can differentiate into neurons, another aspect of the invention is a method for stimulating adult neurogenesis in a subject by activation of the dormant epithelial stem cells as described herein.

Activation of dormant HBCs of a subject can ultimately stimulate neurogenesis in the olfactory epithelium. As such, aspects of the invention further relate to methods for inducing replenishment of cells in the olfactory epithelium of a subject. Such methods are accomplished by administering a therapeutic amount of a pharmaceutical composition described herein, by the methods described herein, to thereby promote activation of dormant HBCs of a subject.

The therapeutic methods described herein are useful in the treatment of a subject for a neuronal disorder that arises from injury or a nervous system disease. Such methods described herein when applied to HBCs of the olfactory epithelium are useful for the promotion of neurogenesis in the olfactory epithelium of a subject. Such methods are used to promote the generation of olfactory sensory neurons in a subject in need thereof. Olfactory dysfunction can arise from a variety of circumstances including age, injury, disease, and combinations thereof. The therapeutic methods described herein are useful in the treatment of subjects which have a condition such as an altered sense of smell that arises from olfactory degeneration or injury. In one embodiment, the condition is associated with the loss of olfactory neurons in the subject. Such conditions are referred to in the art as dysosmia, anosmial, hyposmia. In one embodiment, the condition is peripheral anosmia.

Other aspects of the present invention relate to the identification of lineage commitment of stem cells (e.g., of the olfactory epithelium). Stem cells that are appropriately committed (referred to herein as "activated") can serve to repair and re-populate damaged epithelial tissue, including damaged neuronal tissue (e.g., damaged olfactory epithelial tissue, including olfactory neuronal cells). Such cells may be identified by the methods described herein and obtained from a subject (e.g., in progenitor form or activated form) and if desired further isolated from a heterogeneous population. Such isolated cells obtained by the methods described herein are encompassed by the present invention. Identification and isolation is based on expression level of markers disclosed herein of the desired cell type. In one embodiment, the cells originate in an adult organism. In one embodiment, the cells are horizontal basal cells of the olfactory epithelium that have reduced expression of p63, as described herein.

Activated stem cells (e.g. activated HBCs) can be obtained from a subject in their activated form, or alternatively can be obtained from a subject in a dormant stage and manipulated in vitro to the activated state by the methods described herein. Cells obtained from a subject may be further manipulated in vitro, for example, expanded in number, induced into further differentiation, and/or used for diagnosis, and/or screening of therapeutic agents. The cells may be (re-)introduced into a subject for therapeutic purposes (e.g., to re-populate/repair damaged tissue such as damaged olfactory epithelium).

Another aspect of the present invention relates to isolated activated epithelial stem cells generated in vivo by the methods described herein or otherwise obtained from an in vivo source. Such cells can be obtained, for example, by obtaining a tissue or cell sample isolated from a subject, likely to contain such cells (e.g., from olfactory epithelium) and identifying and selecting for activated epithelial stem cells within the obtained sample. Such selection can be, for example, on the basis of expressed proteins, described herein. Useful methods of identifying and selecting such cells include, without limitation, immunological based methods, such as FACS. Once obtained, these cells can be further used in the methods described herein. In one embodiment, the cells of the present invention, described herein, have a normal karyotype.

Molecules that are detectable on the surface of the cell can be used in the determination and/or isolation of activated epithelial stem cells described herein (e.g., in FACS analysis and cell sorting). A shift from quiescence also typically occurs with activation, and detection of one or more markers of this shift can also be used to identify and/or isolate activated cells. Such changes in markers are detectable, for example, within about 24 hours of performance of the methods described herein. In some embodiments, the markers will be detectable at about 48 hours. In some embodiments, early detection of markers is possible and useful to distinguish the activated cells described herein (e.g., within ≤1 hour, ≤2 hours, ≤3 hours, ≤4 hours, ≤5 hours, ≤6 hours, ≤7 hour, ≤8 hours, ≤9 hours, ≤10 hours, ≤11 hours, ≤12 hours, ≤13 hours, ≤14 hours, ≤15 hours, ≤16 hours, ≤17 hours, ≤18 hours, ≤19 hours, ≤20 hours, ≤21 hours, ≤22 hours, ≤23 hours, or ≤24 hours of performance of the methods described herein).

The cells of the present invention can be used for diagnostic purposes, such as to diagnose an individual wherein that diagnosis requires a specific cell type of the individual. The cells may then be characterized by methods appropriate for the diagnostic purposes. For example, the cells can be characterized for gene expression by analysis of their nucleic acid expression for one or more genes of interest. This can be done, for example, by determining the levels of mRNA transcribed from a gene(s) of interest (e.g., by northern blot analysis, PCR, etc.). Another example is characterization of the cells for protein expression of one or more proteins of interest. Protein expression can be determined qualitatively and/or quantitatively, for example, using immunodetection methods for a specific protein (e.g, Western blot analysis, immunoprecipitation, fluorescent activated cell sorting, etc.). The cells may also be characterized on the basis of their response to exposure to one or more agents of interest (e.g., a drug or toxin). Characterization of the cellular response to a drug can be used to determine an appropriate treatment regimen for the individual from whom the cells are obtained. As such, another aspect of the present invention relates to a method for drug testing for an individual. The method comprises obtaining cells from the individual, by the methods described herein, and inducing those cells to differentiate into one or more cell type described herein, and performing drug testing on those cells, to thereby determine the likelihood of pharmacological efficacy of the drug on the individual in a treatment regimen. An indication of non-responsiveness of the tested cells, compared to an appropriate control, would indicate low or no pharmacological efficacy of the drug on the individual. As such, it would indicate that the individual is unlikely to be responsive to a treatment regimen using that drug. An indication of responsiveness of the tested cells to the drug, compared to an appropriate control, An indication of non-responsiveness of the tested cells, compared to an appropriate control, would indicate pharmacological efficacy of the drug on the individual. Such a result would indicate a likelihood of the individual to be responsive to a treatment regimen using that drug. Such drug testing can be used in methods of determining treatment of an individual with a disease.

The cells of the present invention may also be used in assays of toxicity. The cells may be used in multipotent form, or further induced to a more differentiated state. The use of the cells described herein may be preferred in certain assays of toxicity, as such cells more closely resemble the cell types present in the tissues and organs of an organism. These differentiated cells will be very useful in assays of toxicity performed in vitro, i.e., using cultured cells or suspensions of cells. Such in vitro assays examine the toxicity to cultured cells or suspended cells of compounds or compositions, e.g., chemical, pharmaceutical or biological compounds or compositions, or biological agents. In this context, a particular compound or composition may be considered toxic or likely toxic, if it shows a detrimental effect on the viability of cells or on one or more aspect of cellular metabolism or function. Typically, the viability of cells in vitro may be measured using colorimetric assays, such as, e.g., the MTT (or MTT derivative) assays or LDH leakage assays, or using fluorescence-based assays, such as, e.g., the Live/Dead assay, GyQuant cell proliferation assay, or Essays of apoptosis. Other assays may measure particular aspects of cellular metabolism or function. While the above are non-limiting examples, a person skilled in the art will be able to make an appropriate choice of assay of toxicity to use in combination with the differentiated cells provided by the present invention, and will be knowledgeable of the technical requirements to perform such assay. Accordingly, in an embodiment, the present invention provides a differentiated cell or cells for use in assays of toxicity. In another embodiment, the present invention provides a differentiated cell or cells of human or animal origin for use in assays of toxicity. The use of human cells in assays of toxicity will provide a relevant reference for the potential toxicity of chemical compounds, compositions, or agents on the cell types present in human or animal tissues or organs, respectively. Moreover, because such chemical compounds or compositions may also be comprised in a sample obtainable from the environment, in one embodiment the present invention also provides differentiated cells for use in assays of ecological toxicity.

The olfactory neuroepithelium, also referred to herein as the olfactory epithelium, is composed of receptor and supporting cells and olfactory glands of Bowman, located in the superior part of the nasal cavities. The receptor cells are neurons with dendritic extensions into the overlying mucus and axons that transverse the cribriform plate as the olfactory fila and synapse with second-order neurons in the glomeruli of the olfactory bulb. The olfactory neuroepithelium is a simple pseudostratified neuroepithelium and consists of two major differentiated cell types, the olfactory receptor neurons (ORNs) and glial-like sustentacular cells. Additionally, Bowman's glands and ducts extend through the olfactory neuroepithelium and secrete mucus to the apical surface of the epithelium. The cells that contribute to ongoing neurogenesis lie near the basal lamina in the pseudostratified olfactory neuroepithelium (Mackay-Sim, A. et al., J. Neurosci. 11, 979-984 (1991); Caggiano, M. et al., Neuron 13, 339-352 (1994)). This basal germinal zone is comprised of globose basal cells (GBCs) and HBCs (Calof, A. L. et al., Microsc. Res. Tech. 58, 176-188 (2002)). The GBCs are the major proliferating population in the olfactory neuroepithelium (Caggiano supra) and contain multipotent progenitors that give rise to neurons and sustentacular cells (Huard, J. M. et al., J. Comp. Neurol. 400, 469-486 (1998); Chen, X. et al., J. Comp. Neurol. 469, 457-474 (2004)). The progenitors in the ORN lineage that reside among the GBC population sequentially express the proneural genes Ascl1 (also known as Mash1) and Neurog1 (also known as Ngn1) (Cau, E. et al., Development 129, 1871-1880 (2002)). Mash1+GBCs are the earliest ORN precursors identified (Calof supra), but their cell dynamics indicate that they are transit-amplifying progeny of a putative olfactory neuroepithelium stem cell (Gordon, M. K. et al., Mol. Cell. Neurosci. 6, 363-379 (1995)). Without being bound by theory, it is thought that activation of the HBCs by the methods described herein promotes their differentiation into GBCs, from which state they differentiate into the various cell types of the olfactory neuroepithelium as needed.

As there term is used herein, reducing the amount or level of p63 in a cell refers to reducing the amount or level of functional ΔNp63 in the cells. The function of the p63 that is critical for the methods described herein is the ability to maintain the cells in a state of quiescence. Upon inhibition of that activity (e.g., by inhibition of protein function, degradation of the protein, sequestering of the protein in a nonfunctional complex, or a reduction in the amount of protein generated from expression) the cells become activated. A complete elimination of functional p63 is not necessary to activate the dormant epithelial stem cells. It is thought that a 75-80% reduction in the amount of the functional p63 protein in a cell or population of cells is sufficient to lead to activation. A significant amount of cells in a population may be activated by even a reduction of less than 75% of the functional p63 protein. For example, a reduction in the amount of protein that is ≤75%, ≤70%, ≤65%, ≤60%, ≤55%, ≤50%, or ≤45% is expected to produce detectable activation within the population. In one embodiment, the inhibition is to the point of undetectable functional p63. In one embodiment, the inhibition is ≤99%, ≤95%, ≤90%, ≤85%, or ≤80% of functional p63.

The amount of p63 can be detected by various detection methods described in the art, and exemplified herein. For example, by immunodetection methods such as immunohistochemistry and western blot analysis. p63 amount can also be detected by detection of the mRNA, for example by quantitative PCR, Northern blot analysis, and other method known in the art. Also, functional p63 can be detected through detection of p63 function, e.g., activation or lack thereof, of a downstream target. A reduced level of active protein or gene expression can be determined, for example, by comparison to the amount in a control cell or comparable cell type under adequately controlled conditions. In one embodiment, the reduction is such that no active protein, and/or gene expression is detectable in the cell. It is expected that a significant reduction, without complete elimination may produce useful results in a cell. As such, in one embodiment, the reduction is such that the cell exhibits ≤1% of the active protein and/or gene expression (e.g., of p63) exhibited by a control cell. Higher amounts of active protein and/or gene expression which are still significantly less than that of a control cell may also be useful in the methods of the invention (e.g., such that the cell exhibits ≤5%, ≤10%, ≤20%, ≤30%, ≤40%, ≤50%, ≤60%, ≤70% of the active protein and/or gene expression of a control cell).

p63 p63 is a well characterized protein. It is a known tumor suppressor. p63 is also known as tumor protein p63 and transformation-related protein 63. In humans, it is encoded by the TP63 gene. Other symbols for the p63 gene include TP63; TP73L; p63; B(p51A); B(p51B); EEC3; KET; LMS; OFC8; RHS; SHFM4; p51; p73H; p73L. p63, and the gene encoding p63 has been identified in humans, mice and other organisms (Yang et al., Mol. Cell. 2 (3): 305-16 (1998); Osada et al., Nat. Med. 4 (7): 839-43 (1998)).

There are 6 isoforms of p63. They are produced by alternative splicing, and vary at the N-terminus by either containing or lacking an acidic N-terminus corresponding to the transactivation domain. Isoforms that contain the N-terminus are referred to as TAp63, isoforms that lack the N-terminus are referred to has ΔNp63. These two forms can each contain one of three C-terminal domains, corresponding to α, β, and γ, thus producing TAp63α, TAp63β, and TAp76γ, ΔNp63α, ΔNp63β, and ΔNp63γ. The nucleotide and amino acid sequences of the various p63 isoforms, and methods of identifying the various isoforms of the p63 proteins and nucleic acids are described in U.S. Pat. No. 7,294,459.

The ΔNp63 isoforms are relevant for epithelial development, and found in the adult olfactory epithelium. As the term is used herein in reference to epithelial cells (e.g., horizontal basal cells), p63 refers to the ΔNp63 isoform, as this is found in epithelial cells, and particularly in horizontal basal cells. Both the ΔNp63α and ΔNp63 isoforms are expressed in the OE. As such, downmodulation of either, or both, isoforms as described herein, is encompassed by the present invention. Furthermore, downmodulation of the ΔNp63γ isoform is also expected to produce some desired results. Due to the similarity of the different isoforms, there is expected to be cross-reactivity of inhibitors with respect to the different isoforms. For example, an inhibitor designed to inhibit the α, β, or γ isoform, may also inhibit one, or both, other isoforms. Method of the invention encompass inhibition of one, two or all three isoforms (e.g, by the use of different inhibitors, or one inhibitor that has such crossreactivity). It however is possible to design inhibitors that specifically inhibit one or two isoforms. Methods of the invention also encompass such specific inhibition of one or two isoforms. As such, one embodiment of the invention encompasses downmodulation of one or more or all of the three C-terminal isoforms of the ΔNp63 (e.g. from contacting a cell with one or more agents that downmodulate the specific isoforms (e.g., ΔNp63α, and/or ΔNp63β, and/or ΔNp63γ isoform). In one embodiment, the contacting is by administering to a subject a pharmaceutical composition containing such agent(s) by the methods described herein.

Sequences for the human and murine p63 cDNAs are publically available. For example, sequences for the human and murine p63 cDNAs have been deposited under the following accession numbers: Hu TAp63γ, AF075428; Hu ΔNp63γ, AF075429; Hu TAp63α, AF075430; Hu ΔNp63α, AF075431; Hu TAp63β, AF075432; Hu ΔNp63β, AF075433; Mu TA*p63γ, AF075434; Mu TA*p63β, AF075435; Mu TA*p63α, AF075436; Mu ΔNp63γ, AF075437; Mu ΔNp63β, AF075438; and Mu ΔNp63α, AF075439.

Modulation

Downmodulation of p63 can be achieved by inhibition of p63 protein expression (e.g., transcription, translation, post-translational processing) or protein function. In one aspect of the invention the level of p63 in a cell is reduced by contacting the cell with an agent that downmodulates p63 in the cell. Such agents are described herein. A reduction in p63 may also be achieved by modulation of an upstream activator/inducer of ΔNp63 (e.g., Notch or Wnt1).

It may also be useful to upmodulate p63 in a cell (e.g., prior to downmodulation) in order to move that cell into an appropriate stage of differentiation so that it can then be activated by the methods described herein. As such, the present invention further encompasses upmodulation of p63 when necessary. Downmodulation and/or upmodulation can be performed in vitro or in vivo.

Agents for Modulation

Agents for upmodulation or downmodulation, as described herein can be chemicals; small molecules; nucleic acid sequences; nucleic acid analogues; proteins; peptides; aptamers; antibodies; or fragments thereof. Many such agents are known in the art and can be used in the present invention. Other such agents can be identified or generated for use in the present invention.

Such an agent can take the form of any entity that is normally not present or not present at the levels being provided to the cell(s). Agents such as chemicals; small molecules; nucleic acid sequences; nucleic acid analogues; proteins; peptides; aptamers; antibodies; or fragments thereof, can be identified or generated for use to downmodulate the ΔNp63.

Agents in the form of a protein and/or peptide or fragment thereof can be used to downmodulate the ΔNp63. Such agents encompass proteins that are normally absent or proteins that are normally endogenously expressed in the host cell. Examples of useful proteins are mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Agents also include antibodies (polyclonal or monoclonal), neutralizing antibodies, antibody fragments, peptides, proteins, peptide-mimetics, aptamers, hormones, small molecules, carbohydrates or variants thereof that function to inactivate the nucleic acid and/or protein of the gene products identified herein, and those as yet unidentified. Inhibitory agents can also be a chemical, small molecule, chemical entity, nucleic acid sequences, nucleic acid analogues or protein or polypeptide or analogue or fragment thereof.

The agent may function directly in the form in which it is administered. Alternatively, the agent can be modified or utilized intracellularly to produce something which downmodulates the ΔNp63, such as introduction of a nucleic acid sequence into the cell and its transcription resulting in the production of the nucleic acid and/or protein inhibitor of ΔNp63 within the cell. The agent can be made from any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The agent may comprise a vector. Many such vectors useful for transferring exogenous genes into target mammalian cells are available. The vectors may be episomal, e.g., plasmids, virus derived vectors such cytomegalovirus, adenovirus, etc., or may be integrated into the target cell genome, through homologous recombination or random integration, e.g., retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) P.N.A.S. 95 (20): 11939-44). As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

In one embodiment, the agent inhibits gene expression (i.e., suppress and/or repress the expression of a gene of interest (e.g., the p63 gene)). Such agents are referred to in the art as "gene silencers" and are commonly known to those of ordinary skill in the art. Examples include, but are not limited to a nucleic acid sequence, (e.g., for an RNA, DNA, or nucleic acid analogue). These can be single or double stranded. They can encode a protein of interest, can be an oligonucleotide, a nucleic acid analogue. Included in the term "nucleic acid sequences" are general and/or specific inhibitors. Some known nucleic acid analogs are peptide nucleic acid (PNA), pseudo-complementary PNA (pc-PNA), locked nucleic acids (LNA) and derivatives thereof. Nucleic acid sequence agents can also be nucleic acid sequences encoding proteins that act as transcriptional repressors, antisense molecules, ribozymes, small inhibitory nucleic acid sequences (e.g., RNAi, shRNAi, siRNA, micro RNAi (miRNA), and antisense oligonucleotides. Many such molecules for inhibiting p63 are known in the art. As such these inhibitors can function as an agent in the present invention.

One type of downmodulatory agent for use in the present invention is an RNAi molecule (e.g., an siRNA or miRNA). The term "RNAi" and "RNA interfering" with respect to an agent of the invention are used interchangeably herein. The term "RNAi" as used herein refers to interfering RNA or RNA interference, which is a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

RNAi molecules are typically comprised of a sequence of nucleic acids or nucleic acid analogs, specific for a target gene. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example an HDF gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length). An siRNA can be chemically synthesized, it can be produced by in vitro transcription, or it can be produced within a cell specifically utilized for such production.

In one embodiment, the siRNA is designed for inhibition of expression of ΔNp63. Examples of such siRNA and methods of use to inhibit expression are known in the art (Published Patent Application WO 2010/039679; Truong et al., Genes & Dev. 20: 3185-3197 (2006); Barbieri et al., Cancer Res 65:2314-2320 (2005); Yuan et al., BMC Cancer 11:57 (2011); Yang et al. Cancer Res 71:3688-3700 (2011)). In one embodiment, the siRNA sequence comprises: sense: 5'-AACAGC-CAUGCCCAGUAUGUA-3' (SEQ ID NO: 1); anti-sense: 5'-UACAUACUGGGCAUGGCUGUU-3' (SEQ ID NO: 2). In another embodiment, the siRNA sequence comprises sense: 5'-CAA UGC CCA GAC UCA AUU UTT-3' (SEQ ID NO: 3); anti-sense: 5'-TT GUU ACG GGU CUG AGU UAA A-3' (SEQ ID NO: 4).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow. shRNAs functions as RNAi and/or siRNA species but differs in that shRNA species are double stranded hairpin-like structure for increased stability. These shRNAs, as well as other such agents described herein, can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

In one embodiment, the RNAi is a microRNA. microRNAs (miRNAs) are short RNA molecules (16-29 nucleotides in length) that arise from longer precursors, which are transcribed from non-protein coding genes (Carrington et al Science, 301 (5631):336-338, 2003). The precursors are processed by cellular proteins to generate short double-stranded miRNA. One of the miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA or its target mRNA (Bagga et al, Cell, August 26; 122 (4):553-63. 2005; Lim et al, Nature, 433 (7027):769-73, 2005). In one embodiment, the microRNA occurs naturally in the organism from which the dormant epithelial stem cell originates. In one such example, the miRNA is found naturally in a different cell type, but in the same organism, as the dormant epithelial stem cell. In another embodiment, the miRNA occurs naturally in a different organism from which the dormant epithelial stem cell originates (e.g., a closely related species).

MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

miRNAs that inhibit ΔNp63 are known to exist in nature and can be used in the methods described herein. In one embodiment the RNAi is a naturally occurring micro RNA. In one embodiment, the micro RNA is micro RNA 203 (Yi et al., Nature 13; 452 (7184):225-9 (2008); Yuan et al., BMC Cancer 11:57 (2011)). In one embodiment, the sequences of miR-203 is: sense: 5'-GUGAAAUGUUUAGGACCACUAG-3' (SEQ ID NO: 5), anti-sense: 5'-CUAGUGGUCCUAAA-CAUUUCAC-3' (SEQ ID NO: 6). In one embodiment, the micro RNA originates from the species of cell or subject to which it is contacted (e.g., a human miRNA for a human cell and/or subject).

In one embodiment, use of the agent is to thereby result in a decrease in the target mRNA (e.g., p63) level in a cell by at least about 5%, about 10%, about 20%, about 30%, about 40%, about 50%, about 60%, about 70%, about 80%, about 90%, about 95%, about 99%, about 100% of the mRNA level found in the cell without the presence of the RNAi. In one embodiment, the mRNA levels are decreased by at least about 70%, about 80%, about 90%, about 95%, about 99%, or about 100%.

An agent for downmodulation as described herein may also be an antibody that specifically binds to the target molecule (e.g., ΔNp63). Such antibodies can be monoclonal or polyclonal. Such antibodies can be generated using methods well known in the art. For example, the production of non-human monoclonal antibodies, e.g., murine or rat, can be accomplished by, for example, immunizing the animal with an HDF identified herein, or its fragment (See Harlow and Lane, Antibodies, A Laboratory Manual, Cold Spring Harbor Press, 3rd ed., 2000). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to a target molecule. Human antibodies against a target molecule can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using the target molecule or its fragment.

Delivery of Agents to the Cell

The agent is contacted to the cell such that it can exert its intended effect on the cell. In one embodiment, the agent exerts its effects on the cells merely by interacting with the exterior of the cell (e.g., by binding to a receptor). Agents that act on the cell internally (e.g., RNAi) may be delivered in a form that is readily taken up by the cell when contacted to the cell (e.g., in a formulation which facilitates cellular uptake and delivery to the appropriate subcellular location). In one embodiment, the agent is in a formulation in which it is readily taken up by the cell so that it can exert it effect.

Colloidal dispersion systems may be used as delivery vehicles and to enhance the in vivo stability of the agent to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708). Other examples of cellular uptake or membrane-disruption moieties include polyamines, e.g. spermidine or spermine groups, or polylysines; lipids and lipophilic groups; polymyxin or polymyxin-derived peptides; octapeptin; membrane pore-forming peptides; ionophores; protamine; aminoglycosides; polyenes; and the like. Other potentially useful functional groups include intercalating agents; radical generators; alkylating agents; detectable labels; chelators; or the like.

Other colloidal dispersion systems lipid particle or vesicle, such as a liposome or microcrystal, may be suitable for administration. The particles may be of any suitable structure, such as unilamellar or plurilamellar, so long as the antisense oligonucleotide is contained therein. Positively charged lipids such as N-[I-(2,3dioleoyloxi)propyll-N,N,N-trimethyl-anunoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757, which are incorporated herein by reference. Other non-toxic lipid based vehicle components may likewise be utilized to facilitate uptake of the nucleic acid compound by the cell.

In some embodiments, in order to increase nuclease resistance in an RNAi agent as disclosed herein, one can incorporate non-phosphodiester backbone linkages, as for example methylphosphonate, phosphorothioate or phosphorodithioate linkages or mixtures thereof, into one or more non-RNASE H-activating regions of the RNAi agents. Such non-activating regions may additionally include 2'-substituents and can also include chirally selected backbone linkages in order to increase binding affinity and duplex stability. Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532, which is incorporated herein in by reference.

Methods of delivering RNAi interfering (RNAi) agents, e.g., an siRNA, or vectors containing an RNA interfering agent, to the target cells (e.g., horizontal basal cells) can include, for example (i) injection of a composition containing the RNA interfering agent, e.g., an siRNA, or (ii) directly contacting the cell, with a composition comprising an RNA interfering agent, e.g., an siRNA. In another embodiment, RNA interfering agents, e.g., an siRNA can be injected directly into any blood vessel, such as vein, artery, venule or arteriole, via, e.g., hydrodynamic injection or catheterization. In some embodiments RNAi agents such as siRNA can be delivered locally to specific organs or by systemic administration.

Pharmaceutical Compositions

In one embodiment, the agent described herein is an active ingredient in a composition comprising a pharmaceutically acceptable carrier (referred to herein as a pharmaceutical composition). Such a composition is referred to herein as a pharmaceutical composition. A "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the composition and is compatible with administration to a subject, for example a human. Such compositions can be specifically formulated for administration via one or more of a number of routes, such as the routes of administration described herein. Supplementary active ingredients also can be incorporated into the compositions. When an agent, formulation or pharmaceutical composition described herein, is administered to a subject, preferably, a therapeutically effective amount is administered. As used herein, the term "therapeutically effective amount" refers to an amount that results in an improvement or remediation of the condition.

Administration

Administration of the pharmaceutical composition is by means which the agent contained therein will contact the target cell (e.g., HBC). Examples of such routes are localized and systemic, which include, without limitation parenteral, enteral, and topical administration. Parenteral administration is usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Administration can be systemic administration, or localized, as determined necessary by the skilled practitioner. Localized administration can be directed to the location of the target cells (e.g., cells of the olfactory epithelium). In one embodiment, localized administration is directed to the nasal cavity. Administration can be, for example, by nasal infusion, inhalation, injection, and any other means determined suitable by the skilled practitioner. In one embodiment, the administration is via nasal infusion (e.g., via a nasal spray formulation).

Pharmaceutical compositions and formulations for specified modes of administration, described herein are also encompassed by the present invention.

Another aspect of the present invention relates to pharmaceutical compositions for use in therapeutic methods which comprise, one or more cells described herein along with a pharmaceutically acceptable carrier or media. The pharmaceutical compositions may further comprise proliferation factors or lineage commitment factors (e.g., agents for down-modulation of p63) that act on or modulate the cells contained therein. The composition is formulated for administration to a subject in need thereof. Specific formulations will depend upon the method of administration. Suitable methods of administration are described herein.

One aspect of the invention relates to methods of treatment of diseases, disorders or injury in a subject by administration of the cells described herein. In one embodiment, a cell or population thereof, described herein, is administered to a subject. The cells of this invention can be administered, for example, by injection, transplantation or surgical operation. Administration can be in the form of a pharmaceutical composition comprising the cells.

Methods for administering cells are known in the art, and include, but are not limited to, catheter administration, systemic injection, localized injection, intravenous injection, intramuscular, intracardiac injection or parenteral administration. When administering a therapeutic composition of the present invention (e.g., a pharmaceutical composition), it will generally be formulated in a unit dosage injectable form (solution, suspension, emulsion. In one approach, activated stem cells, or differentiated cells derived therefrom, obtained in vivo or generated in vitro by the methods described herein, are implanted into a host subject. The transplantation can be autologous, such that the donor of the cells is the recipient of the transplanted cells; or the transplantation can be heterologous, such that the donor of the cells is not the recipient of the transplanted cells. Once transferred into a host, the cells are engrafted, such that they assume the function and architecture of the native host tissue.

Advantageously, cells of the invention engraft within the tissue or organ. If desired, expansion and differentiation agents can be provided prior to, during or after administration of the cells to increase, maintain, or enhance production or differentiation of the cells in vivo.

Definitions

By "isolated" is meant a material that is free to varying degrees from components which normally accompany it as found in its native state. "Isolate" denotes a degree of separation from original source or surroundings. For example, an isolated cell can be removed from an animal and placed in a culture dish or another animal. Isolated is not necessarily being removed from all other cells.

The term "isolated population" with respect to an isolated population of cells as used herein refers to a population of cells that has been taken from its natural environment (e.g., in the body) and has been removed and separated from a mixed or heterogeneous population of cells (e.g., either in the process of removal from the natural environment, or subsequence to its removal, or a combination of both). In some embodiments, an isolated population is a substantially pure population of cells as compared to the heterogeneous population from which the cells were isolated or enriched from. In some embodiments, the isolated population is an isolated population of activated cells which is a substantially pure population of activated cells as compared to a heterogeneous population of cells comprising activated cells and cells from which the activated cells were derived.

Such cells can be originally isolated from an adult or from an immature subject (e.g., ≤18 years of age, or ≤1 year of age, or ≤1 month of age, or ≤1 day from birth, or from an embryo or developing fetus).

The term "substantially pure", with respect to a particular cell population, refers to a population of cells that is at least about 50%, 60%, 70%, or 75%, preferably at least about 85%, more preferably at least about 90%, and most preferably at least about 95% pure, with respect to the cells making up a total cell population. Recast, the terms "substantially pure" or "essentially purified", with regard to a population of activated cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not activated cells or their progeny as defined by the terms herein.

As used herein, the term "activating" as used in reference to dormant stem cells (e.g., horizontal basal cells), refers to inducing a state of multipotency of the dormant cells such that they readily function as stem cells in the regeneration of adult epithelium (e.g., in the adult olfactory epithelium) as described herein. In one embodiment the activated HBC functions in the regeneration of neuronal cells.

As the term is used herein, HBC refers to HBCs of the olfactory epithelium. Activated HBCs can reconstitute the olfactory neuroepithelium, including neuronal and non-neuronal epithelial cells found therein.

Downmodulation refers to reducing the function of the protein (e.g., p63). This can be accomplished by directly inhibiting the production of functional p63 itself in the cell (e.g., by reducing gene expression or protein synthesis), or alternatively by reducing p63 function/activity. p63 function/activity can be reduced, for example by directly inhibiting the p63 protein itself or otherwise targeting that protein for degradation. As such, an agent useful in the present invention is one that inhibits p63 gene expression or protein synthesis, or inhibits p63 function or activity.

Downmodulation of p63 can also be accomplished by inhibition of an upstream factor that induced or positively regulates p63 gene expression of p63 function/activity. As such, another useful agent is an agent that inhibits or downmodulates such an upstream factor by methods that correspond to those described for p63. Such upstream factors are described herein.

Upmodulation refers to increasing the level of a functional protein, and is accomplished by methods described for downmodulation, but by instead increasing or activating gene expression or protein activity.

As used herein, the term "treating" and "treatment" and/or "palliating" refers to administering to a subject an effective amount of the agent, so as to produce activated multipotent cells (e.g., activated horizontal basal cells), or administering multipotent cells produced by the methods described herein, such that the subject has an improvement in the condition, for example, detectable beneficial or desired clinical results. For purposes of this invention, beneficial or desired clinical results include, but are not limited to, alleviation of symptoms, diminishment of extent of discomfort (i.e., not worsening) incurred by the condition, slowing of progression of the condition, amelioration or palliation of the condition, and also complete recovery from the condition.

The term "therapeutically effective amount" refers to an amount that is sufficient to effect a therapeutically or prophylactically significant reduction in a symptom associated with a disease, disorder or injury being treated, when administered to a typical subject with that condition. A therapeutically significant reduction in a symptom is, e.g. about 10%, about 20%, about 30%, about 40%, about 50%, about 60%, about 70%, about 80%, about 90%, about 100%, about 125%, about 150% or more as compared to a control or non-treated subject.

The compositions as disclosed herein can be administered in prophylatically or therapeutically effective amounts. A prophylactically effective amount means that amount necessary, at least partly, to attain the desired effect, or to delay the onset of, inhibit the progression of, or halt altogether, the onset or progression of the particular disease or disorder being treated.

Such amounts for therapy or prophylaxis will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

The term "nervous system disease" or "disease of the nervous system" refers to any condition characterized by the progressive loss of neurons, due to cell death, in the central or peripheral nervous system of a subject.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of multipotent cells include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc. . . . ), but it cannot form neurons. The term "multipotency" refers to a cell with the degree of developmental versatility that is less than totipotent and pluripotent.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "subject" includes organisms which are capable of suffering from a disease, disorder or injury, who could otherwise benefit from the administration of a compound or composition of the invention, such as human and non-human animals. The terms subject and individual are used interchangeably herein. The term "non-human animals" of the invention includes all vertebrates, including, without limitation, mammals (e.g., rodent (mice, rat, rabbit, guinea pig), primate, canine, equine, bovine, feline, porcine) and non-mammals. Non-human primates are also possible subjects. Specific subjects include, without limitation, humans, sheep, dog, cow, horses, chickens, mice, rats, hamster, rabbit, amphibians, reptiles, etc. Cells described herein can be in the context of or otherwise isolated from any such subject described herein.

The term "cell type-specific marker" refers to any molecular moiety (e.g., protein, peptide, mRNA or other RNA species, DNA, lipid, carbohydrate) whose presence in a cell indicates cell type. Typically the cell type-specific marker is either uniquely present on or in the cell type, or present at a higher level on or in a particular cell type or cell types of interest, than on or in many other cell types. In some instances a cell type specific marker is present at detectable levels only on or in a particular cell type of interest. However, it will be appreciated that useful markers need not be absolutely specific for the cell type of interest. In general, a cell type specific marker for a particular cell type is present at levels at least 3 fold greater in that cell type than in a reference population of cells. More preferably the cell type-specific marker is present at levels at least 4-5 fold, between 5-10 fold, or more than 10-fold greater than its average level of presence (e.g., expression) in a reference population. In some instances, the presence of one or more given cell type-specific markers, in the absence or otherwise reduced expression of another marker, is used to identify a particular cell type. Preferably detection or measurement of a cell type-specific marker makes it possible to distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc. In some instances, the presence of a specific combination of different molecular moiteis on or in a cell can be used as the cell type-specific marker. The marker can be present on the surface of the cell (e.g., an antigenic marker) or otherwise present within the cell. Cell type-specific markers for the various cell types are known in the art and routinely detected by conventional means.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method for activating a dormant epithelial stem cell, or population thereof, to a state of multipotency comprising, reducing the level of ΔNp63 in the cell(s).
2. The method of paragraph 1, wherein the dormant epithelial stem cell(s) is a horizontal basal cell (HBC) of the olfactory epithelium.
3. The method of any one of paragraphs 1-2, wherein reducing the level of ΔNp63 is by contacting the cell or population with an effective amount of one or more agents that downmodulate ΔNp63.
4. The method of paragraph 3, wherein the agent(s) is exogenous or endogenous to the organism in which the cell exists naturally.
5. The method of any one of paragraphs 3-4, wherein the agent(s) inhibits ΔNp63 gene expression, ΔNp63 protein synthesis, ΔNp63 protein function, ΔNp63 protein activity, or combinations thereof.
6. The method of any one of paragraphs 3-5, wherein the agent(s) is an RNAi.
7. The method of any one of paragraphs 3-6, wherein the agent(s) is a micro RNA.
8. The method of paragraph 7, wherein the microRNA is micro RNA 203.
9. The method of paragraph 5, wherein the one or more agents is selected from the group consisting of a chemical, small molecule, nucleic acid sequence, nucleic acid analogue, protein, peptide, aptamer, antibody or fragment thereof, and combinations thereof.
10. The method of any one of paragraphs 1-9, wherein the cell(s) is a mammalian cell.
11. The method of paragraph 10, wherein the cell(s) is a human cell.
12. The method of any one of paragraphs 1-10, wherein the cell(s) is in vitro or in vivo.
13. The method of any one of paragraphs 1-10, wherein the cell(s) is in vivo, and contacting is by administering the agent(s) in the form of a pharmaceutical composition to a subject to thereby contact the cell(s).
14. A method for treating olfactory dysfunction in a subject, comprising activating HBCs of the subject by reducing the level of ΔNp63 in one or more HBCs of the subject, to thereby treat the olfactory dysfunction.
15. The method of paragraph 14, wherein reducing the level of ΔNp63 is by administering a therapeutically effective amount of a pharmaceutical composition that comprises one or more agents that downmodulate ΔNp63, to the subject, to thereby contact the agent with the HBCs.
16. The method of paragraph 15, wherein the agent(s) inhibits ΔNp63 gene expression, ΔNp63 protein synthesis, ΔNp63 protein function, ΔNp63 protein activity, or combinations thereof.
17. The method of any one of paragraphs 15-16, wherein the agent(s) is an RNAi.
18. The method of any one of paragraphs 15-17, wherein the agent(s) is a micro RNA.
19. The method of paragraph 18, wherein the microRNA is micro RNA 203.
20. The method of paragraph 15, wherein the one or more agents is selected from the group consisting of a chemical, small molecule, nucleic acid sequence, nucleic acid analogue, protein, peptide, aptamer, antibody or fragment thereof, and combinations thereof.
21. The method of any one of paragraphs 14-20, wherein the subject is a mammal.
22. The method of paragraph 21, wherein the subject is a human.
23. The method of paragraph 14 wherein the HBC is in vitro, and implanted into the subject following activation.
24. The method of any one of paragraphs 14-23, wherein the olfactory dysfunction is anosmia or hyposmia.
25. The method of any one of paragraphs 14-23, wherein the olfactory dysfunction is due to the degeneration of peripheral neurons in the olfactory epithelium of the subject.
26. The method of any one of paragraphs 14-25, wherein the olfactory dysfunction is due to age.
27. The method of any one of paragraphs 14-25, wherein the olfactory dysfunction is due to injury.
28. The method of any one of paragraphs 14-25, wherein the olfactory dysfunction is due to disease.
29. The method of any one of paragraphs 14-28, wherein administration is localized.
30. The method of any one of paragraphs 14-29, wherein administration is via nasal infusion.
31. An isolated activated horizontal basal cell (HBCs) or population thereof.
32. The isolated cell or population thereof of paragraph 31, that is mammalian.
33. The isolated cell or population thereof of paragraph 32, that is human.
34. The isolated cell or population thereof of any one of paragraphs 31-33, that exhibits reduced levels of ΔNp63, as compared to non-activated HBCs.
35. The isolated cell or population thereof of any one of paragraphs 31-33, that exhibits reduced expression of ΔNp63, as compared to non-activated HBCs.
36. The isolated cell or population thereof of any one of paragraphs 34 or 35, wherein the reduced expression and/or reduced levels of ΔNp63 results from contacting the cell or population with an effective amount of one or more exogenous agents that downmodulates ΔNp63.
37. The isolated cell or population thereof of paragraph 36, wherein the exogenous agent(s) inhibits ΔNp63 gene expression, ΔNp63 protein synthesis, ΔNp63 protein function, ΔNp63 protein activity, or combinations thereof.
38. The isolated cell or population thereof of any one of paragraphs 36-37, wherein the agent(s) is an RNAi.
39. The isolated cell or population thereof of any one of paragraphs 36-38, wherein the agent(s) is a micro RNA.
40. The isolated cell or population thereof of paragraph 39, wherein the microRNA is micro RNA 203.

The invention is further illustrated by the following examples, which should not be construed as further limiting.

EXAMPLES

Example 1

Throughout this example, italics designate gene or genotype and CAPS designate proteins.

Figure 1B:
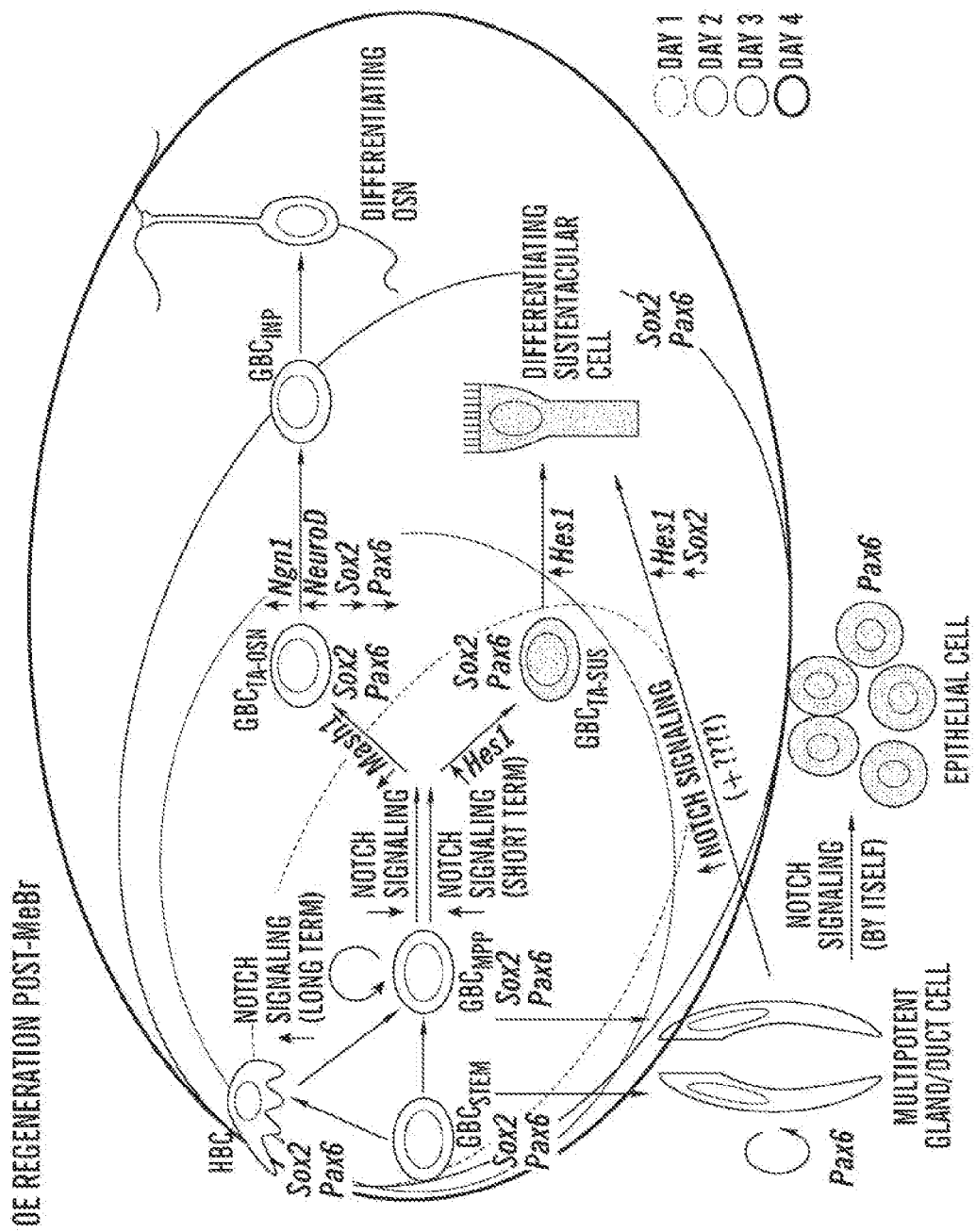

The capacity of the olfactory epithelium (OE) to recover after injury and maintain life-long sensory function depends on the maintenance and the regulated activation of the neurocompetent stem and progenitor cells of the epithelium. Conversely, depletion and dysregulation of olfactory stem and progenitor cells are both causes of sensory dysfunction. Both horizontal basal cells (HBCs) and globose basal cells (GBCs) function as multipotent progenitors in adult OE and can give rise to the full range of epithelial cell types (FIGS. 1A-1B). HBCs may be a "reserve" stem cell, since HBCs from normal adult OE are not immediately multipotent following transplantation. Instead, based on prior work, HBCs require in situ "activation" by the lesioned environment before they can engraft and function as multipotent progenitors. The transcription factor ΔNp63, a member of the p53 family, appears to be critical for determining whether HBCs are activated or not. HBC differentiation from GBCs, which takes place during peri- and postnatal development, requires expression of ΔNp63. Conversely, HBC activation by OE injury is accompanied by a down-regulation of p63, release of the activated cells from the basal lamina, and transdifferentiation into GBCs as well as the multiple other epithelial cell types. Subsequently, quiescent HBCs re-emerge as p63 expression is renewed. These data strongly support the hypothesis that p63 plays a key role in the activation of HBCs after lesion and in their eventual return to dormancy.

Aberrations of HBC activation also factor into olfactory pathophysiology. For example, the epithelium of an- or hyposmic humans and mice can remain olfactory—having a full complement of sustentacular (Sus) cells—but aneuronal because of neurogenic failure. HBCs persistin the aneuronal and non-neurogenic epithelium, but GBCs are gone. Thus, HBCs do not activate under these circumstances and are not functioning as stem cells, but presumably still have the potential to do so. Taken together, the three lines of experimentation described in Example 1 will clarify major aspects of the process of HBC activation and invigorate the development of potential strategies for therapeutic intervention to accomplish epithelial repair.

The life-long capacity of the OE to repair itself implies and requires the persistence of neurocompetent stem cells. Nonetheless, olfactory function becomes compromised quite commonly due to aging and/or epithelial injury[1], [2]. Olfactory dysfunction accompanies histological abnormalities of the epithelium caused by destruction or dysregulation of olfactory stem cells, based on extrapolation from animal models of epithelial pathology[3][4-8]. Thus, a deeper understanding of the identity and regulation of olfactory stem cells may indicate targets for therapeutic intervention in dysosmic patients.

Two cell types have been put forward as candidate stem cells: GBCs and HBCs. GBCs are unique to the OE and share similarities with the cells of the embryonic olfactory placode and pit. HBCs closely resemble the basal cell population of many other epithelia including the lining of the respiratory tree. Neither satisfies fully the criteria expected of stem cells, which include multipotency and self-renewal, and result in the ongoing, long-term contributions of single cells to the tissue[9], [10].

The GBC population is phenotypically heterogeneous. Different molecular categories of GBCs can be identified on the basis of transcription factor (TF) expression, including Sox2, Pax6, and several basic helix-loop-helix (bHLH) TFs[11-13][14][15]. Such molecular categories correspond to discrete stages in GBC progression as shown by the absence of TF overlap and by TF expression as a function of developmental age, time after MeBr lesion, and genetic epistasis (FIGS. 1A-1B) [11-13], [15-17]. Evidence that a subset of GBCs are stem cells includes their capacity to regenerate all of the cell types of the epithelium (even respiratory epithelium). This has been demonstrated by 1) transplantation of FACS-purified GBCs harvested from OE, which are immediately multipotent, independent of epithelial status (whether lesioned or not)[18], [19]; 2) lineage tracing in situ by retroviral transduction[20]; and 3) the identification of cells with an molecular profile that is intermediate between GBCs and their differentiating progeny[21], [22]. It is important to emphasize that GBCs do not require some type of activation in situ in order to manifest their multipotency following engraftment. Moreover, some among the GBCs are label-retaining, i.e., they remain mitotically quiescent and persistently labeled by the incorporation of thymidine analogues for weeks at a time[23], a hallmark of stem cells in several other tissues.

Evidence that HBCs are stem cells derives from an analogous set of findings, including lineage tracing by cell type-specific genetic recombination in the lesioned epithelium[24], [25], with one key exception—FACS-purified HBCs harvested from the normal OE show no evidence of immediate multipotency following transplantation[19], [26]. Similarly, HBCs in the unlesioned OE only rarely give rise to cells other than themselves[24], [25] These features combined with their latepperi- and postnatal emergence suggest that HBCs are reserve stem cells that are set aside around birth as insurance against direct epithelial damage and must be activated to multipotency by such damage. The existence of two or more stem cell populations is not atypical and has been demonstrated for the subventricular zone of the CNS[27], the skin[28], the gut[10], and the respiratory epithelium lining the airway[29].

Given the existence of two putative stem cell populations, the prevalence of olfactory dysfunction is even more discouraging. atchy replacement of OE by respiratory epithelium in humans (a kind of injury-induced metaplasia) has been observed[4], [30], [31], evidently because both types of neurocompetent stem cells have been completely eliminated by epithelial injury. Observations following severe epithelial injury in experimental animals support that model of pathophysiological process[5], [8]. However, a second kind of epithelial pathology consequent to stem cell dysfunction is perhaps as frequent and potentially more amenable to therapeutic intervention. The OE in some individuals becomes aneuronal, particularly as a function of age, yet remains identifiably olfactory with a full complement of Sus cells[4], [32]. On close examination, one can identify HBCs flattened against the basal lamina, but GBCs and neurons are absent. In these cases, neurogenesis looks to be wiped out, and yet the HBCs are not participating in any kind of recovery. In this setting, HBCs have failed to activate and remain quiescent. A similar neurogenic burn-out/failure occurs over time in mice made transgenic for OMP-driven SV40 large T antigen[33]. Here, too, the epithelium is aneuronal, but appears quiescent. Given that HBC multipotency is triggered robustly in the MeBr-lesioned OE and occasionally in the predominantly neurogenic environment of the normal or post-bulbectomy OE, HBCs ought to activate in an aneuronal epithelium, i.e., to make GBCs (which then make neurons), but they do not. The critical questions are why not and what to do about it.

The lack of knowledge of the regulatory cues and the cellular mechanisms that activate HBCs prevents the use of their persistence in the non-neurogenic OE. For example, given their activation by injury if left alone in situ, why don't HBCs behave as multipotent immediately after transplantation into the lesioned environment? What then is known regarding HBC activation and how it occurs? It is not an artifact of the transplantation assay, as it has been shown that HBCs harvested from OE 2 days post-MeBr do engraft, and many of the clones they generate are complex and composed of neurons, basal cells, and Sus cells26.

Summarized experimental results: Fluorescence microscopy and FACS profiling of expression of CD54, CK14 in HBCs from OE demonstrated that transplanted HBCs from MeBr-lesioned OE can be multipotent, while those from normal OE do not engraft. CD54 (+) cells from lesioned OE were CK14 (+), but their processes were truncated as compared to normal, which may correlate with activation. CD54 (−) cells from normal OE were multipotent, unlike their HBC counterparts. CD54 (+) cells from lesioned OE can produce HBC-only clones. CD54 (+) cells from lesioned OE could make complex clones, suggesting that the HBCs function as multipotent progenitors after transplant, if they were activated in situ.

Thus, the engraftment failure of HBCs represents an inherent limitation on their differentiative capacity. These data suggest that some set of cues from the lesioned environment must work on the HBCs for a period of time in situ so that their multipotency becomes activated and begins to play out. That HBCs need to activate to become multipotent is likely to be relevant to their quiescence in the aneuronal OE of patients and transgenic mouse models of neurogenic failure. Accordingly, knowing what HBC activation is, and how it occurs, will be key to understanding how to manipulate it for therapeutic purposes.

To that end, investigation has proceeded into the role of p63, a member of the p53 family of TFs, in the developmental emergence of HBCs and in the cycle of lesion-induced activation-dormancy34. p63 is expressed selectively in K5/K14 basal keratinocytes, and p63 knockout prevents the formation of a stratified epidermis35-37. p63 has 6 isoforms38. The two variants of the N-terminal sequence are driven from alternate promoters. TAp63 includes, while ΔNp63 omits, the N-terminal transactivation domain. The 3 variants at the C-terminus (α, β, γ) are derived by alternative splicing but their biological significance is incompletely understood as the variants are equally potent in most assays. The truncated isoform—ΔNp63—is the relevant one for epithelial development. For example, ΔNp63, but not TAp63, can rescue the p63 (−/−) epidermal phenotype and regulates a large cadre of genes that figure in the structure and function of K5/K14 basal cells. Nonetheless, it has been a matter of some debate whether p63 is functioning as a master regulator of stem cell function in the skin, per se, or responsible for the differentiation of basal cells that are, in turn, stem cells for other, p63-independent reasons39, 40.

It has been shown that the ΔNp63 isoform is also the predominant one in the adult OE, where it is limited to HBCs and detectable in 99+% of them 34. (In the following sections, "p63" is used to refer to the ΔN-form.)

Summarized experimeintal results: Fluorescence microscopy imaging was performed to visualize p63 and ΔNp63 expression, K14 and CK14 expression, Ascl1, K18 and Tuj1. This analysis demonstrated that p63 forecasts and is required for HBC differentiation. Cells at E14 were analyzed. p63 staining marked a subset of GBC-like progenitors that were K14(−). By P3 p63(+) cells expressed CK14. Some p63(+)/CK14(+) cells were already fully flattened HBCs, while others just touch the basal lamina. At E14, Ascl1 marked some p63(+) HBC progenitors. Knock-out of p63 aborted HBC differentiation WT and KO OE. p63 KO did not block other cell types, i.e., Tuj1(+) OSNs and CK18(+) Sus cells. p63 KO OE contains Sox9(+) D/G structures, but some had not yet penetrated the basal lamina. Both mature and immature OSNs formed in the basal KO. Analysis of the ΔNp63-GFP knock-in was also performed by detection of GFP and cK18. Cells that turned on the mutant p63 locus and could not make HBCs survived and formed Sus cells and D/G cells.

In the perinatal and postnatal OE it was found that the expression of p63 in GBCs (i.e., cells expressing GBC-specific markers and situated well above the basal lamina) anticipates their differentiation into HBCs. Such p63 (+) GBCs first co-express the bHLH-TFs MASH1/ASCL1, then HES1 and finally acquire other HBC-specific features, including K5/K14 and CD54 expression and descent toward/attachment to the basal lamina. Indeed, the differentiation of HBCs is completely dependent upon p63; when p63 is knocked out, HBCs do not form and the cells that attempt to express p63 carry on to become Sus cells and gland/duct cells. In striking contrast to the skin, p63 knockout does not interfere with the differentiation of the other OE cell types nor with the initial assembly of the OE34.

p63 also looks to play a role in the activation of HBCs following MeBr lesion34.

Summarized experimental results: Fluorescent microscopy was performed to visualize p63 and CK14 in normal OE and meBr lesioned OE. This analysis showed that p63 regulates HBC activation in adult OE. FIGS. 5A-5D show p63 in green and CK14 in red. In the normal OE the vast majority of HBCs were p63 (+). The rare HBCs that were not p63(+), may have been activating to multipotency. 1 day after MeBr lesion, most CK14(+) HBCs no longer stained for p63. 2 days after MeBr lesion, the basal-most CK14(+) cells had regained expression of p63, while more apical CK14(+) cells remain p63(−). Cells transduced with the MIG vector expressing only GFP, were multipotent. Cells transduced with DNp63, had been forced to become/remain HBCs.

Figure 2A:
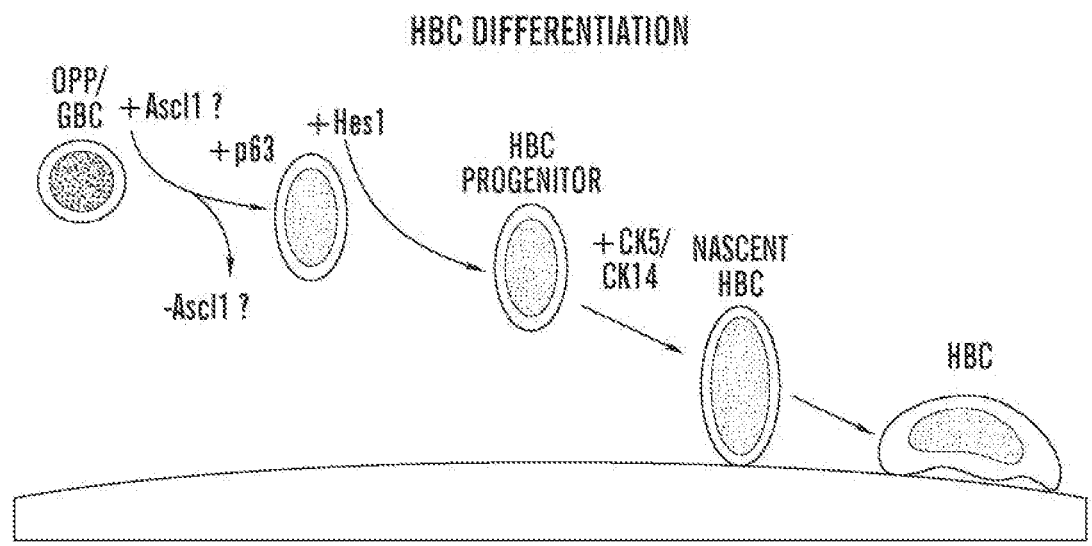
FIG. 2A-FIG. 2B depict models of HBC regulation.
Figure 2B:
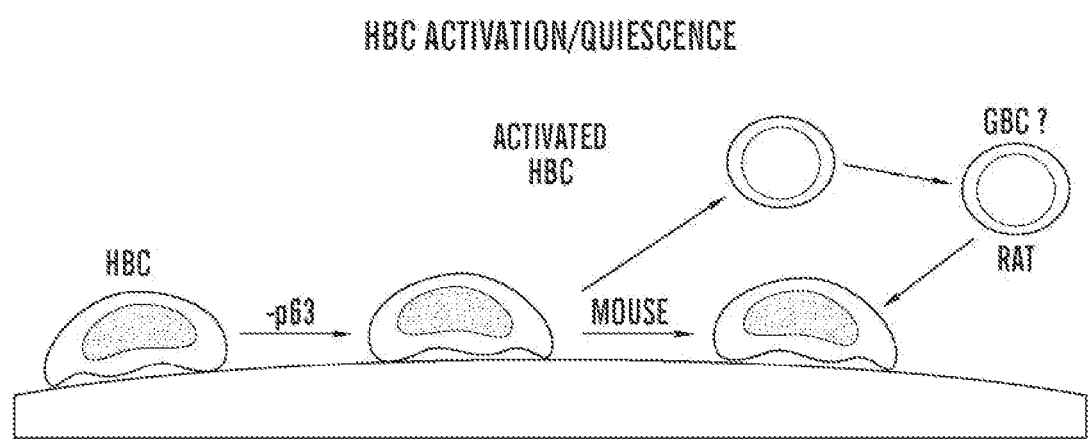
Figure 3:
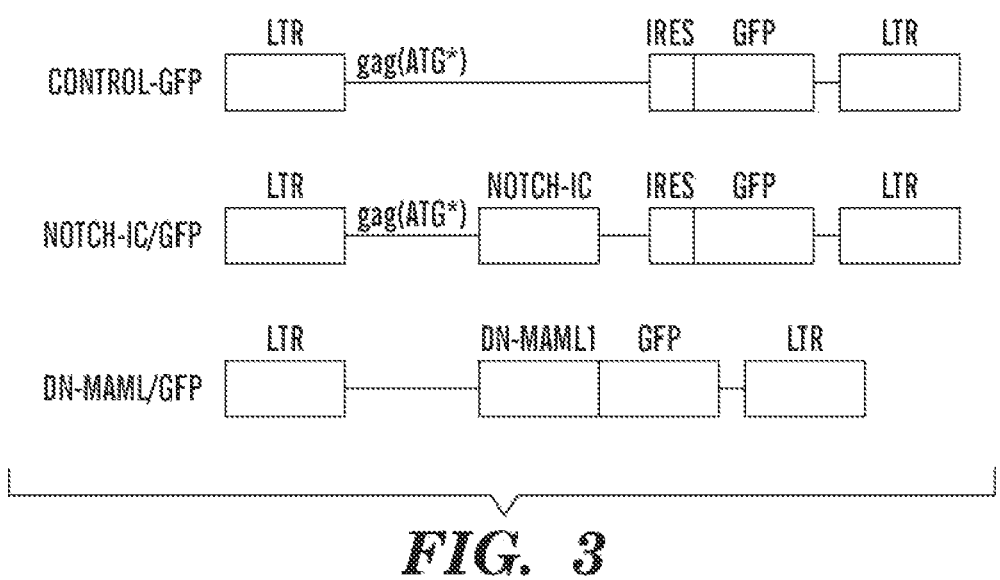
FIG. 3 is a schematic of the RV constructs used in the experiments herein.

In mice, it was shown that p63 levels fall as HBCs begin to proliferate and accumulate immediately after lesion. There are two or more layers of K5/CD54 (+) cells by the second day after lesion, but p63 is no longer evident in the cells of the uppermost layer (FIGS. 2A-2B). The cells of these upper strata, in turn, lose detectable HBC markers within the next day or so of the recovery period (and presumably give rise to the complex clones of Sus cells, OSNs, basal cells and duct/gland cells that have been shown by lineage tracing). In rats, HBCs disappear temporarily from the ventral OE, and their re-emergence at a later point during epithelial reassembly recapitulates the developmental sequence (FIGS. 2A-2B).

Summarized Experimental Results: Fluorescent microscopy was performed to detect Notch1 and CK14 in GBCs and HBCs in normal OE. This analysis demonstrated that Notch 1 regulates cell fate during OE regeneration. RV transduction with NICD made large colonies by comparison with GFP-only. Following transduction with the DNMAML construct, only OSNs and basal cells were seen. Following transduction with NICD, Type I clones of Sus-like cells or Type II with D/G-like cells were present.

The observations on epithelial reconstitution, taken together with the developmental dependence on p63, suggest that regulation of p63 is part and parcel of activating HBCs and returning them to dormancy.

p63 is a high value target for therapeutic intervention. p63 is known to be translationally regulated by microRNA miR-203 in several tissues, including skin, where topical application of the miRdiminishes levels of p6341, suggesting that direct application to the OE by intranasal infusion might also be effective. Moreover, in skin and other tissues, p63 is regulated by the Notch42-45 and Wnt44-46 signal transduction pathways, which also operate in the OE. Signaling via these pathways can be up- or down-regulated by small molecule activators and inhibitors. Given the availability of reagents and transgenic/gene-targeted mice, the participation of these two critical pathways in olfactory epithelial assembly post-injury, and the likely role of p63, it is worth our while to manipulate Notch and Wnt signaling in the normal OE and during its reconstitution.

Without a doubt, the establishment of, and interchange between, multiple stem cell types is of interest to investigators studying either neural or non-neural stem cells, since the laying down of two or more types of stem cells is a general phenomenon10, 27-29. Results of the experiments described herein indicate an innovative way of thinking about therapeutic strategies for clinical olfactory dysfunction. At present, there is no treatment for sensorineural forms of dysosmia, other than the radical extirpation of the mucosa in patients with disabling phantosmias47, 48. The persistence of putative HBC stem cells in aneuronal/non-neurogenic OE presents an opportunity for an alternate approach, namely regulated reactivation of HBCs, which may be less invasive—more biologic—and more effective than approaches that rely solely on transplantation and engraftment of stem and progenitor cells. Given the involvement of the Notch and Wnt signaling, the reactivation of HBCs might potentially be accomplished by small molecule effectors of these pathways.

Previous Analysis. The population of GBCs was analyzed and subdivided using two primary approaches: first, double- and triple-antibody immunohistochemistry (IHC); second, lineage tracing using genetic recombination. With regard to the molecular characterization of different GBC subsets, a detailed analysis was performed of the pattern of expression of the TFs Sox2 and Pax6 by comparison with several of the proneurogenic bHLH TFs (Guo et al., 2010)15. These data plus other published results clarified the division of the GBC population into subsets and the transitions between them (FIG. 1). Based on these data, it was surmised that multipotent GBCs (GBCMPP) are characterized by the joint expression of Sox2 and Pax6, upstream of and unaccompanied by either MASH1/ASCL1 or NEUROG1 or NEUROD1 expression. Some of these upstream GBCs express the cyclin-dependant kinase inhibitor (CDKI) p27Kip1, suggesting that they are not actively proliferating15. Indeed, have confirmed the existence of quiescent, label-retaining, EM-verified, putative stem-like GBCs that retain incorporated BrdU/EdU for a month after the tag is administered either postnatally or after MeBr lesion has been confirmed23. Expression of Sox2 and Pax6 persists in MASH1/ASCL1 (+), putatively transit-amplifying GBCs but declines to undetectable levels in proliferating NeuroD1 and NEUROG1 (+) neuron-producing GBCs 15. The pattern of expression suggests that Sox2 and Pax6 play roles at multiple stages in the GBC lineage. This surmise is supported by using retroviral transduction to over-express the TFs or to knock-out floxed Sox2, which suggests that Sox2 suppresses neurogenesis when expressed in upstream multipotent progenitors but enhances neurogenesis when acting on the MASH1- and NEUROD1-expressing GBCs 49.

These data suggest that the neuronal progenitors pass through a phase of expressing NeuroD1, and, in a second approach, out genetic recombination-based lineage tracing was performed with a NeuroD1-Cre BAC transgenic line to prove virtually all of the OSNs of the main OE, all of the neurons of the vomeronasal and nasal septal organs, and scattered, unidentified cells embedded in the respiratory epithelium derived from a NeuroD1-expressing progenitor (Packard et al., 2011)17. In addition, it was shown that the NEUROD1(+) and ASCL1/MASH1(+) populations are completely non-overlapping and that each marks a discrete stage in the progression of the GBCs towards the production of OSNs (FIGS. 1A-1B).

With regard to the question of the functional capacity of the different categories of basal cells, two approaches were taken. The first utilized a transplant assay. HBCs from the normal, i.e., purely neurogenic, epithelium did not engraft and did not give rise to epithelial cells19, 26. In contrast, the CD54(−) cells from normal epithelium, which population includes GBCs and other cell types, generate clones that are usually composed of multiple cell types, as expected. In contrast, HBCs from the 2-day post-MeBr-lesioned OE engrafted well and produced clones that were often complex in composition26, like GBC transplants 19 and like the in situ analysis of HBC lineage in the lesioned OE24, 25. These data are interpreted as most consistent with a requirement for HBCs to be activated in situ in order for them to engraft and function as multipotent progenitors. Ultimately, the criterion of transplantability is the relevant one for any translational consideration.

For the different GBC subtypes, the same kind of FACS-transplant strategy was originally proposed to look at functional capacity and reversibility. However, the development of two kinds of 3-dimensional (3-D) culture systems led to a different approach. Cells from the OE—whether neonatal, normal adult, or post-MeBr-lesioned—form complex 3-D epithelioid structures (spheres) when cultured on inserts at the air-media interface (Jang et al., 2008) 50 or as free-floating spheres (Krolewski et al., 2011)51. Cells maintained as spheres in culture were able to engraft and function as multipotent, in close alignment with the success in transplanting the cells acutely after harvest, and in stark contrast with olfactory cells grown in adherent 2-D cultures which do not engraft properly. These data suggest that sphere formation is a biomarker for engraftability and the maintenance of multipotency. Further evidence for that conclusion comes from the correlation between failure of HBCs from normal OE to form spheres on their own and their inability to engraft after acute transplantation 50, 51. In contrast, Sox2(+) GBCs (including both upstream/ASCL1 (−) and downstream/ASCL1 (+) subtypes) are able both to form spheres and to engraft51. In addition, the spherogenicity of NEUROG1-eGFP-expressing GBCs was tested, and it was found that they were not able to form spheres51. On this basis, it is predicted that the NEUROG1(+) GBCs will not be multipotent if transplanted, which rules out their ability to reverse to multipotency. Development is also underway of an Ascl1/Mash1 targeted mutation mouse line (using a knock-in strategy employing E2A or skip sequences rather than IRES sequences to maximize insert expression) that can be used for lineage tracing and FACS isolation in a way that current transgenic lines cannot.

The role of Notch signaling in determining the fate of progeny in the adult OE was investigated by a combination of IHC analysis and retroviral transduction (Zhen Guo, 2008, Ph.D. thesis; Guo et al.)52. Notch1 appears to be the dominant form expressed by basal cells; anti-Notch1 antibodies label a population of GBCs strongly and a scattered group of HBCs less well in both rats and mice (FIGS. 7A-7I). Of the Notch1 GBCs, some are Sox2 (+) but ASCL1(−), indicating that they are upstream, while others are also labeled by the expression of GFP from the NEUROG1 BAC transgenic line; the latter are proliferating, immediate neuronal progenitors (INPs). Biphasic Notch1 expression is not unusual and indicates a complex role in cellular differentiation. The assignment of Notch1 to GBCs and HBCs has been confirmed by microarray analyses of FACS-isolated cell types carried out using Illumina MouseWG-6 v2.0 bead arrays at the Keck Facility at Yale (Richard C. Krolewski, 2011, PhD thesis)53. Moreover, the other Notch receptors were seen not to be enriched in HBCs and GBCs.

In order to manipulate Notch signal transduction, retroviral vectors encoding the constitutively active intracellular domain of Notch1 (NICD-IRES-eGFP) and the dominant-negative version of the essential NICD co-factor Mastermind-Like (DN-MAML-IRES-GFP), which suppresses Notch signaling52, 54 were used. It is important to note that GBCs are much more likely to be the target cells for retroviral transduction than HBCs in the lesioned rat OE, because the vast majority of proliferating cells that sit exposed at the epithelial surface have the characteristics of GBCs (Sox2/Pax6 expression in the absence of HBC markers). Infusion of the NICD vector 1-day after MeBr resulted in two kinds of clones: Type I clones are composed of piled up Sus-like cells that are proliferating at an enhanced rate (FIGS. 7A-7I); Type II clones are composed of nests of epithelial cells that share the characteristics of duct/gland cells. In contrast with eGFP-alone vector, no OSNs are found within Type I or Type II clones. Infusion of the DN-MAML vector has the opposite effect (FIGS. 7A-7I): clones are only comprised of OSNs and GBC-like basal cells. Thus, Notch signaling aborts neuronal differentiation, which might be expected since Hes1, a canonical Notch1 target gene, is upregulated in GBCs that are differentiating into Sus cells in the post-lesioned OE. Conversely, blocking Notch signaling aborts differentiation of non-neuronal cell types. However, Notch is acting more like a permissive cue, since it is incapable of driving Sus cell differentiation on its own following direct injection into the purely neurogenic OE, even though it blocks neuronal differentiation.

That interpretation is also supported by the recent re-examination of the OE of Ascl1/Mash1 knockout animals (Krolewski et al.,)55. In the absence of neurogenesis, there are no Notch1(+) GBCs in the embryonic OE, and the level of the canonical Notch target HES1 in individual Sus cells of the knockout varies from markedly reduced to undetectable, suggesting that Notch signaling is not required for Sus cell differentiation, but rather suppression of neuronal differentiation. In reaction to aborted neurogenesis, the OE has regulated its expression of Notch1 such that any possibility that Notch signaling might interfere with neuronal differentiation has been down-regulated/eliminated.

Signaling via the Notch pathway is often mutually antagonistic to signaling via the Wnt pathway. Research indicates that the Wnt pathway is, indeed, in a position to operate in opposition to Notch signaling (Wang et al., 2011)56. Multiple Wnts and Wnt pathway components are found in the OE, most significantly Wnt3a. Moreover, enhanced β-catenin activation of the Top-eGFP reporter construct is associated with enhanced neurogenesis in vivo and in vitro. In sum, Notch and Wnt signaling have "opportunity and motive" for regulating progenitor cell activation and differentiation in opposite directions.

Proposed Experiments:
1. The Role of p63 in the Cycle of Activation-Dormancy of the HBCs of the Adult OE.

Does eliminating p63 expression in HBCs under purely neurogenic circumstances (i.e., in normal or bulbectomized mice) lead to activation and multipotency? Conversely, does sustained up-regulation of p63 prevent multipotency? In order to investigate these questions, knock-outs of p63 in HBCs of normal and bulbectomized OE can be created by conditional recombination in trigenic K5-CreER$^{T2}$; floxed (p63)/floxed(p63); ROSA26-floxed(stop)LacZ mice, and the composition of the resultant clones determined. Additionally, p63 can be overexpressed in HBCs immediately prior to MeBr lesion as well as HBCs in purely neurogenic OE via Tg(K5-Tet-off driver); Tg(tetop-HA-ΔNp63) mice. It is expected that p63 knockout will cause HBCs to differentiate into GBCs and give rise to other types of cells; a rare event in the neurogenic OE. Conversely, it is expected that over-expression of p63 will prevent HBCs from reaching multipotency following MeBr lesion and will eliminate those rare examples of activation to multipotency in the neurogenic OE. In light of these likely effects, the down-regulation of p63 becomes an exciting candidate target for reactivating dormant HBCs and ameliorating dysfunction.

Purpose. To prove that the TF p63 is key to the regulation of HBC progenitor activity by showing that elimination of p63 by gene knockout shifts HBCs to multipotency while expression of p63 from a tetracycline-regulated transgene maintains an HBC-restricted fate. Available lines of transgenic and gene-targeted mice will be used to both to knock-out p63 by recombination only in HBCs, on the one hand, and to maintain high level expression of p63 in HBCs independent of epithelial demand (in normal, or MeBr-lesioned, or post-bulbectomy OE), on the other.

Underlying Rationale. Activation of HBCs to multipotency is a response to some signal or set of signals from the environment of the lesioned OE. The external signals regulating multipotency are likely to be complex and multiple. However, the nexus/tipping point for regulating the behavior of the HBCs looks to be expressing vs. suppressing p63. The reasoning follows from the correlation between p63 expression and what HBCs are capable of doing as progenitors. In addition, preliminary data indicate that retroviral transduction with p63 1-day after MeBr lesion has the effect of driving the progeny of the p63-transduced progenitors to remain/become HBCs (FIG. 2A-2B). It is likely that both proliferating HBCs and residual GBCs are being transduced under these conditions, but the uncertainty regarding the targeted cell types, and the limitations on how and when retroviral transduction can be accomplished push us to adopt a genetic approach.

The linchpin role of p63 is demonstrated by the vast array of its putative biological functions. The three independent p63 (−/−) mutant mouse lines all display craniofacial abnormalities, limb agenesis, and aborted stratification of skin and other epithelia3736. The mutant pups lack K5 (+)/K14 (+) basal keratinocytes, HBCs, and basal cells in other epithelia indicating that p63 is an essential factor in establishing, and possibly maintaining these stem/progenitor cells. p63 has been shown to directly regulate expression of a number of basal cell markers such as K5/K14, cell adhesion proteins, cell differentiation programs, and developmental signaling pathways such as Bmp, Notch, FGF, and Wnt65-69. Indeed, ChIP-on-chip and microarray data of a human cervical carcinoma line reveal a staggering number of genes potentially regulated by p63 suggesting that it is indeed serving as a master switch during the differentiation of stratified epithelia70. Conversely, diminution of p63 levels by miRs causes the basal cells of skin to lose their basal character/"stemness" and begin terminal differentiation into upper layer skin cells41. Finally, in addition to epidermal and limb development p63 is implicated in progenitor cell regulation of multiple other epithelial systems including breast43, 71, prostate44, 72, 73, and thymus74. Taken together, the constellation of effects observed with up- or down-regulation of p63 suggest that it is a master regulator of the basal cells of many epithelia.

Design. The experiments in this Example have the same general design: using readily available lines of transgenic or targeted mutant mice to up-regulate/over-express a targeted signaling pathway or TF vs. eliminate the corresponding gene by recombination (Table 1). A conditional approach can be employed that will limit these otherwise embryonic lethal mutations to HBCs and at a time of our choosing. For the knockouts of p63, Notch1, and β-catenin genes, for the activation of β-catenin, and for the expression of NICD selectively in HBCs, we will be exploiting the Tg(K5-CreERT2) driver line developed by Chambon, which was has been used successfully to achieve conditional, HBC-specific recombination24. With this line, the Cre recombinase is expressed only in HBCs where it is confined to the cytoplasm and activated upon tamoxifen administration. With the binding of tamoxifen to the mutated estrogen receptor, the Cre is transported into the nucleus where genes (or parts thereof) that are flanked with LoxP sites undergo recombination. Since tamoxifen-induction is insufficient to activate recombination in all HBCs24, a LacZCre reporter line will be used to trance the progeny of those cells where there was nuclear translocation of Cre (Table 1). Their progeny will be classified by IHC analysis using our standard battery of cell type-specific markers (Table 2). In all cases the results of conditional overexpression or knock-out will be compared with wild-type or mice that are heterozygous at the targeted locus. The use of conditional recombination to achieve temporal and spatial gene regulation is a well-accepted approach and has been successful in defining gene function in multiple tissues and many genes.

Figure 4:
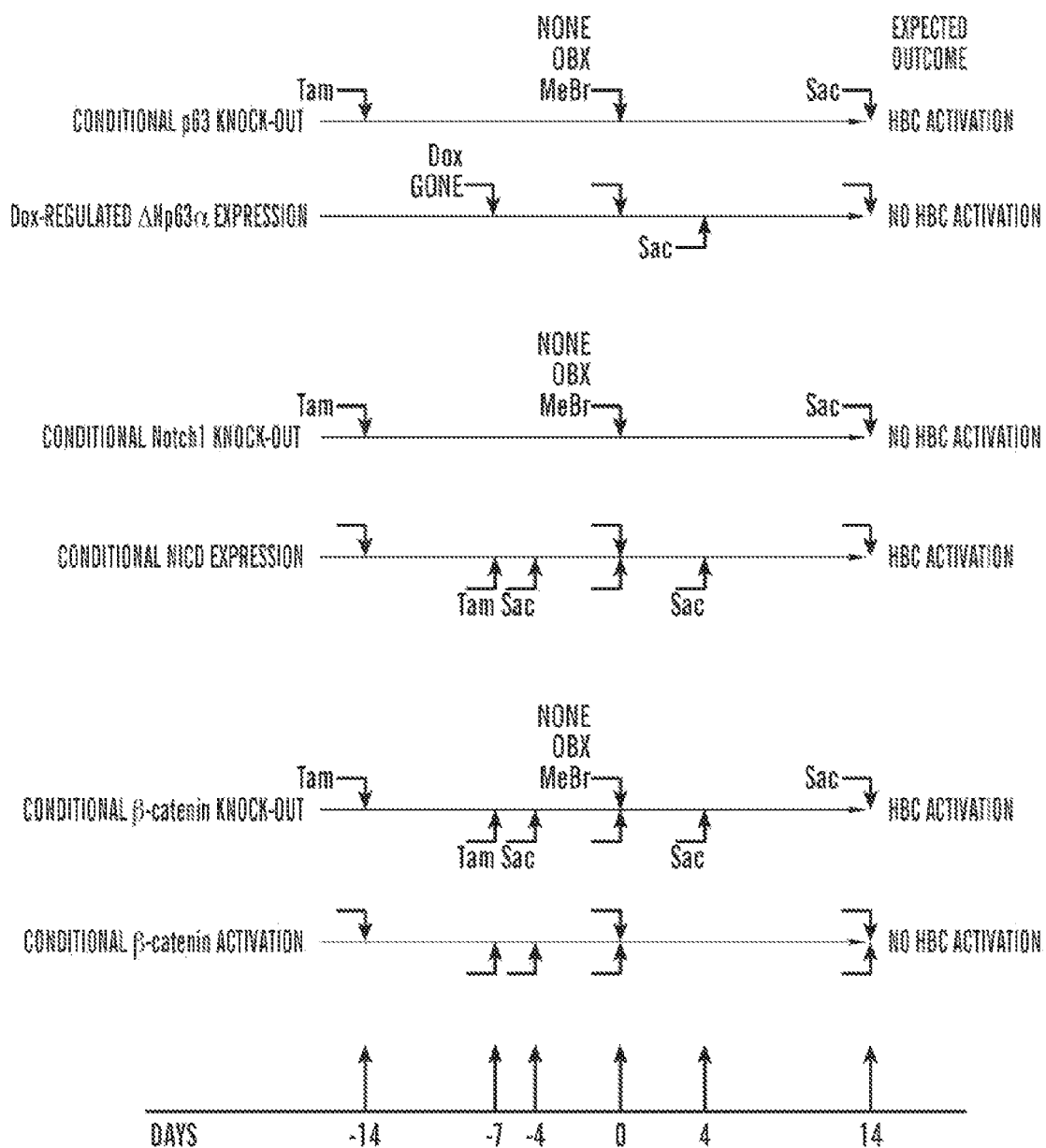
FIG. 4 depicts the experimental design for Example 1. Arrows above the lines indicate the timing of the standard manipulations. Arrows below the lines designate alternative assessments, included to determine the short term effects of disrupted signaling, which may be different, given the strength of the Notch and Wnt pathways.

For conditional HBC knockout of p63, breed a trigenic line of mice will be bread beginning with three available independent lines: one in which most of the DNA-binding domain (DBD) of p63 (exons 5-7) is flanked by LoxP sites, the K5-CreER[72] driver mice, and the R26R(LacZ)Cre-reporter line (Table 1)[75]. The mice will have the following genotype: K5-CreER[72]; fl(p63DBD)/fl(p63 DBD); R26R(LacZ). The two control lines will be fl(p63 DBD)/+ vs.+/+ at the p63 locus to rule out any effect of p63 heterozygosity. Gene recombination will be elicited by injection of tamoxifen according to the following schedules: 1) 2 or 4 weeks before tissue harvest without additional manipulation (normal OE); 2) 2 weeks before undergoing olfactory bulb ablation with tissue harvest 2 weeks after surgery (post-bulbectomy OE); 3) 2 weeks before exposure to MeBr with tissue harvest 2 weeks later (post-MeBr OE) (FIG. 4).

For unregulated static expression of p63, Tet-Off control of p63 expression will be used (Table 1). This approach takes advantage of a different K5-driver line, Glick's Tg(K5-tTA) line[76], which has been used to good effect to drive expression of HA-tagged-ΔNp63α in the skin of bigenic Tg(K5-tTA); Tg(tetop-HA-ΔNp63αmice[77]. In this line, the tet-transactivator (tTA) is expressed in HBCs. In the presence of doxycycline (Dox) tTA is unable to drive expression of genes downstream of the tet-operator/response element (TetO or TRE). Thus, the test mice will be trigenicTg(K5-tTA); Tg(tetop-HA—ΔNp63α); Tg(tetop-LacZ). Progeny will be traced over the short-term by the perdurance of LacZ as well as by immunostaining for the HA tag, which will provide validation for the use of perdurance over the short-term in the controls. To achieve conditional control of the transgenes, the dams and mice will be administered Dox in chow continuously until 10 weeks of age when the Dox is removed (the protocol used by Sinha). A wash-out period of 1 week is sufficient to establish strong expression of the TetO-responding transgenes, at which point, we will test the effect of maintained p63 expression on HBC fate under the same three conditions (normal OE, post-bulbectomy OE, and MeBr-lesioned OE) as for gene knockout (FIG. 4). The controls will be mice that lack the p63 transgene, but will have the same Dox-treatment regimen and will express tetop-LacZ, for tracing their progeny by LacZperdurance over the short term, as well as Dox-treated K5-CreERT2; R26R(LacZ) mice for longer term comparison.

In all cases, the composition of the clones will be determined quantitatively by application of our cell-marker panel to all sections that include the clone (Table 2). Depending on the number of clones per animal, every clone will be characterized, or even samples throughout the A-P extent of the epithelium will be made, with the goal of analyzing on the order of 30 clones per animal, with n=4 for each of the three

TABLE 1

Parental Mouse Lines

| Mouse Line | Use | Source |
|---|---|---|
| K5-CreERT2 | HBC-specific driver for conditional Cre | Pierre Chambon, INSERM in house (via Randy Reed) |
| fl(stop)ROSA26LacZ (R26RLacZ) | Cre-reporter line | Jax #003474 |
| fl(p63DBD) knockout | p63 knockout | Alea Mills, CSHL in house |
| K5-tTA | HBC-specific driver for Tet-OFF | Sat Sinha, SUNY-Buffalo (Adam Glick, originator) Promised |
| TetOp-HA-ΔNp63α | Tet-OFF regulated p63 expressor | Sat Sinha, SUNY-Buffalo Promised |
| TetOp-LacZ | Tet-OFF regulated LacZ expressor | Jax #002621 |
| fl(Notch1) | Notch1 knockout | Jax #006951 |
| fl(STOP)ROSA26-NICD | NICD expressor (constitutive Notch) | Jax #008159 |
| fl(b-catenin) | b-catenin knockout | Jax #004152 |
| b-catenin-fl(Exon3) | b-catenin expressor (constitutively active) | Albert Edge, MEEI Promised |

TABLE 2

Marker Identification of OE Cell Types

| | K5/14 | Sox2 | Pax6 | Mash1 (Ascl1) | NeuroD1 | Sox9 | K18 | PGP9.5 | NST | OMP | NCAM |
|---|---|---|---|---|---|---|---|---|---|---|---|
| HBC | + | + | + | | | | | | | | |
| GBC-MPP | | + | + | | | | | | | | |
| GBC-TA | | + | + | + | | | | | | | |
| GBC-INP | | ± | ± | | + | | | ± | ± | | |
| Sus | | + | + | | | + | | | | | |
| Duct/Gland | | | + | | + | + | | | | | |
| OSN-Imm | | | | | | | | + | + | | + |
| OSN-Mat | | | | | | | | + | | + | | conditions and gene status (control vs. p63-manipulated). In the past, in order to determine whether clone composition or size vary as a consequence of manipulation, we have used a multivariate Chi-square analysis (where each cell type is a factor), for example, in experiments where basal cells are transduced with RV vectors encoding Sox2 and/or Pax6[49]. The same approach will be taken comparing control and genetically manipulated groups for each condition.

Expected Outcomes, Potential Pitfalls, and Alternative Approaches. 1) With regard to p63 knockout, elimination of p63 in HBCs of normal OE is expected to cause more frequent activation to multipotency. While HBC activation to multipotency is a rare event in the normal and post-bulbectomy OE[24, 25], there are observed instances where cells appear to express HBC markers, but have lost p63 and have detached from the basal lamina[34]. It is hypothesized that such cells are becoming multipotent. Therefore, elimination of p63 is expected to lead to HBC activation and at an enhanced frequency following bulbectomy. When p63 is eliminated prior to MeBr lesion, universal activation to multipotency in response to the damage, a higher-than-control percentage of complex clones, and a correspondingly lower-than-control frequency of HBC-only clones is expected. Moreover, it is expected that none of the knock-out clones will contain HBCs, since p63 is required for HBC differentiation in development. If β-gal (+) HBCs are seen, staining will be performed for p63 and verification that recombination both activated the Cre reporter and knocked out p63. There might be a formal concern that elimination of p63 will kill target HBCs and yield no answer. However, the conversion of the GBCs that attempted to make HBCs into Sus and D/G cells in the p63 knock-out mice suggests that the absence of p63 is compatible with cell survival, despite the signals that push the progenitors to differentiate into HBCs. It is important to note that the K5-CreERT2 driver has been shown to be tightly regulated and not leaky[24]. This will be verified (looking for recombination and activation of LacZ in the absence of tamoxifen), but temporal control of the recombination events is expected to be tight.

With regard to over-expression of p63, the opposite effects are expected. The frequency with which activation occurs in the unlesioned or bulbectomized animals will be demonstrably less than in the control animals and will trend toward or reach zero. Likewise, static, unregulated expression of p63 from the transgene will block activation following MeBr injury, so that the clones will consist of only HBCs.

Three technical concerns need to be considered for the over-expression experiment. The first is the choice of isoform to act as the transgene. The preliminary data show that both the C-terminal a and p isoforms are expressed in the OE34. The ΔNp63α isoform is to be focused on because it is the full-length version of the gene. Moreover, all three C-terminal variants of p63 are capable of activating expression of CK5/14 in the epidermis, and the full-length ΔNp63α form is able to rescue the p63-mutant phenotype78. The second is the choice of the Tg(ΔNp63α) line. Multiple lines were generated by the Sinha lab and vary in the level of transgene expression, as shown by the latency and strength of the phenotype elicited by removal of Dox77. The weakest of the lines (designated D) will be used in order to approximate more physiological levels of expression. The third relates to the use of Tet-off regulation of p63 transgene expression. While previous work with both transgenes supports the experimental design and the predicted outcomes, it is possible that the Dox dosing will have to be altered to allow the animals to survive well into adulthood. Published data from the k5-tTA line suggest that altering the dose will indeed suffice76.

In sum, the results are expected to support the hypothesis that p63 is the master switch regulating HBC activation vs. quiescence. The IHC analysis, the developmental effects of p63 knockout, and the consequences of p63 transduction all suggest that the master switch hypothesis is well-founded. Nonetheless, if the results are other than what are expected— for example, if no clones are seen at 2 weeks because the genetic manipulations are not tolerated by the progeny—then shorter survivals will be tracked in order to catch the altered cells and analyze what they are/have become before they die.

Methods.

1) General protocols. The genotyping needed for breeding is routine in the lab, as we are already managing a number of different lines of transgenic/gene-targeted mice for a variety of purposes. Primers for identification of these and any other of the desired transgenes have been published or are available directly from the supplier (and are not listed here). Tamoxifen administration will follow the published protocol for using this K5-driven CreER[72] (injected IP at 0.07 mg/g b.w. once 2 weeks prior to activation)[24]. With regard to the genetically manipulated mice, recombination for p63 knockout and Tet-regulated expression of the p63 transgene will not be limited to the OE, but will affect a proportion of any cell population that expresses K5 (including basal cells of epidermal, respiratory, and other stratified epithelia). Should the disruption of p63 function in some of the basal cells in other epithelia compromise the health of the animals (in spite of the limited duration of the experiment), the extent of recombination and the overall effect on health can be lessened by reducing the dose of Tamoxifen in order to minimize the number of recombination events. The experimental manipulations of the OE by olfactory bulb ablation and by exposure to MeBr are ones with which we have 20+ years of published experience[79, 80]; the details will not be repeated here. The IHC analysis is well within our capabilities as demonstrated in multiple publications. For example, multiple novel protocols for staining low abundance, difficult to demonstrate antigens[15] have been independently developed. Thus, technical pitfalls for any of the foregoing aspects of the proposed experiments are not expected.

2) Breeding of the trigenic lines. The trigenic fl(p63 DBD)/fl(p63 DBD); K5-CreER[72]; R26R(LacZ) mice are nearly in hand. In 1 generation the first set of mice with the desired genotype will have been produced. To demonstrate the ability to design an efficient breeding strategy an example is described here: To generate p63 conditional knockout (cKO) animals, two parent lines were established: (1) fl(p63 DBD)×Rosa26(stop)lacZ (abbreviated fl(p63)×R26R) to generate the double homozygote line fl(p63)/fl(p63); R26R/R26R and (2) K5-CreER; R26R×fl(p63); R26R to generate the triple transgenic line K5-CreER; fl(p63)/+; R26R. These two parent strains will then be mated to each other (fl(p63)/fl(p63); R26R/R26R×K5-CreER; fl(p63)/+; R26R) to generate the cKO animals (K5-CreER; fl(p63)/fl(p63); R26R) and their control littermates (K5-CreER; fl(p63)/+; R26R). The mating of the 2 parental lines is currently underway, and we now have 4 breeding cages with a total of 9 females for this cross.

A similar strategy will be followed in making the Tg(K5-tTA); Tg(tetop-HA-ΔNp63α); Tg(tetop-LacZ) mice, except the already bigenic, Tg(K5-tTA); Tg(tetop-HA-ΔNp63α) mice will be received, which will accelerate the breeding of the desired trigenic phenotype.

2. The Role of Notch Signaling in the Activation of HBCs.

Does Notch signaling drive the early differentiation of activated HBCs? Might it activate them by itself? The Notch pathway can be up- and down-regulated in the HBCs of purely neurogenic vs. MeBr-lesioned OE, by using HBC-specific recombination to drive expression of NICD and constitutive Notch signaling, on the one hand, vs. HBC-specific knock-out of Notch1, on the other. In the MeBr-lesioned OE, it is expected that sus cells will predominate in the NIC-expressing, HBC-derived clones, based on results with retroviral transduction of GBCs. Conversely, knocking out Notch1 will likely drive neuronal differentiation by HBCs activated after injury. In the purely neurogenic OE, the outcome will be complex because Notch and p63 are often antagonistic. Based on observations elsewhere, it is expected that NICD will to repress p63 and activate HBCs. Conversely, elimination of Notch1 will likely prevent activation. Accordingly, the activation of Notch1 becomes an additional target for small molecule suppression of p63, thereby activating HBCs.

Purpose. To test whether signaling via the Notch pathway is required to activate HBCs by deleting Notch1 specifically in HBCs prior to MeBr lesion. We expect that multipotency will be blocked. Conversely, to test whether enhanced Notch signaling can lead to activation of HBCs in the normal OE on its own, in the absence of other potential signals.

Rationale. The Notch pathway seems to play a prominent role in the regulation of progenitor cell capacity and the choice between alternate cell fates/differentiation programs[81-83]. The four homologues in mammals are Notch1-4. The receptor type expressed by HBCs is Notch1, as shown by IHC in the experiments described herein[52] and microarray profiling[53]. Two different Notch1 antibodies stain the HBCs, and the expression of Notch1 mRNA is 5-fold higher in HBCs FACS-harvested from the normal OE by comparison with the epithelium as a whole. By way of contrast, the levels of the other Notch receptors are no higher in HBCs than in the tissue as a whole, and antibodies to Notch2 show no staining of HBCs. The correlation of microarray and IHC data provide some assurance that the assignment is correct, even though our results may differ from other published work.

There are multiple reasons for thinking that Notch signaling regulates the activation of HBCs after lesion. First, microarray results demonstrate significant shifts in levels of expression of Notch pathway components when CD54(+) HBCs from normal OE are compared to ones from 2 days post-MeBr OE. The pattern is complex (some are up and some are down) but the population at 2 days is also complex and includes both p63(+) and p63(−) CD54-labeled basal cells, i.e., ones that remain reserve stem cells vs. others that are actively multipotent, respectively. Second, in multiple settings (intestine[84, 85], skin[86], ES cells[87], hematopoiesis[88]), Notch signaling promotes progression out of a stem cell state toward a downstream progenitor like a transit-amplifying cell. Admittedly, Notch signaling is known to play a complex role in neural stem cells in the CNS participating in both stem cell maintenance as well as differentiation[89, 90]. Third, the outcome of modulating Notch expression in the post-MeBr OE, suggests that active Notch signaling prevents progenitors from generating or regenerating HBCs; NICD causes the accumulation of differentiated cell types other than HBCs, while blocking Notch signaling with DN-MAML leaves some cells as basal cells[52]. Fourth, Notch and p63 have strongly antagonistic effects on cell differentiation in other epithelia, including breast and skin, where Notch counteracts p63's role in maintaining the basal cell/stem cell phenotype[43, 44, 91]. As a consequence of the tissue-specific complexities of Notch action one cannot infer function solely by analogy. Are HBCs more likely to behave like the p63 (+) stem cells of skin and breast with respect to the impact of Notch or more like the ependymal cells of the lateral ventricle, in which Notch prevents progression from quiescence to multipotency[92]? Either outcome will provide valuable insight into the regulation of HBCs.

Design. These experiments also take advantage of a genetic approach, using mouse lines in which components of the Notch signaling pathway can be manipulated using the K5-CreERT2 HBC-specific driver to conditionally knock-out vs. conditionally activate the pathway (FIG. 4). Trigenic lines (Table 1) will be bread. For Notch1 knockout, the trigenic genotype will be K5-CreERT2; fl(Notch1)/fl(Notch1); R26R (LacZ). For expression of NICD, the genotype will be K5-CreERT2; R26-fl(stop)NICD/R26R(LacZ). With regard to the latter, there are 3 different Tg(fl(stop)NICD) mice readily available from the Jackson Labs (Table 1). For the initial studies, we prefer Melton's Rosa26-fl(stop)NICD line[93]. It is known that the ROSA26 locus is expressed reasonably well in the cells of the OE, but levels are not as high as seen with RV transduction; thus, the ROSA locus may generate a more physiologic effect. In this case, the NICD construct is allelic to the LacZ construct, so the breeding strategy will be reasonably simple.

For these studies of Notch signaling, it is proposed to use the same kinds of experimental manipulations as above, which include knocking-out and activating Notch in HBCs of normal, post-bulbectomy, and post-MeBr exposed mice (FIG. 4). However, because Notch1 manipulation clearly exerts an effect on cell differentiation downstream of the HBCs, we will also need to examine an early time-point after recombination has occurred in order to distinguish early vs. late effects of the pathway. The type of analytic approach used here is the same as above; quantitative analysis of the composition of clones arising from the gene-targeted HBCs. Besides the cell-type specific labels (which are generally structural genes) staining for Notch and for p63 will be performed in order to see whether there is a correlation between the nuclear accumulation of NICD and the level of p63 expression.

Expected Outcomes, Potential Pitfalls, Alternative Approaches. With respect to conditional knock-out of Notch1, it is expected that eliminating Notch1 will further suppress the infrequent activation of HBCs in the normal and post-bulbectomy OE and/or prevent their activation completely, following MeBr lesion, by releasing Notch1 inhibition of p63. In this regard, the HBCs are most like the basal cells of the skin and breast in which Notch-suppression of p63 permits stem cells to transition out of quiescence and function as active progenitors[43, 44, 91]. The effect of gene knockout in the purely neurogenic epithelium is predicated on a static level of Notch signaling in the HBCs despite the absence of epithelial damage, which we cannot determine directly (because the levels of NICD generated by endogenous signaling are undetectable by conventional IHC as shown by the disconnect between Hes1 expression and detectability of nuclear NICD in residual basal cells of the lesioned OE). An indirect measure of Notch signaling is elevated, i.e., the levels of the canonical Notch1 target genes of the Hes and Hey gene families. Both Hes1 and Hey2 are modestly elevated in HBCs relative to whole mucosa (significantly higher, but only about 2.5- and 1.5-fold, respectively, though the increase for Hey2 is evident with multiple probes)[53]. Thus, the existing data suggest that ongoing signaling via Notch1 may indeed be occurring even in the normal epithelium.

The effect of Notch1 knockout following MeBr lesion is likely to be complex. Given the effect of RV transduction with DN-MAML[52] and the onset of Hes1 expression in GBCs that progress to Sus cells, it is highly likely that Notch1-knockout clones will consist of neurons and basal cells only. In addition, the contribution of Notch to proliferation in many other settings may mean that the clones will be markedly smaller than in control mice that are heterozygote for the fl(Notch1) allele. Finally, to the extent that Notch1 signaling is responsible for reactivating p63 expression and HBC differentiation, the knockout clones may lacking HBCs.

With respect to the over-expression of NICD in HBCs, it is expected that activation will be prevented or delayed in the MeBr-lesioned OE as well as in the purely neurogenic epithelium. Given enhanced proliferation due to Notch1, the NICD-expressing clones may end up larger than in control. Of course, should clones be seen, they are expected to lack neurons, and under those circumstances shorter time-points after lesion will be examined to see whether activation is delayed. Should an effect be unseen, it is possible that the level of NICD coming from the ROSA locus is insufficient to over-ride the termination of Notch signaling via proteosomal breakdown of NICD, although the ROSA-targeted construct has been effective in redirecting cell differentiation elsewhere[93]. In that case, two other NICD transgenes can be tried that express at higher levels than the ROSA26 locus (Table 1). The CALSL-NICD (Chicken Actin promotor-LoxP-Stop-LoxP) mice carry 10-20 copies of the transgene in a single locus such that NICD levels after Cre-mediated recombination are high enough to be detectable by Western Blot, which is higher than the level achieved from the ROSA locus[94]. Alternatively, the CAG promoter-driven NICD transgene (Z/EG-Notch) is also expressed more strongly than ROSA[95]. In the latter case, the NICD-IRES-GFP construct is activated when the floxed constitutively-expressed LacZ is removed by recombination, eliminating the need to bring the R26R(LacZ) allele into the bigenic line.

In sum, these experiments will determine whether Notch signaling regulates the level of p63 expression by HBCs, the acquisition of the morphological correlates of activation (namely detaching from the basal lamina and shifting apically), and the type of progeny to which the Notch1-knockout vs. NICD-over-expresser give rise. As a consequence, whether Notch signaling is antagonistic to, synergistic with, or neutral for p63 regulation of HBC progenitor status will be determined.

Methods. All of the methods for Tam-induced recombination, manipulation of the OE and analysis of the outcome are the same. Likewise, a similar breeding strategy as in above will be developed and used.

3. The Role of Wnt Signaling in the Activation of HBCs.

Is Wnt signaling antagonistic to Notch in HBCs? Does constitutive activation of the canonical Wnt pathway in HBCs—by blocking breakdown of β-catenin by gene mutation—suppress activation or induce it in either neurogenic or MeBr-lesioned OE? If so, how does modulating Wnt compare to modulating Notch activation? Conversely, what is the consequence of HBC-limited β-catenin knockout? Analogy to other systems is a poor guide to outcome in this case, but with either outcome, Wnt, too, becomes a potential target for altering HBC status.

Purpose. To test whether Wnt signaling prevents activation of HBCs to multipotency in response to injury, by expressing a non-degradable form of β-catenin specifically and conditionally in HBCs. Conversely, to test whether blocking Wnt signaling will initiate or enhance activation of HBCs.

Rationale. The Wnt pathway, too, plays a major role in regulating the maintenance vs. differentiation of stem and progenitor cells in many tissues[96]. Moreover, Wnt signaling is frequently antagonistic to Notch signaling and vice-versa, so much so that the term "Wntch" signaling has been used to describe the yin-yang relationship of these contrary but interdependent pathways[97]. Thus, in ES cells, skin, intestine, and in hematopoeisis, Wnt signaling has been associated with maintaining stem cells and blocking progression toward the production of differentiated elements, which is opposite to the effect of Notch signaling (as noted above)[97]. Wnt signaling is very complex, consisting of multiple Wnt ligands, multiple LRP co-receptors, and multiple Frizzled receptors[96]. In general, most of the Wnt-mediated effects on stem and progenitor cells are exerted via the canonical pathway, which entails release of non-phosphorylated β-catenin from the axin-GSK3-APC destruction complex, and its translocation to the nucleus where it binds to LEF/TCF TFs and thereby activates gene expression[96]. The Wnt pathway is operative in the olfactory epithelium[56] (as well as more centrally where olfactory axons and glia interface with the bulb[98-100]). The presence of multiple Wnts and Wnt pathway components in the olfactory epithelium has been demonstrated, as have the activation of the TOP-GFP Wnt-signaling reporter in basal cells and immature neurons, alterations in the regeneration of the olfactory epithelium in response to small molecule inhibitors of β-catenin destruction, and enhanced passaging of olfactospheres when Wnt3a is added to the media[56].

The very complexity of the Wnt system suggests that the most efficacious strategy for investigating its cell-specific function is by targeting the final and common node in the pathway, namely β-catenin. To that end, HBC-specific and conditional recombination will be used to generate: (1) a knockout of β-catenin using the fl(B-cat) mouse available from the Jax[101], and (2) activation of β-catenin, by clipping out floxed exon 3, which encodes the phosphorylation site of β-catenin, leading to its constitutive activation[102]. The constitutively active mutant mouse will be obtained from our collaborator, Dr. Albert Edge of the Mass Eye and Ear Infirmary. In the absence of recombination the mouse breeds well and has no apparent phenotype. In very preliminary studies, we have examined the olfactory epithelium of animals in which a CMV-CreERT2 driver was used to remove exon 3. In this case, there is no selection of which cells have undergone recombination, and we have not yet looked at β-catenin staining in these animals (no reporter allele was bred into these animals). Nonetheless, the findings are very intriguing, indicating that excessive Wnt signaling is associated with an olfactory phenotype. Beta-catenin over-expression in mice produced foci of hyperplasia and areas of neurogenic "burn-out", where the OE is aneuronal, similar to the appearance in humans. A typical foci of epithelial hyperplasia observed in the over-expressing mice cells was seen to have a transition zone between OE and the nodule. In the same mouse, aneuronal stretches of OE were observed, that suggests a failure of HBCs to activate. Also observed were smaller areas with the same composition. Not only were there foci of hyperproliferation, but other areas of the epithelium have become aneuronal/non-neurogenic with preserved HBCs as seen in elderly humans. It is plausible that the failure of HBCs to activate in these circumstances is due to/exacerbated by the ongoing expression of active β-catenin.

Design. The basic design for this set of experiments is the same as above, again taking advantage of a genetic approach, using mouse lines in which β-catenin is targeted for either elimination or constitutive activation using K5-CreERT2, to limit recombination to HBCs. For β-catenin knockout, the trigenic genotype will be K5-CreERT2; fl(ctnnb1)/fl(ctnnb1); R26R(LacZ). For expression of constitutively active β-catenin, the genotype will be K5-CreERT2; fl(exon3)ctnnb1; R26R(LacZ) (Table 1). We plan to Tam-activate and to excise under the same three conditions (normal, post-bulbectomy, and post-MeBr exposure) as before (FIG. 4). As for the Notch experiments, include a shorter survival time may be necessary to include, as alterations of Wnt signaling may well change the progenitor capacity of cells downstream of the HBCs. In addition to the standard cell-type specific antibody markers, we will also stain for p63, for β-catenin using an antibody with which we have experience, and for Notch1.

Expected Outcomes and Potential Pifalls. Given the prevalence with which Notch signaling and Wnt signaling act in opposition to each other in so many other tissues, it is expected that the outcomes of Wnt manipulation will be similar to those observed when Notch is targeted—just in the opposite direction. Thus, Wnt knockout will most likely lead to HBC activation and constitutively active Wnt will suppress it (FIG. 4). The timing of the evaluation will likely be important to observing and understanding the consequences of genetic manipulation, and so we will look a few days after recombination as well as at the standard 2-week time-point. Will the changes induced by the genetic manipulations be interpretable? β-catenin staining is not evident in HBCs normally (in contrast to Sus cells, where the β-catenin label is concentrated at the lateral cell margins near the adherens junctions). Thus, it is not thought that β-catenin knockout will be immediately fatal to the cell, and we will be able to study Wnt effects on HBC activation. β-catenin activation is expected to be compatible with survival, given the age of the mice in the preliminary study.

Methods. All of the methods for Tam-induced recombination, manipulation of the OE and analysis of the outcome are the same as above. A similar breeding strategy as utilized above will be developed and used. The fl(β-catenin) line will be obtained from the Jackson labs.

4. Summary

All the preliminary data presented here suggest that Notch and Wnt will act as antagonists in signaling HBCs to shift from quiescence to active status as multipotent progenitors, and back again, and that the agent for change in HBC status is the expression of p63. The proposed experiments will provide definitive answers regarding the function of these pathways and effectors in HBCs, since they use highly regulated, conditional, HBC-specific gene manipulation. Of course, those answers are just the starting point in understanding why HBCs do not always activate out of quiescence when needed, and in designing therapeutic interventions. For example, what genes p63 regulates (ChIP-Seq experiments on HBCs from normal OE and in-depth comparison with microarray data from quiescent and activated HBCs), what TFs regulate it (working backward from the p63 enhancer/promoter by EMSA and proteomic analysis of HBC nuclear extracts), and how Notch and Wnt signals impinge on p63 expression (using cell lines to interfere with sequential steps in the signaling cascade and to determine what genes change as a consequence of these signals) will be determined. To the extent that Notch and Wntare key to the process, the small molecule modulators of these pathways that are being developed are potential agents for use in animal models of HBC dysfunction. Nonetheless, when the current experiments are completed they will provide increased understanding and indicate methods of treating this form of olfactory disruption.

5. Materials and Methods

Vertebrate Animals. The experiments proposed here, all of which are described in approved animal use and care protocols (IACUC), entail the spatial and temporal control over gene recombination in vivo. All of the experiments will use mice, of which there are a number of lines as listed in Table 1. These parental lines will be bred to generate a 6 different bi and tri-genic lines that bring together the driver, gene target, and reporter constructs to knock-out p63, Notch1, and b-catenin (each in its own trigenic line) and to express the constitutively active forms of Notch1 and b-catenin (likewise). The foregoing all require activation of the recombinase by administration of tamoxifen (see below). In addition, a line will be generated that can be used to force static expression of a p63 (i.e., expression that is not subject to the usual regulation) via a Tet-OFF approach. Again three transgenic constructs will be brought together to drive expression, and to respond to the driver to make p63 and a LacZ reporter. Gene recombination/ expression will be activated, and then some of the mice will be exposed to MeBr and others will undergo olfactory bulbectomy. All will then be euthanized by anesthetic overdose and fixative perfusion for purposes of tissue harvest.

Numbers. An example of the breeding strategy follows (again repeated from the Research Strategy part of the application). To generate p63 conditional knockout (cKO) animals, two parent lines were established: (1) fl(p63 DBD)× Rosa26(stop)lacZ (abbreviated fl(p63)×R26R) to generate the double homozygote line fl(p63)/fl(p63); R26R/R26R and (2) K5-CreER; R26R×fl(p63); R26R to generate the triple transgenic line K5-CreER; fl(p63)/+; R26R. These two parent strains will then be mated to each other (fl(p63)/fl(p63); R26R/R26R×K5-CreER; fl(p63)/+; R26R) to generate the cKO animals (K5-CreER; fl(p63)/fl(p63); R26R) and their control littermates (K5-CreER; fl(p63)/+; R26R). The mice to be used for experimental purposes will be spin-offs from the various genetic crosses. For each trigenic line and its genetic control there are 3 experimental conditions and 2-3 time-points. 4 animals per condition for a total of 72 mice per each of the three experiments described above will be used.

Tamoxifen treatment. Mice of the correct genotype will be injected i.p. with tamoxifen at 0.07 mg/g b.w. once 2 weeks prior to use.

Doxycycline treatment. Because a Tet-OFF driver is being used to regulate expression of the p63 transgene, breeding pairs and experimental mice will be maintained on Dox-chow continuously, which will be withdrawn roughly 1 week prior to experimental manipulation.

MeBr lesion. The mice from each of the individual strains, will be exposed to MeBr at 180 ppm in air for 8 hours while awake and unrestrained, which produces a complete lesion of all parts of the olfactory epithelium in mice without any evident discomfort (no discomfort is expected since the pain fibers are found below the basal lamina and are unaffected by the lesion).

Olfactory bulb ablation. Olfactory bulb ablation is performed sterilely as follows. Animals are anesthetized by ip injection of a triple cocktail of ketamine/xylazine/acepromazine (14, 3.6, and 0.7 mg/kg, respectively), betadine scrubbed, and draped. After incising the scalp along the midline, a dorsal carniotomy exposes the bulb, which is then removed by suction. The cavity is filled with gel-foam for hemostasis and the animal is sutured. For those animals subject to bulb ablation, postsurgical discomfort is minimal, but the possibility will be alleviated with injections of buprinorphinesqat 0.05-0.1 mg/kg as the animal awakens and then q12 hours as needed.

Euthanasia. Animals will be euthanized by the anesthetic overdose. In adults anesthesia is accomplished by ip injection of a triple cocktail of ketamine/xylazine/acepromazine (52, 10.8, and 2 mg/kg, respectively). When deeply anesthetized the animals are perfused with PBS and then fixative, before being decapitated for tissue harvest.

References Example 1

1. Doty, R. L. A review of olfactory dysfunctions in man. *Am J Otolaryngol* 1, 57-79 (1979).

2. Doty, R. L. Influence of age and age-related diseases on olfactory function. *Ann N Y Acad Sci* 561, 76-86 (1989).
3. Moran, D. T., Jafek, B. W., Eller, P. M. & Rowley, J. C., 3rd Ultrastructural histopathology of human olfactory dysfunction. *Microsc Res Tech* 23, 103-110 (1992).
4. Holbrook, E. H., Leopold, D. A. & Schwob, J. E. Abnormalities of axon growth in human olfactory mucosa. *Laryngoscope* 115, 2144-2154 (2005).
5. Jang, W., Youngentob, S. L. & Schwob, J. E. Globose basal cells are required for reconstitution of olfactory epithelium after methyl bromide lesion. *J Comp Neurol* 460, 123-140 (2003).
6. Leopold, D. A., Hornung, D. E. & Schwob, J. E. Congenital lack of olfactory ability. *Ann Otol Rhinol Laryngol* 101, 229-236. (1992).
7. Schwob, J. E., Szumowski, K. E., Leopold, D. A. & Emko, P. Histopathology of olfactory mucosa in Kallmann's syndrome. *Ann Otol Rhinol Laryngol* 102, 117-122. (1993).
8. Schwob, J. E., Youngentob, S. L. & Meiri, K. F. On the formation of neuromata in the primary olfactory projection. *J Comp Neurol* 340, 361-380. (1994).
9. Snippert, H. J. et al. Intestinal crypt homeostasis results from neutral competition between symmetrically dividing Lgr5 stem cells. *Cell* 143, 134-144 (2010).
10. Barker, N., Bartfeld, S. & Clevers, H. Tissue-resident adult stem cell populations of rapidly self-renewing organs. *Cell Stem Cell* 7, 656-670 (2010).
11. Cau, E., Casarosa, S. & Guillemot, F. Mash1 and Ngn1 control distinct steps of determination and differentiation in the olfactory sensory neuron lineage. *Development* 129, 1871-1880 (2002).
12. Cau, E., Gradwohl, G., Casarosa, S., Kageyama, R. & Guillemot, F. Hes genes regulate sequential stages of neurogenesis in the olfactory epithelium. *Development* 127, 2323-2332. (2000).
13. Cau, E., Gradwohl, G., Fode, C. & Guillemot, F. Mash1 activates a cascade of bHLH regulators in olfactory neuron progenitors. *Development* 124, 1611-1621. (1997).
14. Gordon, M. K., Mumm, J. S., Davis, R. A., Holcomb, J. D. & Calof, A. L. Dynamics of MASH1 expression in vitro and in vivo suggest a non-stem cell site of MASH1 action in the olfactory receptor neuron lineage. *Mol Cell Neurosci* 6, 363-379. (1995).
15. Guo, Z. et al. Expression of pax6 and sox2 in adult olfactory epithelium. *J Comp Neurol* 518, 4395-4418 (2010).
16. Manglapus, G. L., Youngentob, S. L. & Schwob, J. E. Expression patterns of basic helix-loop-helix transcription factors define subsets of olfactory progenitor cells. *J Comp Neurol* 479, 216-233 (2004).
17. Packard, A. I., Giel, M., Leiter, A. B. & Schwob, J. E. The progenitor cell capacity of NeuroD1-expressing globose basal cells in the mouse olfactory epithelium. *J Comp Neurol* in press (2011).
18. Goldstein, B. J., Fang, H., Youngentob, S. L. & Schwob, J. E. Transplantation of multipotent progenitors from the adult olfactory epithelium. *Neuroreport* 9, 1611-1617. (1998).
19. Chen, X., Fang, H. & Schwob, J. E. Multipotency of purified, transplanted globose basal cells in olfactory epithelium. *J Comp Neurol* 469, 457-474 (2004).
20. Huard, J. M., Youngentob, S. L., Goldstein, B. J., Luskin, M. B. & Schwob, J. E. Adult olfactory epithelium contains multipotent progenitors that give rise to neurons and non-neural cells. *J Comp Neurol* 400, 469-486. (1998).
21. Goldstein, B. J. & Schwob, J. E. Analysis of the globose basal cell compartment in rat olfactory epithelium using GBC-1, a new monoclonal antibody against globose basal cells. *J Neurosci* 16, 4005-4016. (1996).
22. Jang, W., Kim, K. P. & Schwob, J. E. Nonintegrin laminin receptor precursor protein is expressed on olfactory stem and progenitor cells. *J Comp Neurol* 502, 367-381 (2007).
23. Chen, X. & Schwob, J. E. Quiescent globose basal cells are present in the olfactory epithelium. *Chem Senses* 28, A5 (2003).
23a. Carter, L. A., MacDonald, J. L. & Roskams, A. J. Olfactory horizontal basal cells demonstrate a conserved multipotent progenitor phenotype. *J Neurosci* 24, 5670-5683 (2004).
24. Leung, C. T., Coulombe, P. A. & Reed, R. R. Contribution of olfactory neural stem cells to tissue maintenance and regeneration. *Nat Neurosci* 10, 720-726 (2007).
25. Iwai, N., Zhou, Z., Roop, D. R. & Behringer, R. R. Horizontal basal cells are multipotent progenitors in normal and injured adult olfactory epithelium. *Stem Cells* 26, 1298-1306 (2008).
26. Schnittke, N., Packard, A. & Schwob, J. E. Activation of horizontal basal cells in the olfactory epithelium. *Chem Senses* in press (2011).
27. Alvarez-Buylla, A., Garcia-Verdugo, J. M. & Tramontin, A. D. A unified hypothesis on the lineage of neural stem cells. *Nat Rev Neurosci* 2, 287-293 (2001).
28. Alonso, L. & Fuchs, E. Stem cells of the skin epithelium. *Proc Natl Acad Sci USA* 100 Suppl 1, 11830-11835 (2003).
29. Rock, J. R., Randell, S. H. & Hogan, B. L. Airway basal stem cells: a perspective on their roles in epithelial homeostasis and remodeling. *Dis Model Mech* 3, 545-556.
30. Nakashima, T., Kimmelman, C. P. & Snow, J. B., Jr. Structure of human fetal and adult olfactory neuroepithelium. *Arch Otolaryngol* 110, 641-646 (1984).
31. Nakashima, T., Kimmelman, C. P. & Snow, J. B., Jr. Olfactory marker protein in the human olfactory pathway. *Arch Otolaryngol* 111, 294-297 (1985).
32. Naessen, R. An enquiry on the morphological characteristics and possible changes with age in the olfactory region of man. *Acta Otolaryngol* 71, 49-62 (1971).
33. Largent, B. L., Sosnowski, R. G. & Reed, R. R. Directed expression of an oncogene to the olfactory neuronal lineage in transgenic mice. *J Neurosci* 3, 300-312. (1993).
34. Packard, A., Schnittke, N., Sinha, S. & Schwob, J. E. ΔNp63 regulates stem cell dynamics in the mammalian olfactory epithelium. *J Neurosci* submitted (2011).
35. Crum, C. P. & McKeon, F. D. p63 in epithelial survival, germ cell surveillance, and neoplasia. *Annu Rev Pathol* 5, 349-371.
36. Mills, A. A. et al. p63 is a p53 homologue required for limb and epidermal morphogenesis. *Nature* 398, 708-713 (1999).
37. Yang, A. et al. p63 is essential for regenerative proliferation in limb, craniofacial and epithelial development. *Nature* 398, 714-718 (1999).
38. Yang, A. et al. p63, a p53 homolog at 3q27-29, encodes multiple products with transactivating, death-inducing, and dominant-negative activities. *Mol Cell* 2, 305-316 (1998).
39. Pellegrini, G. et al. p63 identifies keratinocyte stem cells. *Proc Natl Acad Sci USA* 98, 3156-3161 (2001).
40. Koster, M. I., Kim, S., Mills, A. A., DeMayo, F. J. & Roop, D. R. p63 is the molecular switch for initiation of an epithelial stratification program. *Genes Dev* 18, 126-131 (2004).
41. Yi, R., Poy, M. N., Stoffel, M. & Fuchs, E. A skin microRNA promotes differentiation by repressing 'stemness'. *Nature* 452, 225-229 (2008).

42. Nguyen, B. C. et al. Cross-regulation between Notch and p63 in keratinocyte commitment to differentiation. *Genes Dev* 20, 1028-1042 (2006).
43. Yalcin-Ozuysal, O. et al. Antagonistic roles of Notch and p63 in controlling mammary epithelial cell fates. *Cell Death Differ* 17, 1600-1612 (2010).
44. Shahi, P., Seethammagari, M. R., Valdez, J. M., Xin, L. & Spencer, D. M. Wnt and Notch Pathways have Interrelated Opposing Roles on Prostate Progenitor Cell Proliferation and Differentiation. *Stem Cells* (2011).
45. Okuyama, R., Tagami, H. & Aiba, S, Notch signaling: its role in epidermal homeostasis and in the pathogenesis of skin diseases. *J Dermatol Sci* 49, 187-194 (2008).
46. Drewelus, I. et al. p63 antagonizes Wnt-induced transcription. *Cell Cycle* 9, 580-587.
47. Leopold, D. A., Loehrl, T. A. & Schwob, J. E. Long-term follow-up of surgically treated phantosmia. *Arch Otolaryngol Head Neck Surg* 128, 642-647 (2002).
48. Leopold, D. A. et al. Successful treatment of phantosmia with preservation of olfaction. *Arch Otolaryngol Head Neck Surg* 117, 1402-1406. (1991).
49. Packard, A. *Regulation of Stem Cells and Neurogenesis in the Adult Olfactory Epithelium*. Ph.D. Thesis in Cell, Molecular and Developmental Biology (Tufts University, Boston; 2010).
50. Jang, W., Lambropoulos, J., Woo, J. K., Peluso, C. E. & Schwob, J. E. Maintaining epitheliopoietic potency when culturing olfactory progenitors. *Exp Neurol* (2008).
51. Krolewski, R. C., Jang, W. & Schwob, J. E. The generation of olfactory epithelial neurospheres in vitro predicts engraftment. *Exper Neurol* In press (2011).
52. Guo, Z. *Maintenance, Differentiation and Regulation of Multipotent Progenitor Cells in Olfactory Epithelium*. Ph.D. Thesis in Cell, Molecular, and Developmental Biology (Tufts University, Boston, Mass.; 2008).
53. Krolewski, R. C. *Expression Profiling and In Vitro Analysis of Olfactory Epithelial Stem and Progenitor Cells*. Ph.D. Thesis in Cell, Molecular and Developmental Biology (Tufts University, Boston, Mass.; 2010).
54. Guo, Z., Manglapus, G. L. & Schwob, J. E. Role of Notch signaling in olfactory epithelium. *Soc Neurosci Abstr* 33, 220.229 (2007).
55. Krolewski, R. C., Packard, A., Wildner, H. & Schwob, J. E. Disruption of neurogenesis in the olfactory epithelium by Ascl1 (Mash1) knockout perturbs differentiation of normeuronal cells. *Dev Dyn* submitted (2011).
56. Wang, Y.-Z. et al. Canonical Wnt signaling promotes proliferation and neurogenesis of peripheral olfactory stem cells/progenitors during postnatal development and adult regeneration. *J Cell Sci* in press (2011).
57. Schwob, J. E., Kurtz, D. L. & Goldstein, B. J. in Basic Science Review for Otolaryngology. (eds. T. Van De Water & H. Staecker) 485-496 (Thieme, New York; 2005).
58. Schwob, J. E. & Jang, W. in Neural Development and Stem Cells, Second Edition. (ed. M. S. Rao) 219-233 (Humana Press, Totowa, N.J.; 2005).
59. Schwob, J. E. & Costanzo, R. M. in The Senses: A Comprehensive Reference. (eds. I. B. Allan et al.) 591-612 (Academic Press, New York; 2008).
60. Youngentob, S. L. & Schwob, J. E. Odorant identification and quality perception following methyl bromide-induced lesions of the olfactory epithelium. *Behav Neurosci* 120, 1346-1355 (2006).
61. Thompson, K. J. et al. Manganese uptake and distribution in the brain after methyl bromide-induced lesions in the olfactory epithelia. *Toxicol Sci* 120, 163-172 (2011).
62. Thompson, K. et al. Olfactory uptake of manganese requires DMT1 and is enhanced by anemia. *Faseb J* 21, 223-230 (2007).
63. Christie, S. B., Akins, M. R., Schwob, J. E. & Fallon, J. R. The FXG: a presynaptic fragile X granule expressed in a subset of developing brain circuits. *J Neurosci* 29, 1514-1524 (2009).
64. Bakos, S. R., Schwob, J. E. & Costanzo, R. M. Matrix metalloproteinase-9 and -2 expression in the olfactory bulb following methyl bromide gas exposure. *Chem Senses* 35, 655-661 (2010).
65. Romano, R. A., Ortt, K., Birkaya, B., Smalley, K. & Sinha, S. An active role of the DeltaN isoform of p63 in regulating basal keratin genes K5 and K14 and directing epidermal cell fate. *PLoS ONE* 4, e5623 (2009).
66. Ortt, K., Raveh, E., Gat, U. & Sinha, S. A chromatin immunoprecipitation screen in mouse keratinocytes reveals Runx1 as a direct transcriptional target of DeltaNp63. *J Cell Biochem* 104, 1204-1219 (2008).
67. Birkaya, B., Ortt, K. & Sinha, S, Novel in vivo targets of DeltaNp63 in keratinocytes identified by a modified chromatin immunoprecipitation approach. *BMC Mol Biol* 8, 43 (2007).
68. Romano, R. A., Birkaya, B. & Sinha, S. A functional enhancer of keratin14 is a direct transcriptional target of deltaNp63. *J Invest Dermatol* 127, 1175-1186 (2007).
69. Ortt, K. & Sinha, S. Derivation of the consensus DNA-binding sequence for p63 reveals unique requirements that are distinct from p53. *FEBS Lett* 580, 4544-4550 (2006).
70. Yang, A. et al. Relationships between p63 binding, DNA sequence, transcription activity, and biological function in human cells. *Mol Cell* 24, 593-602 (2006).
71. Senoo, M., Pinto, F., Crum, C. P. & McKeon, F. p63 is essential for the proliferative potential of stem cells in stratified epithelia. *Cell* 129, 523-536 (2007).
72. Kurita, T., Medina, R. T., Mills, A. A. & Cunha, G. R. Role of p63 and basal cells in the prostate. *Development* 131, 4955-4964 (2004).
73. Signoretti, S. et al. p63 is a prostate basal cell marker and is required for prostate development. *Am J Pathol* 157, 1769-1775 (2000).
74. Candi, E. et al. DeltaNp63 regulates thymic development through enhanced expression of FgfR2 and Jag2. *Proc Natl Acad Sci USA* 104, 11999-12004 (2007).
75. Mills, A. A., Qi, Y. & Bradley, A. Conditional inactivation of p63 by Cre-mediated excision. *Genesis* 32, 138-141 (2002).
76. Diamond, I., Owolabi, T., Marco, M., Lam, C. & Glick, A. Conditional gene expression in the epidermis of transgenic mice using the tetracycline-regulated transactivators tTA and rTA linked to the keratin 5 promoter. *J Invest Dermatol* 115, 788-794 (2000).
77. Romano, R. A., Smalley, K., Liu, S. & Sinha, S. Abnormal hair follicle development and altered cell fate of follicular keratinocytes in transgenic mice expressing DeltaNp63alpha. *Development* 137, 1431-1439 (2010).
78. Candi, E. et al. Differential roles of p63 isoforms in epidermal development: selective genetic complementation in p63 null mice. *Cell Death Differ* 13, 1037-1047 (2006).
79. Schwob, J. E., Szumowski, K. E. & Stasky, A. A. Olfactory sensory neurons are trophically dependent on the olfactory bulb for their prolonged survival. *J Neurosci* 12, 3896-3919. (1992).
80. Schwob, J. E., Youngentob, S. L. & Mezza, R. C. Reconstitution of the rat olfactory epithelium after methyl bromide-induced lesion. *J Comp Neurol* 359, 15-37. (1995).

81. Artavanis-Tsakonas, S., Rand, M. D. & Lake, R. J. Notch Signaling: Cell fate control and signal integration in development. *Science* 284, 770-776 (1999).
82. Weinmaster, G. & Kopan, R. A garden of Notch-ly delights. *Development* 133, 3277-3282 (2006).
83. Bray, S. J. Notch signalling: a simple pathway becomes complex. *Nat Rev Mol Cell Biol* 7, 678-689 (2006).
83a. Carson, C., Murdoch, B. & Roskams, A. J. Notch 2 and Notch 1/3 segregate to neuronal and glial lineages of the developing olfactory epithelium. *Dev Dyn* 235, 1678-1688 (2006).
84. Sancho, E., Batlle, E. & Clevers, H. Live and let die in the intestinal epithelium. *Curr Opin Cell Biol* 15, 763-770 (2003).
85. Radtke, F. & Clevers, H. Self-renewal and cancer of the gut: two sides of a coin. *Science* 307, 1904-1909 (2005).
86. Lowry, W. E. et al. Defining the impact of beta-catenin/Tcf transactivation on epithelial stem cells. *Genes Dev* 19, 1596-1611 (2005).
87. Lowell, S., Benchoua, A., Heavey, B. & Smith, A. G. Notch promotes neural lineage entry by pluripotent embryonic stem cells. *PLoS Biol* 4, e121 (2006).
88. Radtke, F., Wilson, A., Ernst, B. & MacDonald, H. R. The role of Notch signaling during hematopoietic lineage commitment. *Immunol Rev* 187, 65-74 (2002).
89. Kageyama, R., Ohtsuka, T., Shimojo, H. & Imayoshi, I. Dynamic Notch signaling in neural progenitor cells and a revised view of lateral inhibition. *Nat Neurosci* 11, 1247-1251 (2008).
90. Yoon, K. & Gaiano, N. Notch signaling in the mammalian central nervous system: insights from mouse mutants. *Nat Neurosci* 8, 709-715 (2005).
91. Truong, A. B. & Khavari, P. A. Control of keratinocyte proliferation and differentiation by p63. *Cell Cycle* 6, 295-299 (2007).
92. Carlen, M. et al. Forebrain ependymal cells are Notch-dependent and generate neuroblasts and astrocytes after stroke. *Nat Neurosci* 12, 259-267 (2009).
93. Greenwood, A. L., Li, S., Jones, K. & Melton, D. A. Notch signaling reveals developmental plasticity of Pax4(+) pancreatic endocrine progenitors and shunts them to a duct fate. *Mech Dev* 124, 97-107 (2007).
94. Yang, X. et al. Notch activation induces apoptosis in neural progenitor cells through a p53-dependent pathway. *Dev Bio* 1269, 81-94 (2004).
95. Waters, A. M. et al. Ectopic notch activation in developing podocytes causes glomerulosclerosis. *J Am Soc Nephrol* 19, 1139-1157 (2008).
96. MacDonald, B. T., Tamai, K. & He, X. Wnt/beta-catenin signaling: components, mechanisms, and diseases. *Dev Cell* 17, 9-26 (2009).
97. Hayward, P., Kalmar, T. & Arias, A. M. Wnt/Notch signalling and information processing during development. *Development* 135, 411-424 (2008).
98. Wang, Y. Z. et al. Activation of the Wnt/beta-catenin signaling reporter in developing mouse olfactory nerve layer marks a specialized subgroup of olfactory ensheathing cells. *Dev Dyn* 237, 3157-3168 (2008).
99. Rodriguez-Gil, D. J. & Greer, C. A. Wnt/Frizzled family members mediate olfactory sensory neuron axon extension. *J Comp Neurol* 511, 301-317 (2008).
100. Booker-Dwyer, T., Hirsh, S. & Zhao, H. A unique cell population in the mouse olfactory bulb displays nuclear beta-catenin signaling during development and olfactory sensory neuron regeneration. *Dev Neurobiol* 68, 859-869 (2008).
101. Brault, V. et al. Inactivation of the beta-catenin gene by Wnt1-Cre-mediated deletion results in dramatic brain malformation and failure of craniofacial development. *Development* 128, 1253-1264 (2001).
102. Harada, N. et al. Intestinal polyposis in mice with a dominant stable mutation of the beta-catenin gene. *Embo J* 18, 5931-5942 (1999).

Example 2

The ability of the olfactory epithelium (OE) to regenerate after injury is mediated by at least two populations of presumed stem cells—globose basal cells (GBCs) and horizontal basal cells (HBCs). Of the two, GBCs are molecularly and phenotypically analogous to the olfactory progenitors of the embryonic placode (OPPs). In contrast, HBCs are a reserve stem cell population that appears later in development and requires activation by severe epithelial damage before contributing to epithelial reconstitution. Neither HBC emergence nor the mechanism of activation after injury is understood. Here it is shown that the transcription factor p63 (Trp63), which is expressed selectively by adult HBCs, is required for HBC differentiation. The first evidence of HBC differentiation is the expression of p63 by cells that closely resemble embryonic OPPs and adult GBCs by morphology and expression of the transcription factors Sox2, Ascl1, and Hes1. HBC formation is delayed in Ascl1 knockout OE and is completely abrogated in p63-null mice. Strikingly, other cell types of the OE form normally in the p63 knockout OE. The role of p63 in HBC differentiation appears to be conserved in the regenerating rat OE, where HBCs disappear and then reappear after tissue lesion. Finally, p63 protein is down-regulated in HBCs activated by lesion to become multipotent progenitor cells. Here, it is shown that p63 is expressed in differentiating and mature HBCs and is required for their generation during development. Also reported is a cycle of down-regulation and re-expression of p63 during recovery of the adult epithelium from injury that substantiates a role for p63 in the cycle of HBC activation and return to dormancy. Taken together, these results identify a novel mechanism for the generation of a reserve stem cell population and suggest a p63-dependent molecular switch is responsible for activating reserve stem cells when they are needed.

1. p63 Marks Phenotypically Differentiated HBCs.

The OE is a pseudostratified neuroepithelium that consists of olfactory sensory neurons (OSNs), sustentacular (Sus) cells, duct/gland assemblies, microvillar cells, and a set of morphologically and functionally heterogeneous basal cells including HBCs and GBCs (Graziadei and Graziadei, 1979). The lamina propria of the olfactory mucosa contains olfactory ensheathing cells (OECs) that surround the axon fascicles of the OSNs as well as a heterogeneous population of fibroblasts some of which might function as mesenchymal stem cell (MSCs) (Tome et al., 2009, Delorme et al., 2010) (FIG. 1A).

Immunohistochemistry and semiquantitative RT-PCR were performed to analyze p63, K14 and CD54 in HBC. The results demonstrate that ΔNp63 was expressed by HBCs of the adult OE of rat and mouse. All p63(+) cells co-labeled with the HBC marker K14. An occasional cell that was K14 (+), but p63(−) was displaced apically from the layer of mature K14(+)/p63(+) HBCs. All p63(+) cells co-labeled with CD54, another HBC marker. Semiquantitative RT-PCR revealed that ΔNp63 is the only detectable 5' isoform of p63 expressed in the OE. The α and, to a lesser extent, β isoforms, but not the γ isoform are the primary 3' isoforms. Immunohistochemistry of anti-ΔNp63 colocalization with anti-pan-p63 was also performed.

Figure 10A:
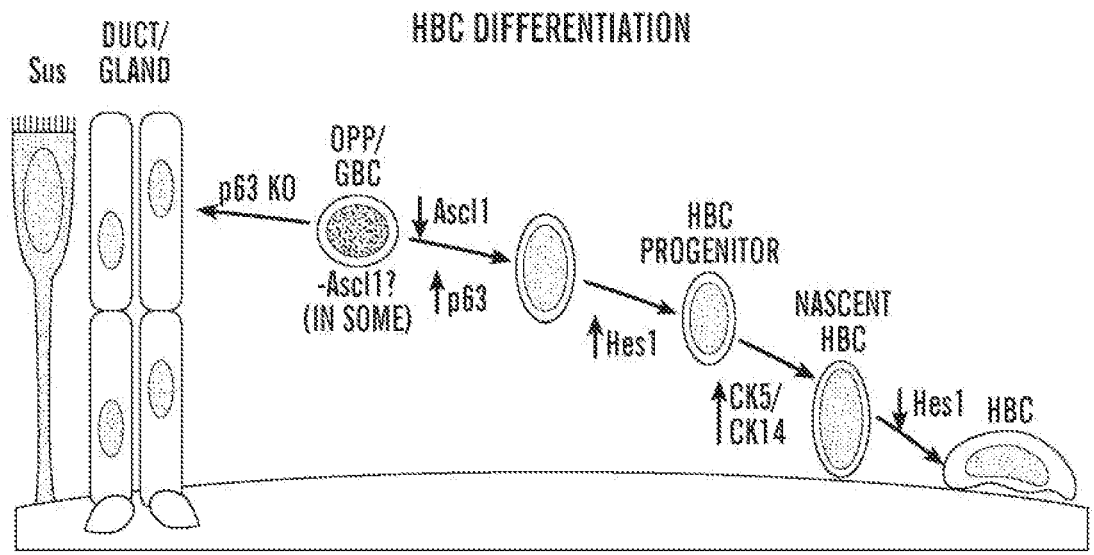
FIG. 10A-FIG. 10B are schematics of HBC development and activation after injury.
Figure 10B:
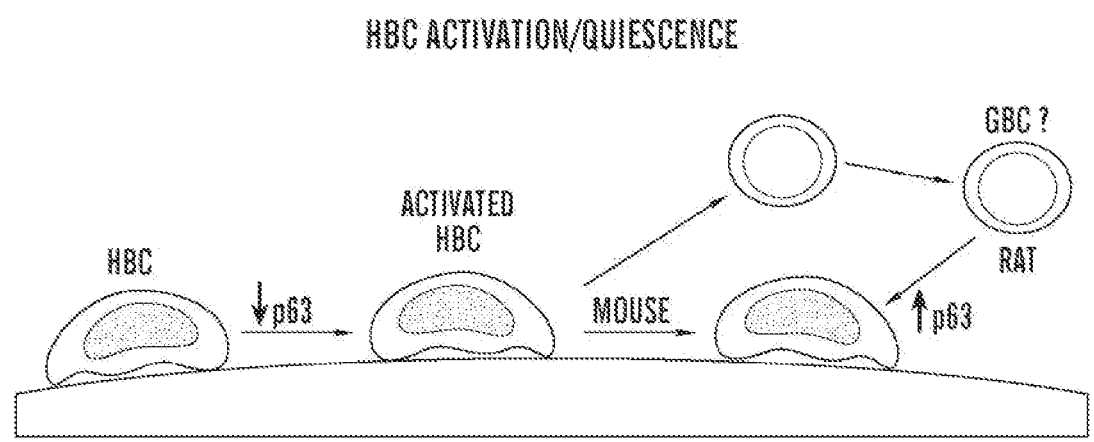

In adult mouse and rat OE it was found that anti-p63 antibodies label the nuclei of basal cells that are immediately apposed to the basal lamina; the p63(+) cells are flat, have scant cytoplasm, and co-label with the HBC markers K14 and CD54 (I-CAM). Rarely, some of the K14(+) HBCs do not contain detectable p63 (FIG. 10B). Such p63(−)/K14(+) cells represent ~4% (8/201) of the total K14(+) cells in the rat and <1% (2/235) in the mouse.

The p63 gene encodes two sets of N-terminal isoforms driven by alternate promoters and 3 different C-terminal isoforms (α, β, and γ) generated by alternative splicing (Yang et al., 1998, Ghioni et al., 2002, Candi et al., 2007). The prevalent N-terminal isoforms present in the basal cells of most stratified epithelia are the ΔNp63 forms, which lack a transcriptional transactivation domain at the 5' end of the gene (Candi et al., 2006). The TAp63 isoforms, which contain the transactivation domain, control CNS development (playing a role in neuronal apoptosis) and female germline maintenance (Jacobs et al., 2005, Suh et al., 2006). Semi-quantitative RT-PCR of RNA isolated from murine whole olfactory mucosa indicates that ΔNp63α and -β are the prevalent isoforms of p63 expressed in the OE; under the same conditions no TA- or γ-isoforms were detected. Immunolabeling with a ΔNp63-specific antibody (Romano et al., 2006) is completely coextensive with pan-p63 antibody staining in the HBCs (FIG. 1F), while a TAp63-specific antibody did not generate any nuclear signal in the OE (Romano et al., 2009)

2. p63 Expression Anticipates Differentiation of HBCs During Embryonic Development Given that HBCs do not appear until the perinatal period when all other cell types of the OE have already emerged, the expression of p63 in the embryonic and early postnatal epithelium was assayed.

Figure 6:
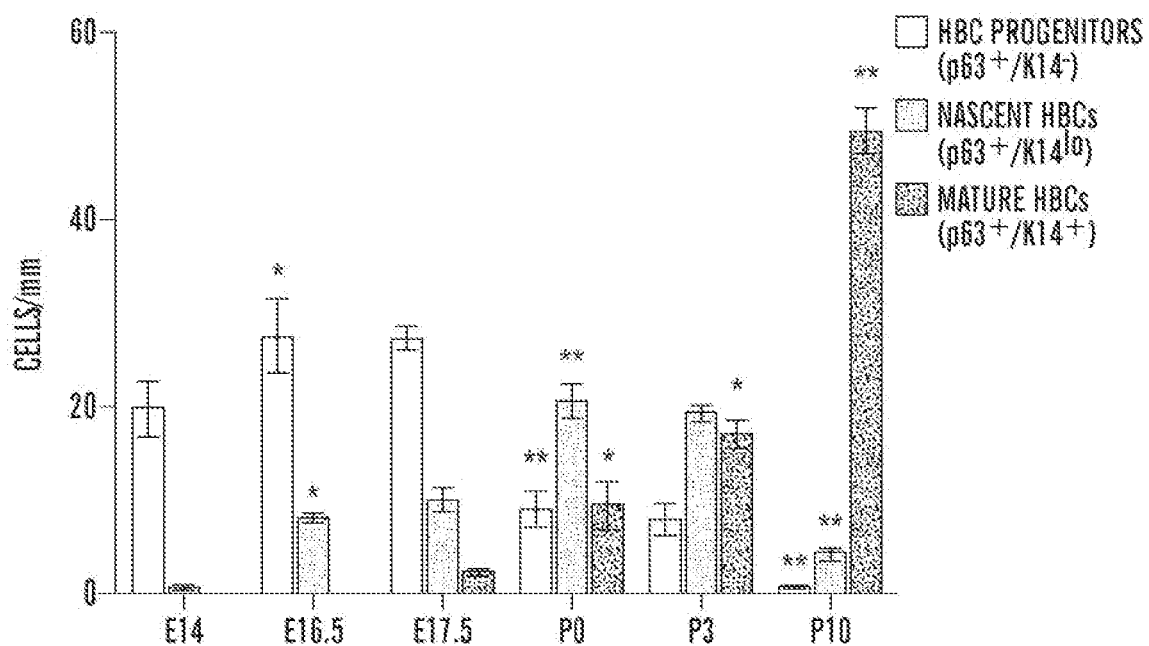
FIG. 6 shows a chart of the quantification of the three stages of HBC development indicating a statistically significant difference as a function of time and cell type (Two-way ANOVA). Asterisks indicate a statistically significant difference (* $p<0.05$, ** $p<0.01$) by comparison with the previous time-point for the cell type indicated.

Immunohistochemistry analysis was performed to visualize p63, K14. This analysis demonstrated that p63 expression anticipates HBC differentiation. Developmental expression of immunopositive p63 in the mouse OE was seen. Apical p63(+)/K14(−) cells (HBC progenitors), were first seen at E14 and persisted into the early postnatal period. By E16.5 some p63(+) cells stained for K14 (nascent HBCs). Mature, p63(+)/K14(+) HBCs, tightly adherent to the basal lamina (mature HBCs), first appear at E17.5 and increased through the first two weeks of post-natal life to form a flattened monolayer by P10 (FIG. 6).

At E12, no p63 labeling is observed in OE. At E14, p63(+) cells are concentrated in the apical reaches of the epithelium; none of them contact the basal lamina. At this stage K14- or K5-labeled cells have yet to appear in the OE. For purposes of classification we designated p63(+)/K14(−) cells as "HBC progenitors" (FIG. 6). At E16.5 the density of "HBC progenitors" was slightly increased compared to E14. In addition, some p63(+) cells were weakly labeled by anti-K14 and K5 (not shown). The nuclei of the p63(+)/K14(+) cells are elongated and parallel the apico-basal axis. Some of these cells abutted the basal lamina, but they were not flattened and lack the high level of K14 expression that is characteristic of mature HBCs. We classified these cells "nascent HBCs" (FIG. 6). At E17.5 the density of "HBC progenitors" and "nascent HBCs" remains constant relative to E16.5. At E17.5 a few "mature HBCs" (defined as flattened cells with abundant K14, adjacent to the basal lamina) were observed. At P0 the density of "HBC progenitors" decreases sharply, while the populations of "nascent HBCs" and "mature HBCs" expanded. At P3, the number of "mature HBCs" continued to increase until P10. By P10 the OE approaches the adult state and contains a monolayer of flattened, K14(+) HBCs at the basal lamina with few if any "HBC progenitors" and rare "nascent HBCs". The time course described above suggests that p63 marks progenitor cells (as indicated in FIG. 6) that will come to express K14 and acquire mature HBC morphology. The appearance in the middle of the apicobasal axis followed by their accumulation at the basal lamina suggests that the p63(+) cells are in transit toward the epithelial base. As the cells that initiate p63 expression are neither at the apex of the developing epithelium, where the dividing OPPs are found, nor yet at the base, where the GBCs reside, we call them OPP/GBCs for convenience.

Figure 5:
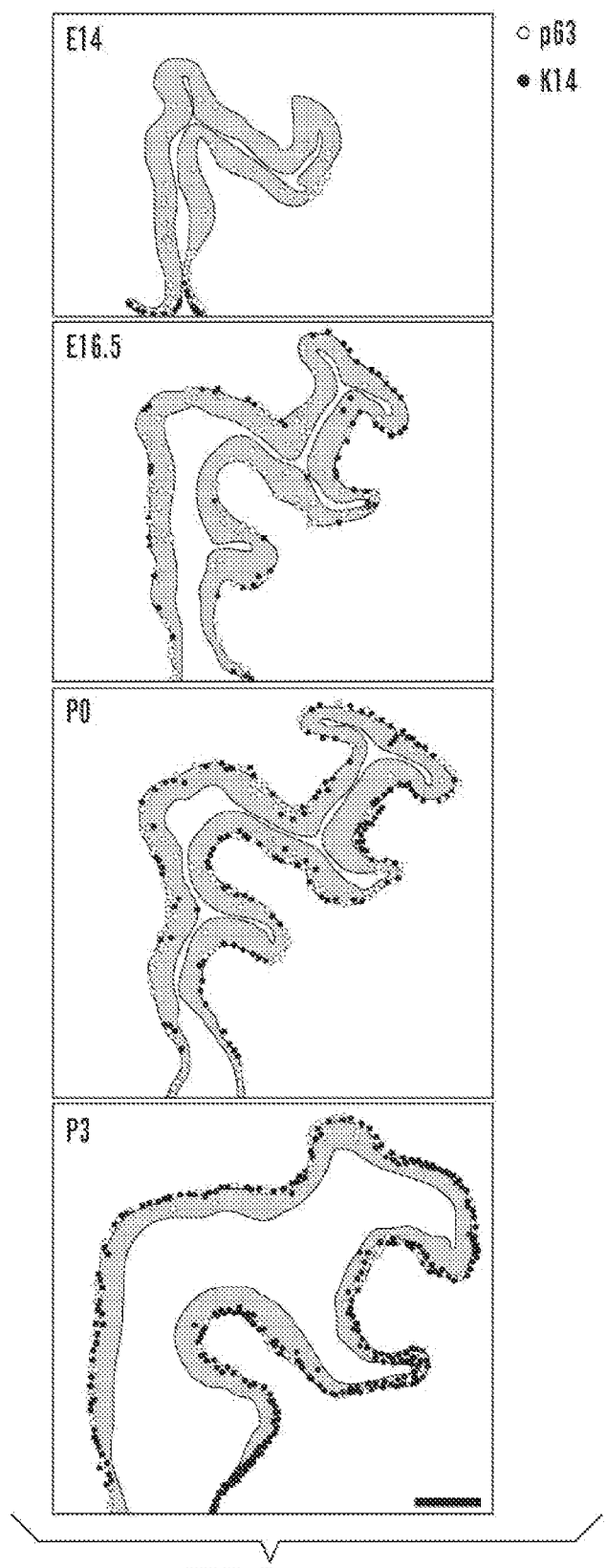
FIG. 5 is an illustration of immunostaining for p63 and K14 in the whole OE at E14, E16.5, P0 and P3. The pattern described is conserved throughout the developing OE, however the dorsal recess lags behind the ventral OE in terms of HBC development. scale bars=100 µm.

A mapping of p63 and K14 expression as they accumulate across the whole OE demonstrated that the aforementioned pattern is representative of HBC development overall (FIG. 5). Interestingly, the ventral OE displayed higher numbers of p63 and K14 expressing cells at earlier time points than the dorsal OE. This was consistent with earlier reports which show that HBC development is delayed in the dorsal vs. ventral OE in rats as well as other accounts of OE embryogenesis (Suzuki and Takeda, 1991, Holbrook et al., 1995).

In sum, the expression of p63 anticipates both molecular (e.g., K5/14 expression) and morphological differentiation of HBCs. The sequence of expression (combined with the role of p63 in maintaining basal cell populations in other epithelia) implicates p63 as a linchpin in the differentiation of this important population of reserve stem cells in the OE.

3. p63 is Expressed Along with Various Molecular Markers of GBCs and OPPs.

Experiments were performed to classify the p63(+) cells of the embryonic OE by comparing p63 expression with other transcription factors characteristic of the progenitor cell types of the OE. First examined was Sox2, a marker common to OPPs and adult basal cells; all of the p63(+) progenitors also label for Sox2 protein. Other markers that co-label with p63 are characteristic of what are believed to be more committed subsets of progenitor cells. For example, a low percentage of p63(+) cells express Ascl1, a bHLH transcription factor usually thought to convey a commitment to neuronal differentiation (Cau et al., 2002). The p63(+)/Ascl1(+) cells are most prominent at E14, becoming scant at E16.5. In contrast, p63 (+) cells that co-label with anti-Hes1 antibodies increase during the same time period. Hes1 is a bHLH transcription factor that is thought to oppose the action of Ascl1 and is characteristic of Sus cells or GBCs differentiating into Sus cells in the normal and regenerating epithelium, respectively. The p63 (+)/Hes1(+) cells are a different population from the p63(+)/Ascl1(+) cells—double-labeling with Ascl1 and Hes1 antibodies stain non-overlapping sets of cells at all stages (data not shown). Nascent and mature HBCs continue to express Hes1 during early postnatal development. While many p63 (+) cells still stain for Hes1 at P10, the intensity of this staining is reduced by comparison with earlier time points and is completely absent by the time the animal reaches adulthood (Manglapus et al., 2004). The co-expression of incipient p63 and heretofore lineage-restricted transcription factors is unexpected and lays the foundation for potential dynamic interactions within the transcriptional network during lineage commitment.

4. p63 Marks Slowly Dividing Progenitor Cells.

Figure 7A:
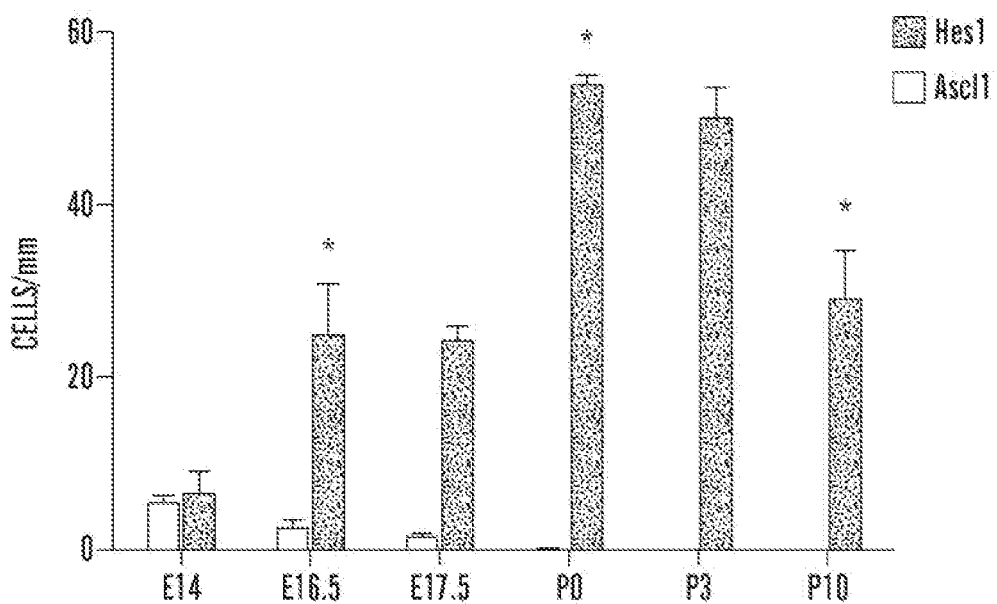
FIG. 7A-FIG. 7C show graphs demonstrating that p63(+) HBC precursors are slow-cycling and express markers of OPPs and GBCs.
Figure 7B:
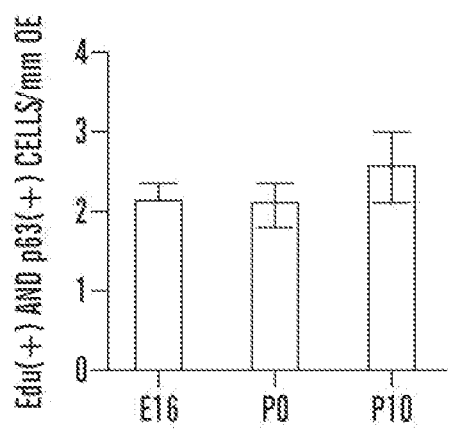
Figure 7C:
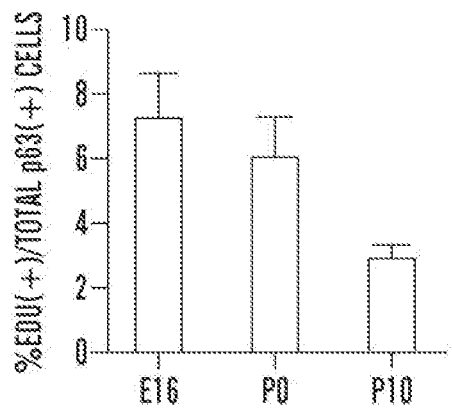

HBCs in the adult OE are slow cycling cells with ~2 dividing HBCs/mm OE dividing under homeostatic conditions (Leung et al., 2007). Proliferating cells were labeled acutely with the thymidine analog EdU at E16, P0, and P10. Throughout the perinatal time-course of HBC development, there is no significant difference in the number of p63(+)/EdU(+) cells/ mm OE (~2 cells/mm OE) (FIG. 7B). Since there are fewer p63(+) cells early in development also analyzed were the percentage of the total number of p63(+) cells that are EdU (+). The percent of EdU(+)/p63(+) cells trends downward during development, approaching statistical significance (p=0.06, One-way ANOVA, Kruskal-Wallis statistic=5.600) (FIG. 7C). The apparent trend may be due to a higher number of cells with newly-acquired expression of p63. Such cells may have incorporated EdU before they expressed p63. These data suggest that p63(+) HBC progenitor cells become slow cycling before their full differentiation into mature HBCs.

5. Ascl1 Knock-out Causes a Delay in the OE in p63 Expression and HBC Differentiation.

To test the hypothesis that p63(+) HBC progenitors might pass through a phase of Ascl1 expression we analyzed the embryonic development of Ascl1(−/−) OE using a ΔMash1-GFP knock-in line (Wildner et al., 2006). It has recently been observed a lag in HBC differentiation in the OE of Ascl1 knockout (KO) embryos, but no delay in Ascl1 heterozygous (Het) as compared to wildtype (WT) mice (Krolewski, Packard, Jang, and Schwob).

Immunohistochemistry visualizing p63 and K14 was performed and demonstrated that p63 expression and HBC differentiation are delayed in Ascl1 KO OE. p63 expression was unchanged from normal at the borders between OE and respiratory epithelium. At E14.5, p63(+)/K14(−) HBC progenitors were present in Ascl1 Het, but not KO OE. At E18.5, many p63(+)/K14(+) nascent and mature HBCs were present in the Het, but not KO OE where some p63(+)/K14(−) HBC progenitors were just beginning to appear. At P0, many mature HBCs were present in the Het, but not KO OE.

Here it is shown that p63 expression in the KO also lags by comparison with the Ascl1 WT or Het epithelium. At E14.5, p63(+) cells cannot be detected in the Ascl1 knockout OE in contrast to the sizeable population of p63(+) cells in the Ascl1 Het littermates. At E18.5, the KO OE still contains very few p63(+) cells, while the Het OE has robust p63 and K14 expression, which parallels the developmental increase seen in the C57/B6 strain described earlier. At P0, there are only a few p63(+)/K14(+) cells in the KO, as opposed to the large population of fully differentiated and differentiating HBCs in the Het OE. Thus, while HBCs do eventually form in Ascl1 KO animals, there is a substantial delay in their appearance, suggesting an alternate, Ascl1-independent, pathway to HBC development.

6. p63 is Required for Timely Morphological and Molecular Differentiation of HBCs.

To test whether p63 is an essential factor regulating HBC differentiation, next p63 KO mice were analyzed in which the p63 gene was disrupted via retroviral insertion into the coding sequence of the gene (Mills et al., 1999). Immunohistochemistry analysis was performed to visualize p63, CK14, CD54 and Col IV. This analysis demonstrated that p63 KO prevents the development of HBCs at P0. p63 wild-type OE displayed normal development of p63(+)/K14(+) HBCs, comparable to the parent C57/B6 line used in the above described experiments. p63 heterozygous OE displayed reduction in p63(+) cells and a delay in HBC formation. p63 knockout OE contained no p63(+)/K14(+) HBCs. In WT OE, CD54, another marker of HBCs, was expressed by K14(+) cells, i.e. cells above the basal lamina (marked by type IV collagen). No CD54 staining was observed in the knockout OE above the basal lamina. Cells within the lamina propria accompanying capillary loops as they traversed the epithelium were CD54 (+).

Because the KO mice die soon after birth due to severely compromised skin development, KO, Het, and WT animals were analyzed as they were born. At this time point, K14 expression in the OE of p63 KO mice is not readily detectable. p63(+) HBCs are evident in the OE of the p63 Het littermates, but are reduced in number to 41% (+9%) of WT, suggesting that HBC development is delayed due to haploinsufficiency. The OE of p63 KO mice also lacks detectable levels of another early HBC marker, CD54 (ICAM). The absence of p63 in the KO animals does not prevent expression of K14 and CD54 in other cell types: CD54-labeled cells are evident within the lamina propria and basal lamina-delimited capillary loops that extend into the OE. K14 is expressed by patches of cells within the tongue epithelium of the knockout mice. Taken together the data suggest that timely morphological and molecular HBC differentiation is absent in the OE of the p63-null mice.

To confirm that the lack of marker expression indicates an absence of morphologically distinct HBCs we assessed the basal population of the p63 WT vs. KO OE by transmission electron microscopy. The electron microscopy confirmed the absence of morphologically distinct HBCs in p63 KO OE. WT OE contained cells with flattened HBC morphology and focal attachments to the basal lamina. These cells arched over bundles of olfactory axons. A primary cilium (PC) was visible on a dividing GBC. In No HBCs were evident in p63 KO OE, in contrast to WT. Instead, GBCs were directly apposed to, but did not form focal attachments onto, the basal lamina. GBCs did not arch over axon bundles.

WT OE contains flat cells with scant cytoplasm and foot processes that contact the basal lamina, consistent with past ultra-structural analysis of HBCs (Graziadei and Graziadei, 1979, Holbrook et al., 1995). In keeping with past reports (ibid), these HBCs arch over bundles of axons. Cells with these morphological characteristics are not found in the p63 KO. Instead, we see round cells, some of which touch the basal lamina, but do not form foot processes. Furthermore, axon bundles in the OE of p63 KO mice are not covered over by the arching processes of basal cells as they are in the WT. Taken together this data demonstrate that p63 is necessary for differentiation of HBCs from a placodally-derived progenitor population.

18L Immunohistochemistry was performed to visualize Tuj, K18, Sox9, Gap43, OMP, Hes1, Ascl1, and Type IV collagen in WT and p63 KO OE. The analysis demonstrated that with the exception of the HBCs, the cell types and epithelial architecture emerge normally in the p63 KO OE. Both WT and KO OE contained Tuj1(+) neurons and K18(+) Sus cells. K18 also marked Bowman's ducts/glands. In the WT these cells extended into the lamina propria as mature glands. In the KO, K18(+) cells were frequently bunched above the basal lamina. Sox9, another marker of duct/gland cells, was expressed in normal glands in the lamina propriat of the WT mucosa. In the KO, piles of Sox9(+) cells accumulated above the basal lamina in the epithelium proper. Neurons in WT and KO OE were roughly equivalent in the proportion of immature OSNs (GAP43[+] and basally situated) vs. mature OSNs (OMP[+]). Sox2 was expressed in Sus cells of WT and KO OE. In the basal cell compartment, fewer Sox2(+) cells were seen in the KO than in the WT. In Fewer Hes1(+) cells were present in the basal OE of p63 KO OE. Ascl1(+) cells are equally abundant in WT and KO OE. Type IV collagen marked the basal lamina.

Strikingly, the other cellular constituents of the OE are grossly normal in the p63 KO, including neurons (expressing neuron-specific tubulin and labeled with Tuj1), cells of Bowman's glands and ducts (expressing Sox9 and K18), and Sus cells (expressing Sox2 and K18). The neuronal population in the KO OE can be subdivided into mature, OMP(+), and immature, GAP43(+), groups in roughly the same number and proportion as WT OE, indicating that neurogenesis is not disrupted by p63 knockout. Moreover OMP(+) olfactory axons fill the glomeruli of the olfactory bulb in the KO mice, suggesting that the bulb is also innervated more or less appropriately in the absence of p63. A subtle abnormality in the development of Bowman's glands and ducts was observed. Whereas the glands/ducts project well into the lamina propria of the WT OE at birth, their extension below the basal lamina is stunted in the KO mucosa. In the KO mice, some glands push into the lamina propria, but Sox9(+)/K18(+) cells with gland morphology are often clustered in the OE superficial to the basal lamina (marked by Type IV collagen). Clusters like this are rarely if ever seen in the WT OE. Since p63 can regulate production of components of the basal lamina in the epidermis, it is possible that the absence of HBCs may cause defects in the olfactory basal lamina that may inhibit proper extension of gland cells into the lamina propria during development (Koster et al., 2007).

The presence of progenitor cell populations in the knock-out OE was also assayed using the markers described earlier. Sox2 protein was expressed in the Sus and basal cells of p63 KO OE, however the number of Sox2(+) cells was diminished in the KO compared to WT. Since HBCs are Sox2(+), this decrease can be accounted for by the absence of HBCs in the KO described above. Similarly, fewer basal cells in the p63 KO OE expressed Hes1, which is still expressed in developing HBCs at this stage. Expression of Ascl1 and of NeuroD1, markers of early and late neural precursor cells, respectively, did not significantly differ between knockout and wild-type animals. In addition, the expression of CD190, Thy1, and vimentin was examined to assess the status of the fibroblastic cells of the lamina propria and of brain lipid-binding protein for the olfactory ensheathing cells, respectively. This examination of the former set of markers was motivated by recent demonstrations that a stem-like cell is present within the mesenchymal elements deep to the OE. However, no difference was observed between the KO and wild-type with regard to the distribution of these cell types, nor the rate of their proliferation.

7. p63 is Required Specifically for HBC Differentiation and not for Release of OPP/GBCs from an Immature Phenotype.

There are two likely interpretations of the data thus far: (1) p63 is required to actively drive the differentiation of HBCs from a subset of OPP/GBCs induced to express p63 by unknown mechanism(s). (2) p63 is required to release a subclass of OPP/GBCs from an immature state, and allow them to differentiate. In the first case, OPP/GBCs induced to express p63 in the knock-out would simply adopt an alternate cell fate. In the second case any OPP that might be induced to express p63 would not differentiate and would instead remain immature. To distinguish between these possibilities analyzed a ΔNp63 knock-in mouse model was analyzed in which the ΔNp63 specific exon has been replaced by the Green Fluorescent Protein (ΔNp63GFP). Homozygous mice are thus null for the ΔNp63 gene product, but retain expression of TAp63. In the OE, skin, and limbs, among other tissues, the ΔNp63GFP−/− mice phenocopy the mutant mouse strain presented above, in which both forms are eliminated, once again validating the criticality of the ΔNp63 isoform vs. TAp63 in the OE.

To determine the cell fate of OPP/GBCs that are pushed to express ΔNp63, but cannot do so as a result of gene deletion, we analyzed GFP perdurance in the ΔNp63GFP−/− OE at E18.5. Immunohistochemistry was performed to visualize GFP, CK18, and Sox2. This analysis demonstrated that OPP/GBCs differentiated into non-neuronal subtypes in the absence of p63. The OE of the ΔNp63-GFP−/− contained GFP(+)/CK18(+) cells that resembled Sus, duct and Bowman's gland cells. However, some of the GFP(+) cells lacked CK18 and were situated basal to the layer of Sus cells and most likely corresponded to OPP/GBCs that had more recently attempted to express the null □Np63GFP locus and had not yet had the time to differentiate further to Sus or duct/gland cells. GFP(+) cells with Sus morphology were Sox2(+), while GFP(+) cells with the flattened shape of duct cells or the acinar arrangement of gland cells were Sox2(−), just like the mature cell types. GFP(+) cells were PGP9.5(−), suggesting that the GFP-marked OPPs were committed to a non-neuronal lineage.

It was found that the majority of GFP(+) cells at this age are CK18(+) and have the morphology of either Sus or Bowman's gland cells. The GFP(+) Sus cells were Sox2(+), while the GFP(+) gland cells are Sox2(−), which are their marker profiles in the normal OE. Interestingly, none of the GFP(+) cells stained for PGP9.5 or Tuj1, suggesting that these OPP/GBCs are committed to a non-neuronal lineage. Some GFP (+) cells did not resemble Sus or gland cells and did not express the neuronal markers PGP9.5 or Tuj1, suggesting that a subset of OPP/GBCs is still driven to express the ΔNp63 locus at this age. Taken together, the data strongly suggest that p63 functions actively to drive HBC differentiation of a progenitor committed to making non-neuronal cells, rather than passively to release OPP/GBCs from an uncommitted, immature state.

8. Recovery of Ventral Rat OE Recapitulates the Developmental Sequence of HBC Formation.

The rodent OE is lesioned by passive inhalation of the olfactotoxic gas methyl bromide (MeBr) (Schwob et al., 1995). MeBr destroys the differentiated cells (neurons, Sus cells, microvillar cells) of the OE, but spares a heterogeneous population of basal progenitor cells, truncated ducts and damaged Bowman's glands. The remaining cells are able to reconstitute the epithelium fully in 2-3 weeks. However, the response of HBCs to the toxin is subtly different in rat vs. mouse OE, which provides an analytic advantage. It has previously been shown that the ventral domain of the MeBr-lesioned rat OE becomes almost completely devoid of K5/14 (+) HBCs by 1-3 days after exposure (Schwob et al., 1995). The HBCs then reappear progressively between 3-14 days post-lesion (dpl). As such, regeneration of the ventral rat OE after lesion recapitulates development.

Immunohistochemistry was performed to visualize P63, K14. The images and cell counts demonstrated that p63 expression anticipates HBC differentiation in the regenerating ventral rat OE. Normal rat OE contained p63(+)/K14(+) HBCs. At 1 day post MeBr lesion (dpl) few if any p63(+) or K14(+) cells remained evident in the ventral part of the OE. As early as 3 dpl p63(+) cells could be observed at a remove from the basal lamina. At 5 dpl the population of HBC precursors expanded. These precursors were rarely void of K14 protein, but frequently expressed K14 at a lower level than mature HBCs. At 7 dpl HBC precursors were still settling down on the basal lamina.

As expected, the number of p63(+)/K14(+) cells (HBCs) in the ventral OE dropped off at 1 and 3 dpl as compared to normal OE. As regeneration proceeded from 3 to 5 dpl, p63 (+)/K14(−) cells (HBC progenitors) appeared, although they were less numerous than during embryonic development. Instead, most nascent p63(+) cells express low levels of K14, suggesting that these cells were much quicker to express HBC cytokeratins than embryonic HBC progenitors. Because it was difficult to discriminate cells that lack K14 expression from those with very low levels of K14-labeling, p63(+)/K14

Figure 8:
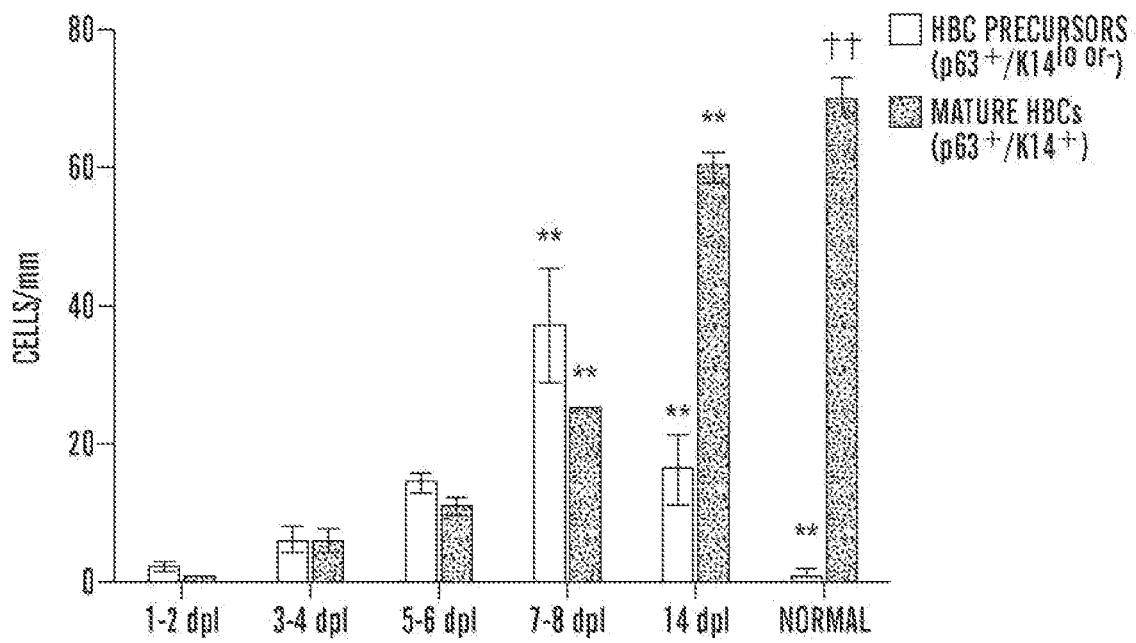
FIG. 8 is a chart depicting counts of differentiating HBCs during regeneration of the ventral rat OE are significantly different as a function of time and cell type (Two-way ANOVA). Asterisks indicate a statistically significant difference (** $p<0.01$) by comparison with the previous time-point for the cell type indicated. Daggers indicate that normal OE is significantly different from 1-2 dpl OE (†† $p<0.01$).

(−) and p63(+)/K14(weak) cells were grouped into a single category for purposes of the quantitative analysis (FIG. 8). These "HBC precursors" increased in number during the first 1.5 weeks of regeneration until a nearly mature HBC layer is re-established by 2 weeks post-lesion (FIG. 8). These data further validate a role for p63 in maintaining a reserve stem cell population within the cellular dynamics of the OE.

9. p63 is Transiently Down-regulated in the Regenerating OE

Cell counts and immunohistochemistry was performed to visualize p63 and K14 levels. This analysis demonstrated that p63 protein levels are transiently down-regulated after MeBr lesion in the mouse. p63 and K14 stained in normal mouse HBCs. At 1 dpl K14(+) cells were flat and directly apposed to the basal lamina, but had lower levels of p63 staining (activated HBCs, white arrows). At 2 dpl, a second layer of K14(+) cells were found apical to the usual HBC layer. The apical cells were p63(−), while many of the basal-most K14(+) cells had regained p63 protein expression. At 3 dpl the apical layer of K14(+)/p63(−) cells had expanded, while all of the basal-most K14(+) cells expressed high levels of p63 protein. By 7 dpl there were fewer activated HBCs. Most of the K14(+) cells now sat directly on the basal lamina and expressed high levels of p63 protein.

Figure 9:
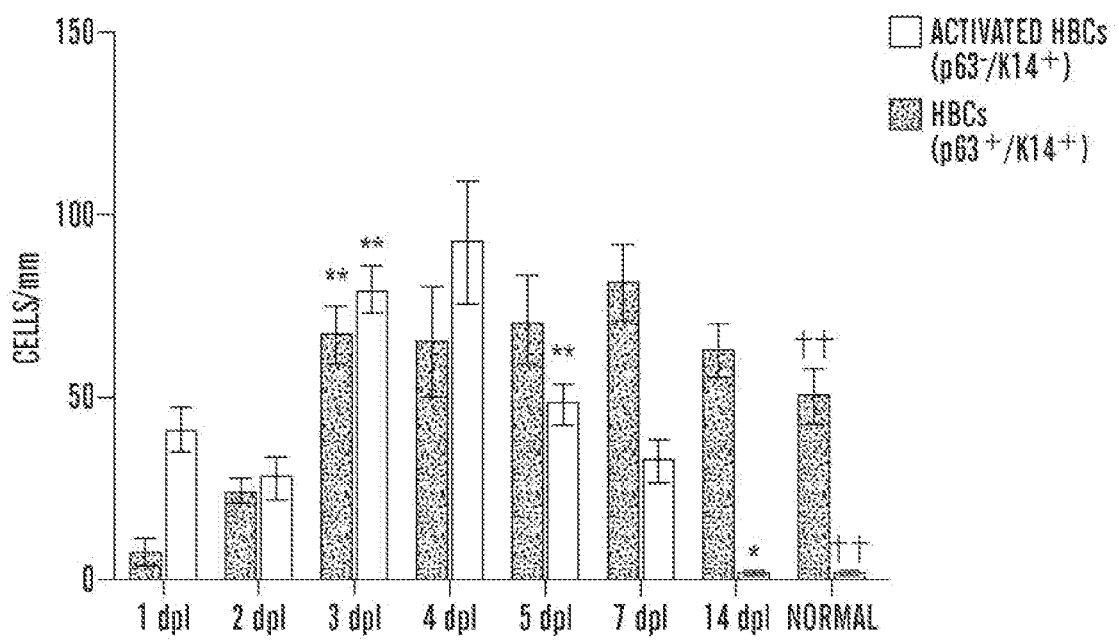
FIG. 9 is a chart of counts of normal (p63+/K14+) and activated (p63−/K14+) HBCs in the recovering mouse OE. Asterisks indicate a statistically significant difference (* $p<0.01$, ** $p<0.01$, Two-way ANOVA) by comparison with the previous time-point for the cell type indicated. Likewise, normal OE is significantly different from 1-2 dpl OE (†† $p<0.01$).

In contrast to the ventral OE of the rat, the mouse OE retains K14(+) basal cells after MeBr lesion. However, it was found that at 1 dpl many of these K14(+) cells are more lightly stained for p63 as compared with normal OE. Because down-regulation of p63 levels appears to be a direct consequence of MeBr lesion we categorized the p63(−)/K14(+) cells in our quantification as "activated HBCs", while the p63(+)/K14(+) cells were classified as "quiescent HBCs". At 2 dpl K14(+) cells no longer form a monolayer but have accumulated to several cell layers thick. At this time, some K14(+) basal cells have regained expression of p63, but many more apically situated K14(+) cells are p63(−). At 3 dpl all of the basal-most cells of the regenerating OE strongly express p63, while the more apical p63(−)/K14(+) layer continues to expands. The population of p63(−)/K14(+) cells remains prominent until 5 dpl, when their number begins to drop off. This drop-off continues 7-14 dpl until there are few if any p63(−)/K14(+) cells present in the tissue (FIG. 9).

10. Summary

These results demonstrate that p63 is a key player in the emergence of HBCs during development. The first definitive HBCs—p63(+)/K14(+) cells apposed to the basal lamina—appear in the mouse OE at E17.5. Their formation accelerates after birth and the HBC layer reaches confluency by P10. These data closely match prior descriptions in the rat (Holbrook et al., 1995). Expression of p63 anticipates the appearance of definitive HBCs in the embryo; p63(+) cells at this stage are slow-cycling, Sox2(+), GBC-like, HBC progenitors some of which are marked by Ascl1 at an early stage and many of which express Hes1 later (FIG. 10A). Moreover, HBCs do not form in the absence of p63. We also show that p63's role in driving HBC differentiation in the OE appears to be conserved well into adult life. In the regenerating ventral rat OE, p63 expression recapitulates development by anticipating the re-appearance of dormant HBCs. Conversely, we provide evidence suggesting that down-regulation of p63 protein by mature HBCs is a hallmark of their activation to multipotency (FIG. 10B).

It is demonstrated herein that p63 is expressed by and required for basal cells of a tissue, but is dispensable for the generation of all other cell types. In contrast, loss of p63 expression elsewhere (specifically the ΔNp63 form, as in the OE) prevents the formation of normal epithelia. For example, in addition to the disruption of the epidermis, the prostatic bud, the thymic anlage, and the breast buds do not form in p63-null mice, nor is there squamous differentiation of the utero-vaginal junction (Mills et al., 1999, Yang et al., 1999, Crum and McKeon, 2010). These developmental abnormalities are commonly attributed to a failure to form and/or maintain the basal cells of these tissues (Candi et al., 2007, McKeon and Melino, 2007, Su et al., 2009). These results in the OE suggest that p63 is a prerequisite for the differentiation of a typical basal cell phenotype (flat cells directly apposed to the basal lamina with strong K5/14 and CD54 expression), but does not direct the generation of the entire tissue. In settings where cytokeratin-positive basal cells are obligate progenitors from which the tissue forms, loss of p63 aborts tissue development. However, the cytokeratin-positive HBCs of the OE (a pseudostratified epithelium) emerge later in development, after most of the architecture of the mature tissue has been assembled.

The p63(+) HBC progenitors were further characterized using a wide array of markers associated with OPPs and GBCs. In addition to a marker of multipotent GBCs and OPPs (Sox2) it was found that HBC progenitor cells also express factors that are usually associated with lineage commitment, Ascl1 (commitment to neuronal lineage) in small number and Hes1 (commitment to Sus cell lineage) in a greater proportion. Moreover, the p63(+) cells may be transitioning from Ascl1 expression to Hes1 expression (which persists in association with p63 and K14 during the first days of life). The substantial delay in p63 expression and HBC differentiation in Ascl1 KO OE might reflect a lineage whereby most HBCs develop from Ascl1(+) precursor cells that transition to express p63 and Hes1. However, HBCs do emerge to some extent in Ascl1 KO OE, indicating that passage through an Ascl1(+) progenitor is not an obligatory step in the differentiation of HBCs.

Past work suggests that HBCs function as a reserve progenitor/stem cell population capable of replenishing all the cell types of the epithelium throughout post-natal life (Holbrook et al., 1995, Carter et al., 2004, Leung et al., 2007, Iwai et al., 2008). However, their multipotency remains largely dormant, i.e. they are incapable of engraftment following transplantation and give rise only to themselves, for the most part, unless activated by severe epithelial injury (Chen et al., 2004, Leung et al., 2007). Here it is shown that the sequential down- and then up-regulation of p63 expression is tightly linked to the cycle of HBC activation and return to dormancy. These findings in the MeBr lesioned-recovering OE parallel observations in skin demonstrating that the transition from basal to suprabasal compartments is mediated by down-regulation of p63 via miR-203 expression (Lena et al., 2008, Yi et al., 2008). Likewise, wound healing in humans is accompanied by a transient down-regulation of p63 expression at the leading edge of the wound (Noszczyk and Majewski, 2001).

While the molecular mechanisms of the basal to suprabasal phenotypic shift are not fully understood, even in epidermis, p63 down-regulation appears to be required (Yi et al., 2008). Direct targets of p63 in other epithelial tissues regulate cell adhesion, signal transduction components, and cell cycle regulators. Loss of expression of these molecules would allow basal cells to detach, migrate, and participate vigorously in regeneration and wound healing (Carroll et al., 2006, Yang et al., 2006, Thepot et al., 2010, Yalcin-Ozuysal et al., 2010). While the genes regulated by p63 in developing and adult HBCs are currently unknown, the potential downstream targets identified in other systems may be relevant to HBC dynamics as well. In this study we have looked at a number of genes already known to be direct targets of p63 including K5/14, CD54 (ICAM), and Hes1 (Kikuchi et al., 2004, Nguyen et al., 2006, Romano et al., 2009). The initial expression of Hes1 (a gene that is directly repressed by p63 in keratinocytes; Nguyen et al., 2006) followed by its down-regulation during HBC maturation, illustrates that p63 targets can be dynamic even within a single tissue. Interestingly, it has been found that another p63 target, Notch1, is expressed in adult HBCs.

p63 has been identified as a key transcription factor that may control the transition between stem cell types: p63 expression anticipates formation of the HBC reserve stem cell population, and p63 down-regulation anticipates the activation of HBCs, seemingly back to GBCs. The OE of anosmic humans is characterized by swathes of aneuronal OE that apparently lack GBCs but still retain HBCs (Holbrook et al., 2005). Similarly aneuronal OE is observed in a transgenic mouse model where OMP-driven misexpression of the SV40 T-antigen oncogene likely causes accelerated turnover (Largent et al., 1993). In these settings HBCs have not been activated, and apparently cannot contribute to normal repair of the aneuronal tissue. Such activation might be accomplished by down-regulating p63 in the OE of these patients.

11. Materials and Methods

Animal Strains. Adult SD (Sprague-Dawley) rats were purchased from Taconic. Wildtype C57/B6 mice from Jackson Labs were used to analyze embryonic expression of p63. C57/B6 mice were mated to 129S1/Sv1MJ (Jackson) to produce the F1 progeny used in MeBr lesion experiments. Generation of ΔMash1-GFP (Ascl1 KO) knock-in mice and B6.129S7-Trp63tm2Brd/J (Brdm2 p63 KO) mice has been previously described (Mills et al., 1999, Wildner et al., 2006). To generate $\Delta Np63^{GFP}$ knock-in animals, we engineered a targeting construct containing genomic sequences located 5' and 3' to the ΔNp63-specific exon in order to facilitate homologous recombination. The EGFP gene was fused in-frame to the codon that is specific for the ΔN isoform of the p63 gene to preserve as closely as possible the endogenous regulation of ΔNp63 at the transcriptional level. Additionally, a neomycin resistance gene (PGK-neo) flanked by FRT sites and the diphtheria toxin gene was used for selection in 129Sv embryonic stem (ES) cells. Two correctly targeted ES clones were identified by southern blotting and PCR. The selection and expansion of the ES cell clones were performed by the Gene Targeting and Transgenic Core Facility at Roswell Park Cancer Institute (RPCI). We used $\Delta Np63^{GFP}$ ES cells to generate chimeras that were then bred to C57/BL6 mice to obtain germline transmission. The heterozygous $\Delta Np63^{GFP}$ offspring were subsequently crossed to generate homozygous $\Delta Np63^{GFP/GFP}$, $\Delta Np63^{GFP}$, and wild-type mice for analysis.

Tissue Processing for Immunohistochemistry. Pregnant dams were euthanized by cervical dislocation. Embryos were harvested and staged based on crown-rump length and Theiler criteria. The embryos were immersion-fixed in 4% paraformaldehyde (PFA) overnight. Neonates (up to P3) were euthanized by rapid decapitation and immersion-fixed in 4% PFA overnight. All rats and mice P10 and older were anaesthetized with an IP injection of triple cocktail of ketamine (37.5 mg/kg), xylazine (7.5 mg/kg), and acepromazine (1.25 mg/kg). Anaesthetized animals were transcardially flushed with PBS and perfused with 4% PFA. After dissection the tissue was post-fixed in 4% PFA under vacuum and decalcified in saturated EDTA overnight. All tissue was cryoprotected in 30% sucrose in PBS, embedded in OCT compound (Miles Inc., Elkhart, Ind.), and frozen in liquid nitrogen. 8 μm coronal sections were generated on a Leica cryostat, mounted on "Plus" slides (Fischer Scientific) and stored at −20° C. until needed.

RT-PCR. Cells of the olfactory mucosa were dissociated and FACS-sorted for viability on the basis of propidium iodide exclusion (Chen et al., 2004). RNA was isolated from 106 viable cells using the ZymoResearch DNA-free RNA purification kit. To generate cDNA, 50 ng of RNA were reverse transcribed using SuperScript III reverse transcriptase (Invitrogen). A no-RT control was also performed with 50 ng RNA. cDNA was subjected to PCR using primers and conditions as described (Nakamuta and Kobayashi, 2007).

Immunohistochemistry. Primary antibody dilutions and the details of their working conditions and detection are listed in Table 3. Tissue sections were rinsed in PBS to remove OCT, puddled with citrate buffer, and steamed for 10 minutes in a commercial food steamer. Sections were blocked with 10% donkey serum/5% non-fat dry milk/4% BSA/0.1% TritonX-100 in PBS and incubated overnight in primary antibody. The following day the staining was visualized using an array of methods as indicated in the table. Unless otherwise indicated, blue represents the nuclear counterstain DAPI. A variety of fluorophores (fluors) were used. Green: Alexa-488. Red: Alexa-594 (epifluorescence) or Cy3 (confocal). Blue: AMCA. Alexa conjugated secondary Abs were used at 1:250. Cy3 conjugated reagents were used at 1:150 for directly conjugated secondary antibodies or 1:750 for TSA. AMCA was used at 1:100. Rb—Rabbit. Mo—Mouse. Gt—Goat. TSA—Tyramide Signal Amplification Kit from Perkin Elmer. b—Biotinylated secondary antibody.

TABLE 3

Antibodies and staining protocols used in this study.

| Primary Antibody | Source/Vendor | Protocol | Cell Type(s) Marked |
|---|---|---|---|
| Rb α-CK14 | Labvision (Fremont, CA) | (1:500) → fluor-DαRb | HBCs |
| Rb α-CK18 | Abcam (Cambridge, MA) | (1:300) → fluor-DαRb | Sus and Duct/Gland cells |
| Gt α-mouse CD54 | R&D (Minneapolis, MN) | (1:100) → fluor-DαGt | HBCs |
| Gt α-Collagen Type IV | Southern Biotech (Birmingham, AL) | (1:25) → fluor-DαGt | Basal lamina |
| Rb α-GAP43 | Epitomics (Burlingame, CA) | (1:100) → fluor-DaRb | Immature >> Mature Neurons |
| Rb α-GFP | Abcam (Cambridge, MA) | (1:1,000) → fluor-DaRb | GFP |
| Rb α-Hes1 | T. Sudo (Ito et al., 2000) (gift) | (1:10,000) → TSA → fluor-SA | GBCs (Sus progenitors), Sus, Duct/Gland cells |

TABLE 3-continued

Antibodies and staining protocols used in this study.

| Primary Antibody | Source/Vendor | Protocol | Cell Type(s) Marked |
|---|---|---|---|
| Mo α-Mash1 (Ascl1) | BD Pharmingen (San Jose, CA) | (1:2000) → TSA → fluor-SA | GBCs (neuronal progenitors) |
| Gt α-OMP | Wako (from Frank Margolis) (Richmond, VA) | (1:120) → fluor-DαGt | Mature OSNs |
| Mo α-p63 | Santa Cruz (Santa Cruz, CA) | (1:200) → fluor-DαMo | HBCs, HBC progenitors, nascent HBCs. All p63 isoforms. |
| Rb α-ΔNp63 (RR14) | S. Sinha (Romano et al., 2006) | (1:50) → fluor-DαRb | HBCs, HBC progenitors, nascent HBCs. Specific for ΔNp63. |
| Rb α-PGP9.5 | Ultraclone (Burlington, NC) | (1:1200) → fluor-DαRb | All neurons |
| Gt α-Sox2 | Santa Cruz | (1:80) → b DαGt → fluor-SA | Sus cells, HBCs, GBCs |
| Rb α-Sox2 | Cell Signaling Technology (Danvers, MA) | (1:100) → fluor-DαRb | Sus cells, HBCs, GBCs. Same pattern as Gt α-Sox2 |
| Rb α-Sox9 | Millipore (Billerica, MA) | (1:500) → fluor-DαRb | Duct/Gland, Microvillar cells |
| Mo α-TuJ1 | Covance (Princeton, NJ) | (1:100) → fluor-DαMo | Neuron-specific tubulin |

Image processing and quantification. Stained sections were imaged on a Zeiss 510 Confocal microscope in multi-tracking mode or on a Nikon 800E epifluorescent microscope with a Spot RT2 digital camera. Image preparation, assembly and analysis were performed in Photoshop CS2. In the vast majority of photos, only balance, contrast and evenness of the illumination were altered. In cases where tyramide signal amplification was used to visualize bound antibody (Ascl1 and Hes1 staining), a median noise filter of 2 pixels or less was applied to images. This filter reduces nonspecific background speckling smaller than the filter setting and does not alter those features (nuclear and cytoplasmic) specific to the antibody staining. When necessary, low magnification images were taken with the Spot RT2 camera and assembled to encompass the entire tissue. The staining was highlighted using standard Photoshop tools.

Cell types were counted by direct observation with the epifluorescent microscope. A low magnification image was used to measure the length of OE counted. Three animals (at least 3 sections/animal) were counted per time point examined, and the data were analyzed by 2-way ANOVA using Graphpad Prism software. Mean values and standard error of the mean (s.e.m.) are reported.

EdU administration and processing. 80 mg/g EdU (Invitrogen) was administered by subcutaneous injection to animals or pregnant dams. Two hours after injection tissue was processed as above. For visualization of EdU incorporation, sections were permeabilized with 0.5% Triton X-100 in PBS, and treated with azide-594 containing Click-iT reaction cocktail (Invitrogen) for 30 minutes. After 3 washes in 3% BSA in PBS, sections were steamed and stained for p63 as above.

Electron Microscopy. The heads from P0 p63+/+ and p63−/− pups were immersion-fixed overnight in EM fix (4% PFA+3% gluteraldehyde in 0.1 M cacodylate buffer, pH 7.3). The olfactory tissue was then sectioned at 1 mm using a vibratome (Leica) and collected in cacodylate buffer. Sections were processed according to previously published protocols (Holbrook et al., 1995, Kubilus and Linsenmayer, 2010) and viewed on a Philips CM-10 transmission-electron microscope at 80 kV.

MeBr lesion. Twelve-week old F1 (C57×129) male mice were exposed to 180 ppm MeBr gas in pure air for 8 hours (Chen et al., 2004). SD Rats at 300 grams body weight were exposed to 330 ppm MeBr gas in pure air for 6 hours (Schwob et al., 1995).

References Example 2

Candi E, Dinsdale D, Rufini A, Salomoni P, Knight R A, Mueller M, Krammer P H, Melino G (2007) TAp63 and DeltaNp63 in cancer and epidermal development. Cell Cycle 6:274-285.

Candi E, Rufini A, Terrinoni A, Dinsdale D, Ranalli M, Paradisi A, De Laurenzi V, Spagnoli L G, Catani M V, Ramadan S, Knight R A, Melino G (2006) Differential roles of p63 isoforms in epidermal development: selective genetic complementation in p63 null mice. Cell Death Differ 13:1037-1047.

Carlen M, Meletis K, Goritz C, Darsalia V, Evergren E, Tanigaki K, Amendola M, Barnabe-Heider F, Yeung M S, Naldini L, Honjo T, Kokaia Z, Shupliakov O, Cassidy R M, Lindvall O, Frisen J (2009) Forebrain ependymal cells are Notch-dependent and generate neuroblasts and astrocytes after stroke. Nat Neurosci 12:259-267.

Carroll D K, Carroll J S, Leong C O, Cheng F, Brown M, Mills A A, Brugge J S, Ellisen L W (2006) p63 regulates an adhesion programme and cell survival in epithelial cells. Nat Cell Biol 8:551-561.

Carter L A, MacDonald J L, Roskams A J (2004) Olfactory horizontal basal cells demonstrate a conserved multipotent progenitor phenotype. J Neurosci 24:5670-5683.

Cau E, Casarosa S, Guillemot F (2002) Mash1 and Ngn1 control distinct steps of determination and differentiation in the olfactory sensory neuron lineage. Development 129:1871-1880.

Cau E, Gradwohl G, Casarosa S, Kageyama R, Guillemot F (2000) Hes genes regulate sequential stages of neurogenesis in the olfactory epithelium. Development 127:2323-2332.

Chen X, Fang H, Schwob J E (2004) Multipotency of purified, transplanted globose basal cells in olfactory epithelium. J Comp Neurol 469:457-474.

Crum C P, McKeon F D (2010) p63 in epithelial survival, germ cell surveillance, and neoplasia. Annu Rev Pathol 5:349-371.

Delorme B, Nivet E, Gaillard J, Haupl T, Ringe J, Deveze A, Magnan J, Sohier J, Khrestchatisky M, Roman F S, Charbord P, Sensebe L, Layrolle P, Feron F (2010) The human nose harbors a niche of olfactory ectomesenchymal stem cells displaying neurogenic and osteogenic properties. Stem Cells Dev 19:853-866.

Ghioni P, Bolognese F, Duijf P H, Van Bokhoven H, Mantovani R, Guerrini L (2002) Complex transcriptional effects of p63 isoforms: identification of novel activation and repression domains. Mol Cell Biol 22:8659-8668.

Goldstein B J, Fang H, Youngentob S L, Schwob J E (1998) Transplantation of multipotent progenitors from the adult olfactory epithelium. Neuroreport 9:1611-1617.

Graziadei P P, Graziadei G A (1979) Neurogenesis and neuron regeneration in the olfactory system of mammals. I. Morphological aspects of differentiation and structural organization of the olfactory sensory neurons. J Neurocytol 8:1-18.

Guo Z, Packard A, Krolewski R C, Harris M T, Manglapus G L, Schwob J E (2010) Expression of Pax6 and Sox2 in adult olfactory epithelium. The Journal of Comparative Neurology 9999:NA.

Holbrook E H, Leopold D A, Schwob J E (2005) Abnormalities of axon growth in human olfactory mucosa. Laryngoscope 115:2144-2154.

Holbrook E H, Szumowski K E, Schwob J E (1995) An immunochemical, ultrastructural, and developmental characterization of the horizontal basal cells of rat olfactory epithelium. J Comp Neurol 363:129-146.

Huard J M, Youngentob S L, Goldstein B J, Luskin M B, Schwob J E (1998) Adult olfactory epithelium contains multipotent progenitors that give rise to neurons and non-neural cells. J Comp Neurol 400:469-486.

Ito M, Yang Z, Andl T, Cui C, Kim N, Millar S E, Cotsarelis G (2007) Wnt-dependent de novo hair follicle regeneration in adult mouse skin after wounding. Nature 447:316-320.

Ito T, Udaka N, Yazawa T, Okudela K, Hayashi H, Sudo T, Guillemot F, Kageyama R, Kitamura H (2000) Basic helix-loop-helix transcription factors regulate the neuroendocrine differentiation of fetal mouse pulmonary epithelium. Development 127:3913-3921.

Iwai N, Zhou Z, Roop D R, Behringer R R. (2008) Horizontal basal cells are multipotent progenitors in normal and injured adult olfactory epithelium. Stem Cells. 26:1298-306.

Jacobs W B, Govoni G, Ho D, Atwal J K, Barnabe-Heider F, Keyes W M, Mills A A, Miller F D, Kaplan D R (2005) p63 is an essential proapoptotic protein during neural development. Neuron 48:743-756.

Jang W, Youngentob S L, Schwob J E (2003) Globose basal cells are required for reconstitution of olfactory epithelium after methyl bromide lesion. J Comp Neurol 460:123-140.

Keyes W M, Pecoraro M, Aranda V, Vernersson-Lindahl E, Li W, Vogel H, Guo X, Garcia E L, Michurina T V, Enikolopov G, Muthuswamy S K, Mills A A (2011) DeltaNp63alpha is an oncogene that targets chromatin remodeler Lsh to drive skin stem cell proliferation and tumorigenesis. Cell Stem Cell 8:164-176.

Kikuchi T, Ichimiya S, Kojima T, Crisa L, Koshiba S, Tonooka A, Kondo N, Van Der Saag P T, Yokoyama S, Sato N (2004) Expression profiles and functional implications of p53-like transcription factors in thymic epithelial cell subtypes. Int Immunol 16:831-841.

Koster M I, Dai D, Marinari B, Sano Y, Costanzo A, Karin M, Roop D R (2007) p63 induces key target genes required for epidermal morphogenesis. Proc Natl Acad Sci USA 104:3255-3260.

Kubilus J K, Linsenmayer T F (2010) Developmental corneal innervation: interactions between nerves and specialized apical corneal epithelial cells. Invest Ophthalmol V is Sci 51:782-789.

Largent B L, Sosnowski R G, Reed R R (1993) Directed expression of an oncogene to the olfactory neuronal lineage in transgenic mice. J Neurosci 13:300-312.

Laurikkala J, Mikkola M L, James M, Tummers M, Mills A A, Thesleff I (2006) p63 regulates multiple signalling pathways required for ectodermal organogenesis and differentiation. Development 133:1553-1563.

Lena A M, Shalom-Feuerstein R, Rivetti di Val Cervo P, Aberdam D, Knight R A, Melino G, Candi E (2008) miR-203 represses 'stemness' by repressing DeltaNp63. Cell Death Differ 15:1187-1195.

Leung C T, Coulombe P A, Reed R R (2007) Contribution of olfactory neural stem cells to tissue maintenance and regeneration. Nat Neurosci 10:720-726.

Manglapus G L, Youngentob S L, Schwob J E (2004) Expression patterns of basic helix-loop-helix transcription factors define subsets of olfactory progenitor cells. J Comp Neurol 479:216-233.

McKeon F, Melino G (2007) Fog of war: the emerging p53 family. Cell Cycle 6:229-232.

Mills A A, Zheng B, Wang X J, Vogel H, Roop D R, Bradley A (1999) p63 is a p53 homologue required for limb and epidermal morphogenesis. Nature 398:708-713.

Nakamuta N, Kobayashi S (2007) Expression of p63 in the mouse ovary. J Reprod Dev 53:691-697.

Nguyen B C, Lefort K, Mandinova A, Antonini D, Devgan V, Della Gatta G, Koster M I, Zhang Z, Wang J, Tommasi di Vignano A, Kitajewski J, Chiorino G, Roop D R, Missero C, Dotto G P (2006) Cross-regulation between Notch and p63 in keratinocyte commitment to differentiation. Genes Dev 20:1028-1042.

Noszczyk B H, Majewski S T (2001) p63 expression during normal cutaneous wound healing in humans. Plast Reconstr Surg 108:1242-1247; discussion 1248-1250.

Romano R A, Birkaya B, Sinha S (2006) Defining the regulatory elements in the proximal promoter of DeltaNp63 in keratinocytes: Potential roles for Sp1/Sp3, NF-Y, and p63. J Invest Dermatol 126:1469-1479.

Romano R A, Ortt K, Birkaya B, Smalley K, Sinha S (2009) An active role of the DeltaN isoform of p63 in regulating basal keratin genes K5 and K14 and directing epidermal cell fate. PLoS One 4:e5623.

Romano R A, Smalley K, Liu S, Sinha S (2010) Abnormal hair follicle development and altered cell fate of follicular keratinocytes in transgenic mice expressing DeltaNp63alpha. Development 137:1431-1439.

Schwob J E, Youngentob S L, Mezza R C (1995) Reconstitution of the rat olfactory epithelium after methyl bromide-induced lesion. J Comp Neurol 359:15-37.

Su X, Paris M, Gi Y J, Tsai K Y, Cho M S, Lin Y L, Biernaskie J A, Sinha S, Prives C, Pevny L H, Miller F D, Flores E R (2009) TAp63 prevents premature aging by promoting adult stem cell maintenance. Cell Stem Cell 5:64-75.

Suh E K, Yang A, Kettenbach A, Bamberger C, Michaelis A H, Zhu Z, Elvin J A, Bronson R T, Crum C P, McKeon F (2006) p63 protects the female germ line during meiotic arrest. Nature 444:624-628.

Suzuki Y, Takeda M (1991) Keratins in the developing olfactory epithelia. Brain Res Dev Brain Res 59:171-178.

Thepot A, Hautefeuille A, Cros M P, Abedi-Ardekani B, Petre A, Damour O, Krutovskikh V, Hainaut P (2010) Intraepithelial p63-dependent expression of distinct components of cell adhesion complexes in normal esophageal mucosa and squamous cell carcinoma. Int J Cancer.

Tome M, Lindsay S L, Riddell J S, Barnett S C (2009) Identification of nonepithelial multipotent cells in the embryonic olfactory mucosa. Stem Cells 27:2196-2208.

Wildner H, Muller T, Cho S H, Brohl D, Cepko C L, Guillemot F, Birchmeier C (2006) dILA neurons in the dorsal spinal cord are the product of terminal and non-terminal asymmetric progenitor cell divisions, and require Mash1 for their development. Development 133:2105-2113.

Yalcin-Ozuysal O, Fiche M, Guitierrez M, Wagner K U, Raffoul W, Brisken C (2010) Antagonistic roles of Notch and p63 in controlling mammary epithelial cell fates. Cell Death Differ.

Yang A, Kaghad M, Wang Y, Gillett E, Fleming M D, Dotsch V, Andrews N C, Caput D, McKeon F (1998) p63, a p53 homolog at 3q27-29, encodes multiple products with trans-activating, death-inducing, and dominant-negative activities. Mol Cell 2:305-316.

Yang A, Schweitzer R, Sun D, Kaghad M, Walker N, Bronson R T, Tabin C, Sharpe A, Caput D, Crum C, McKeon F (1999) p63 is essential for regenerative proliferation in limb, craniofacial and epithelial development. Nature 398:714-718.

Yang A, Zhu Z, Kapranov P, McKeon F, Church G M, Gingeras T R, Struhl K (2006) Relationships between p63 binding, DNA sequence, transcription activity, and biological function in human cells. Mol Cell 24:593-602.

Yi R, Poy MN, Stoffel M, Fuchs E (2008) A skin microRNA promotes differentiation by repressing 'stemness'. Nature 452:225-229.

Example 3

The following data substantiate the role of p63 as a linchpin in the maintenance and activation of HBCs, and further support the rationale for targeting p63 to achieve HBC activation in a clinical population.

Figure 11A:
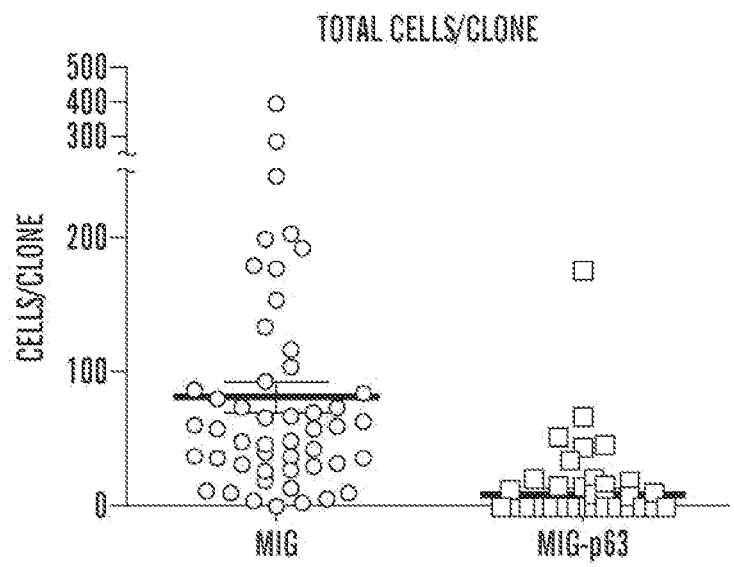
FIG. 11A-FIG. 11B are graphs of the clone composition of cells transduced with the empty vector control (MIG) or the p63 encoding construct (MIG-p63).
Figure 11B:
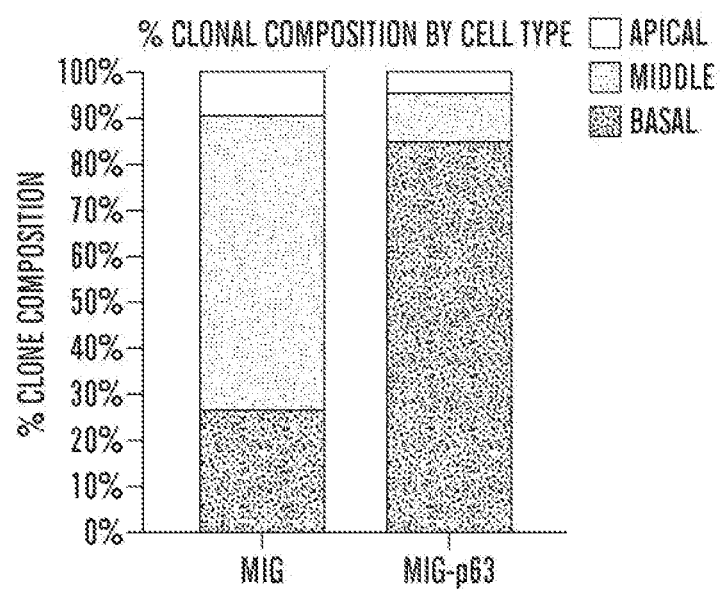
Figure 12A:
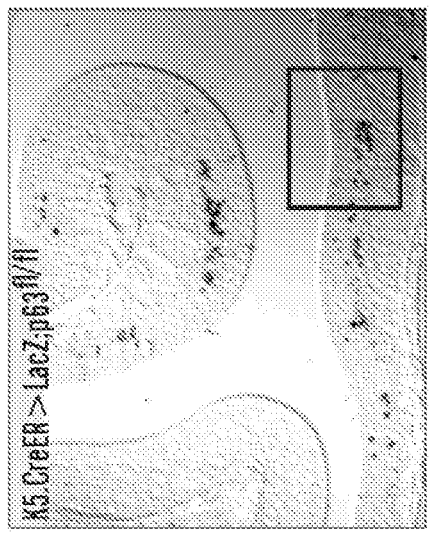
FIG. 12A-FIG. 12D depict microscopy images of the results of conditional p63 knock-out in normal epithelium. HBC cells and progeny thereof have lacZ activity and thus stain blue (shown as dark spots in these photographs).
Figure 12C:
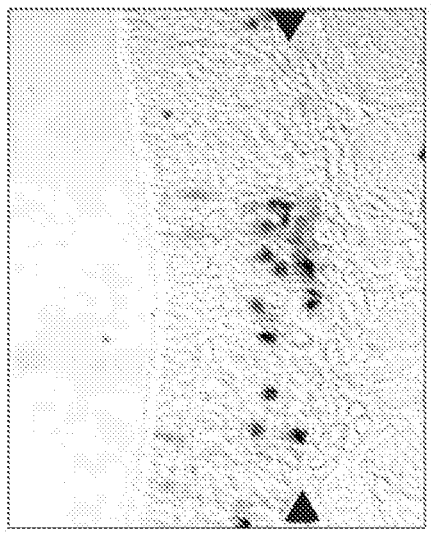
Figure 12B:
Figure 12D:
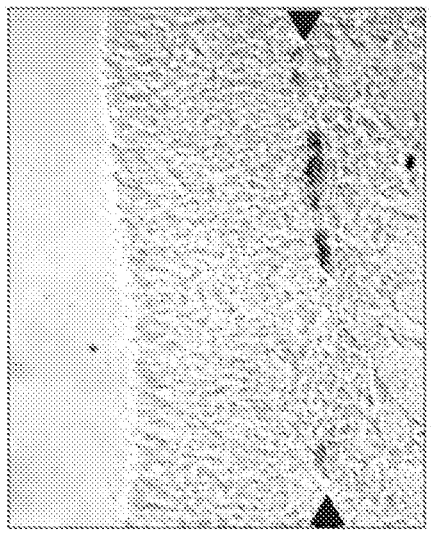

In order to dissect further the specific requirement for p63 in HBC maintenance and activation, we have performed two complementary manipulations. First, we over-expressed αNp63Δ in the regenerating epithelium using retroviral infection. In this paradigm proliferating progenitor cells scattered across the olfactory epithelium were infected with RVV, at a frequency that allowed one to conclude that each spatially isolated cluster of labeled cells arose as a clone from a single infected progenitor cell. After a survival period of two weeks the clones were analyzed for size (cells/clone) and composition (apico-basal distribution, and marker-defined cellular identity). We found that the MIG-p63-infected progenitor cells gave rise to significantly smaller clones compared to the empty vector MIG-infected progenitor cells as determined by immunohistochemistry performed to detect p63, PGP9.5, and CK5 expression (FIG. 11A-B). These clones consisted predominantly of K14(+) and K5(+) basal cells, and did not stain for the neural markers Tuj1 or PGP9.5 even in the few non-basally positioned cells. This was in stark contrast to the MIG-derived clones, which generally spanned the apico-basal axis and contained basal cells, neurons, and sustentacular cells. These data indicate that p63 expression prevents activation of HBCs to multipotency. Since most of the dividing infected cells at 1 day after lesion corresponded to GBCs, these data also suggest that p63 expression is sufficient to drive HBC differentiation, consistent with our observations in the embryo (Packard, Schnittke, et al., 2011). HBC differentiation was detected following transduction with the p63-encoding retroviral construct.

To complement the above overexpression data, we bred a conditional p63 knock-out mouse line (cKO). We utilized the K5.CreER line previously used in the OE, to achieve tamoxifen-inducible deletion of a floxed allele of p63 specifically in the K5(+) HBCs. We administered tamoxifen at 7 weeks of age, and analyzed the OE1 week later in the cKO animals vs. the K5.CreER×R26R control line (FIGS. 12A-12D).

Immunohistochemistry was performed on the cells derived from HBCs activated in normal epithelium following elimination of p63 by recombination to visualize lacZ expression, PGP9.5 expression, CK14 expression. Descendants of activated HBCs include PGP9.5(+) neurons, and GBCs located below the neuron layer. Descendants of activated HBCs also included rare HBCs. Consistent with past reports, we found that HBC derived cells in the control mice (in which p63 remains intact and functional) remained as HBCs one week after recombination. However, in cKO animals (in which p63 has been eliminated from the HBCs), the HBCs in which recombination occurred gave rise predominantly to neurons and, to a lesser extent, to duct/gland cells and sustentacular cells. Also labeled among the cKO progeny, were rare K5(+) HBCs. We have yet to determine if these labeled HBCs still have residual p63 expression and might be the product of incomplete recombination of both p63 floxed alleles. However, even if mature HBCs do persist in the p63 cKO animals, it is clear that there's a dramatic increase in the ability of HBCs to differentiate into neurons and other OE cellular components. These data indicate that loss of p63 is sufficient to allow for HBC activation and differentiation.

The experiments described here demonstrate the linch-pin role played by p63 in the establishment and continued dormancy of the HBCs of the olfactory epithelium. Furthermore, the experiment utilizing cKO of p63 in the context of the unlesioned olfactory epithelium provides proof-of-principle that elimination of p63 is sufficient in and of itself to produce the activation of HBCs to multipotency. Thus, down-regulation of p63 by miRNAs or siRNAs delivered to HBCs, when suppression is achieved, will lead to the formation of neurons and offers the opportunity to ameliorate the neurogenic failure observed in aging humans.

Materials and Methods

Figure 13A:
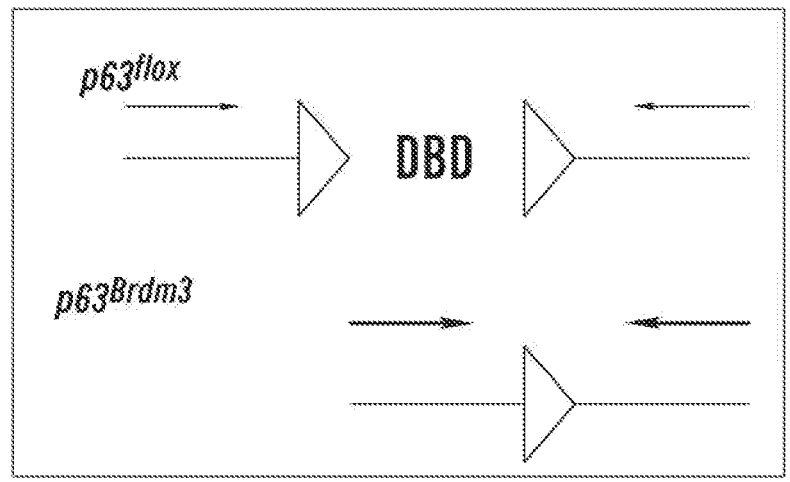
FIG. 13A-FIG. 13B depict diagrams of the experimental strategy.
Figure 13B:
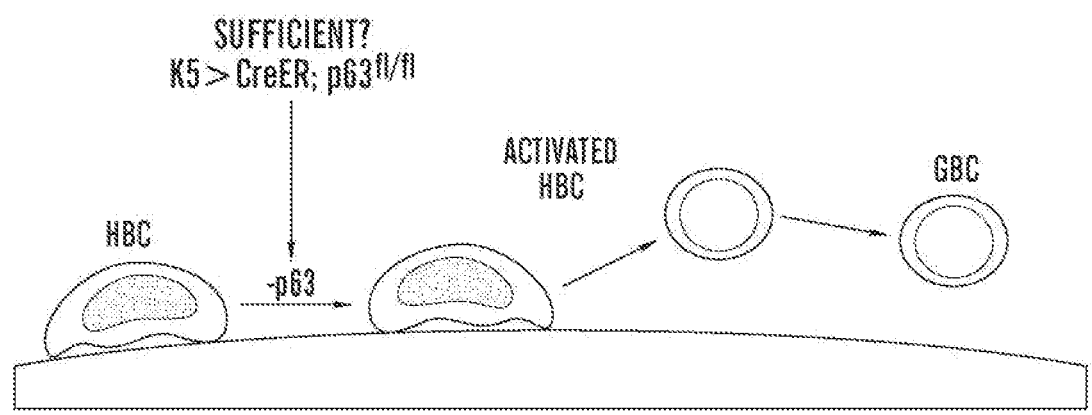

Animal Strains. C57/B6 mice were mated to 129S1/Sv1MJ (Jackson) to produce the F1 progeny used in MeBr lesion experiments. Generation of the K5-CreER$^{TM}$, p63$^{fl}$, and Rosa26(stop)lacZ mice has been described previously. To generate p63 conditional knockout (cKO) animals, two parent lines were established: (1) fl(p63 DBD)×Rosa26(stop) lacZ (abbreviated fl(p63)×R26R) to generate the double homozygote parent line fl(p63)/fl(p63); R26R/R26R and (2) K5-CreER; R26R×fl(p63); R26R to generate the triple transgenic parent line K5-CreER; fl(p63)/+; R26R. These two parent strains were then mated to each other (fl(p63)/fl(p63); R26R/R26R×K5-CreER; fl(p63)/+; R26R) to generate the cKO animals (K5-CreER; fl(p63)/fl(p63); R26R) and their control littermates (K5-CreER; fl(p63)/+; R26R) (FIGS. 13A-B).

Tamoxifen Administration. 4-hydroxytamoxifen (4-OHT) (Sigma) was diluted to a stock concentration of 40 mg/ml in DMSO. Prior to injection the stock solution was diluted to 5 mg/ml in corn oil. 0.5 mg of 5 mg/ml 4-OHT were injected IP.

Figure 14:
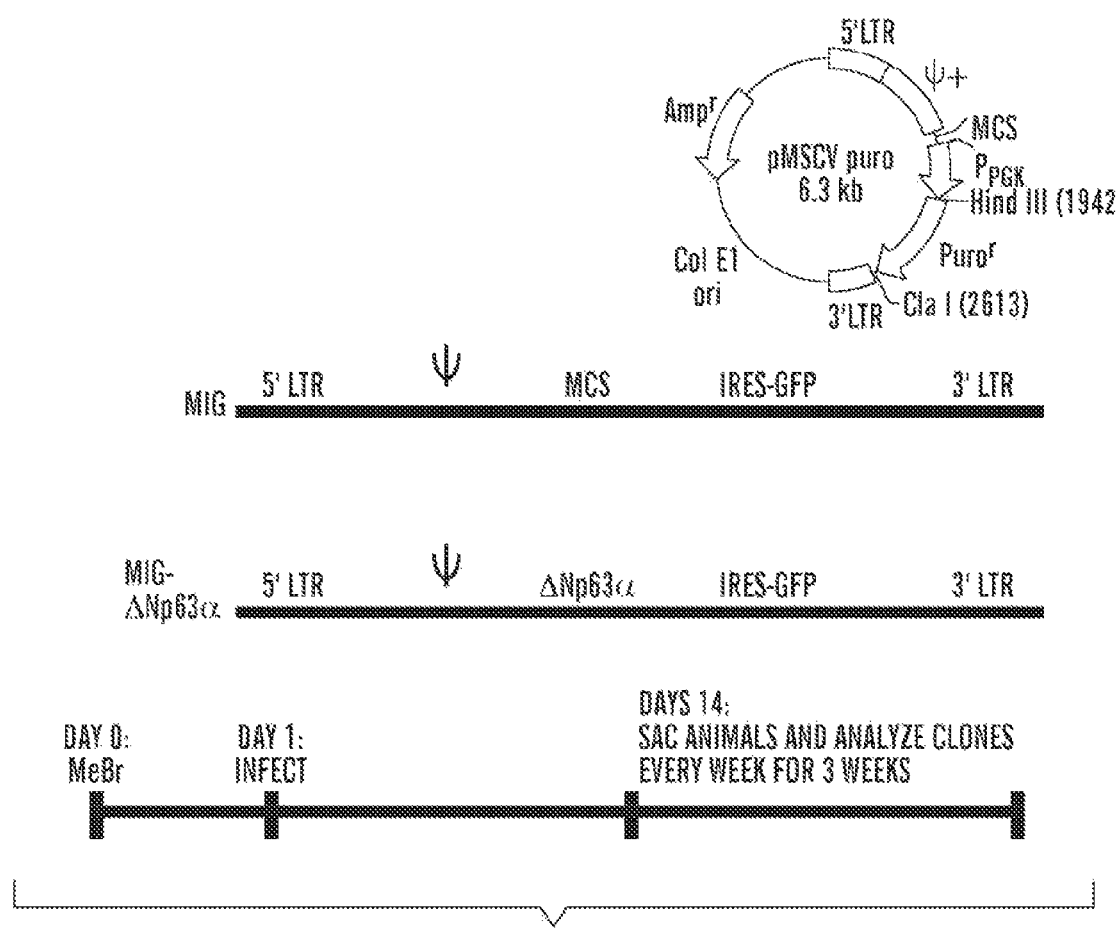
FIG. 14 depicts a schematic of the experiments involving p63 overexpression. The top portion of the Figure presents the retroviral constructs to be used. MIG is the empty vector control, MIG-ΔNp63α encodes the ΔNp63α version of the p63 protein. The bottom of FIG. 14 presents the timeline of the experiments in Example 3.
Figure 15:
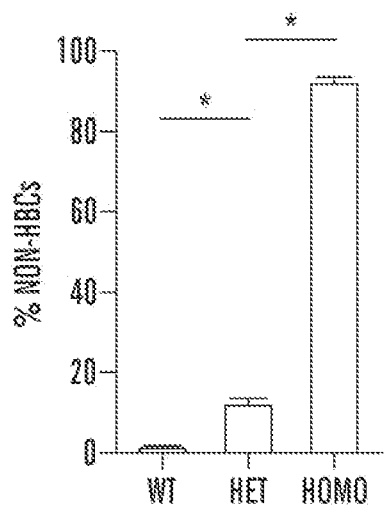
FIG. 15 is a bar graph of data indicating the percent of non-HBC progeny when zero (WT), one (HET), or both (HOMO) copies of the p63 gene are clipped out of the genome. Note that the elimination of one copy provides a limited degree of activation, whereas robust activation results from elimination of both copies.
Figure 16:
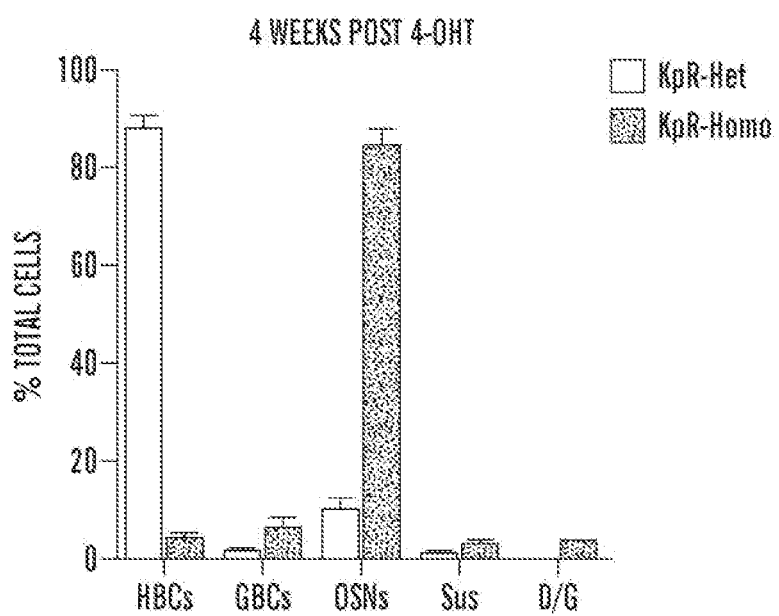
FIG. 16 is a bar graph of quantitative data of the number of specific types of cells that were identified as arising in mice as progeny of horizontal basal cells (HBCs) from which had p63 knock-outs (heterozygous or homozygous) resulting from genetic recombination. Amongst the cell types that arose were olfactory neurons (OSNs), globose basal cells (GBCs), duct and gland cells (found in the deeper tissue), and microvillar cell. The compiled data are summarized and compared between one copy of p63 (KpR-Het) and no copies of p63 (KpR-Homo).

Retroviral Constructs and Generation. The Murine Stem Cell Virus (MSCV.puro) retroviral backbone (Clontech) was used to clone the MSCV.IRES-GFP (MIG) and MSCV.ΔNp63α-IRES-GFP (MIG-p63) constructs used here (FIG. 14).

To generate concentrated retroviral supernatant, HEK293T cells were co-transfected with plasmids bearing the corresponding retroviral vector (RVV), and the pCL-ECO ecotropic packaging vector using a conventional calcium phosphate precipitation protocol. 48 hours after transfection the supernatant was collected and concentrated using the RetroConcentin reagent (System Biosciences).

Retroviral infection. One day after MeBr lesion C57.129 F1 host mice were anaesthetized with an IP injection of triple cocktail of ketamine (37.5 mg/kg), xylazine (7.5 mg/kg), and acepromazine (1.25 mg/kg). The neck was sterilized with iodine and ethanol and a tracheotomy was performed inferior to the thyroid gland. Polyethylene PE-60 tubing was inserted into the oral cavity to lift the soft pallet, close the nasopharyngeal passage, and limit viral delivery to the nasal cavity. PE-10 tubing was then passed 7 mm into one nostril and secured using superglue. 70 μl of concentrated viral supernatant was infused through the PE-10 tubing. Mice were left at a 45 degree angle to allow drainage of virus into the lateral turbinates, alternating sides every 45 minutes for a total of 3.5 hours.

Example 4

Three new lines of evidence indicate that p63 is the appropriate factor to target.

First, it has been shown that genetic "knock-out" of p63 in mice activates the dormant horizontal basal cell (HBC) stem cells to generate primarily olfactory neurons in an epithelium that is otherwise unmanipulated and uninjured (FIG. 1A, 12, 15 and 16). In FIGS. 12A and B, the progeny of HBCs were identified without manipulating expression of p63. Note that all of the progeny (identified by labeling with x-gal (shown as dark spots) remain as HBCs. In FIGS. 12C and D, the progeny of HBCs were identified following CreER-mediated genetic elimination of p63 by conditional recombination in a subset of HBCs. Note that neurons were generated, which could be identified by their elaboration of a dendrite extending to the surface and their location in the middle zone of the epithelium. These observations suggest that p63 is the key switch in regulating the behavior of the HBC reserve stem cells.

Figure 17A:
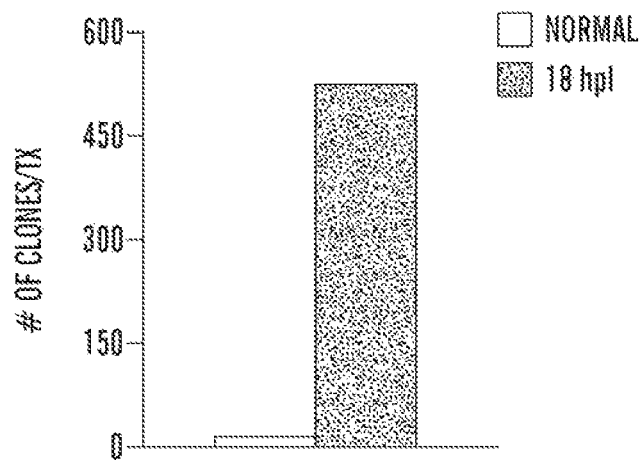
FIG. 17A-FIG. 17B are bar graphs of results from experiments that show HBCs HBCs transplanted from normal OE (left bars), where p63 expression is high, engraft poorly (FIG. 17A) and generate few cells (FIG. 17B). In contrast, HBCs transplanted 18 hours after injury to the OE by exposure to the olfactotoxic gas methyl bromide (right bars), when p63 expression is declining, engraft readily (FIG. 17A) and give rise to very large clusters of cells of all epithelial types (FIG. 17B).
Figure 17B:
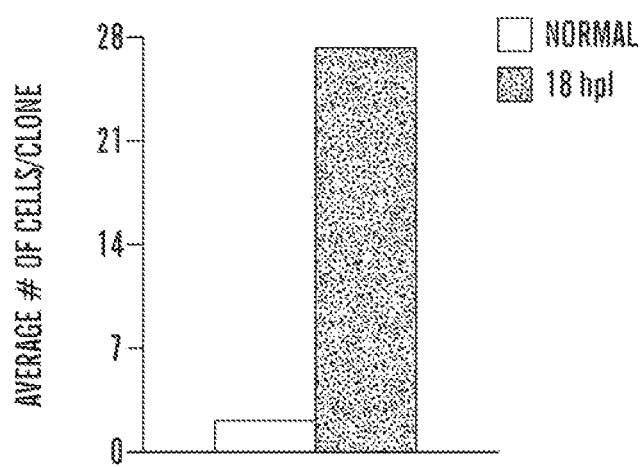

Second, it has been demonstrated that downregulation of p63 is not only sufficient, but necessary for activation. Using a transplantation assay to challenge the progenitor cell capacity of HBCs derived from mouse olfactory epithelium, it has been shown that, in the absence of activation in situ prior to transplantation, HBCs will engraft only rarely and do not give rise to the replacement neurons that would be needed to repair the neurogenic exhaustion that accompanies sensory loss in the elderly. In contrast, HBCs isolated less than 24 hours after injury to the epithelium, at a time when p63 is being downregulated in response to injury-elicited signaling molecules, are capable of robust integration after transplantation and to the generation of all types of replacement cells needed (FIG. 17).

Figure 18A:
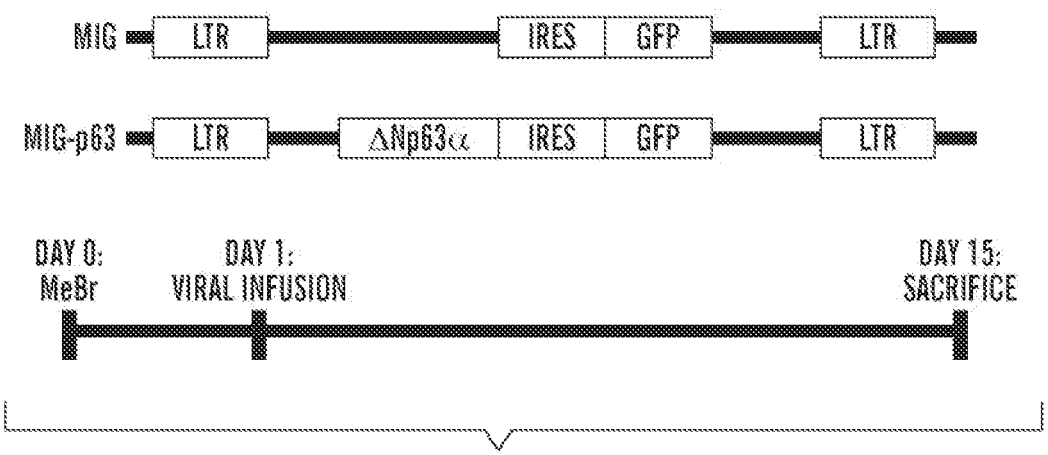
FIG. 18A-FIG. 18D is a collection of figures summarizing experimental results that indicate overexpression of p63 prevent activation in response to epithelial damage.
Figure 18B:
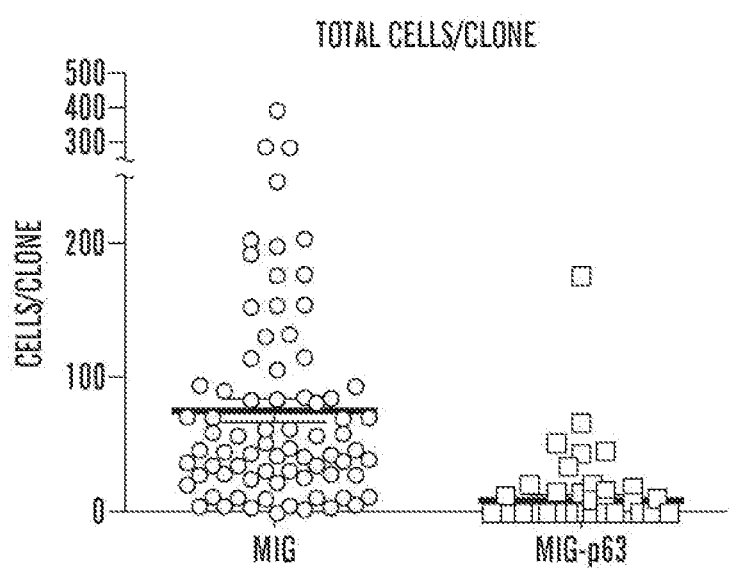
Figures 18C, 18D:
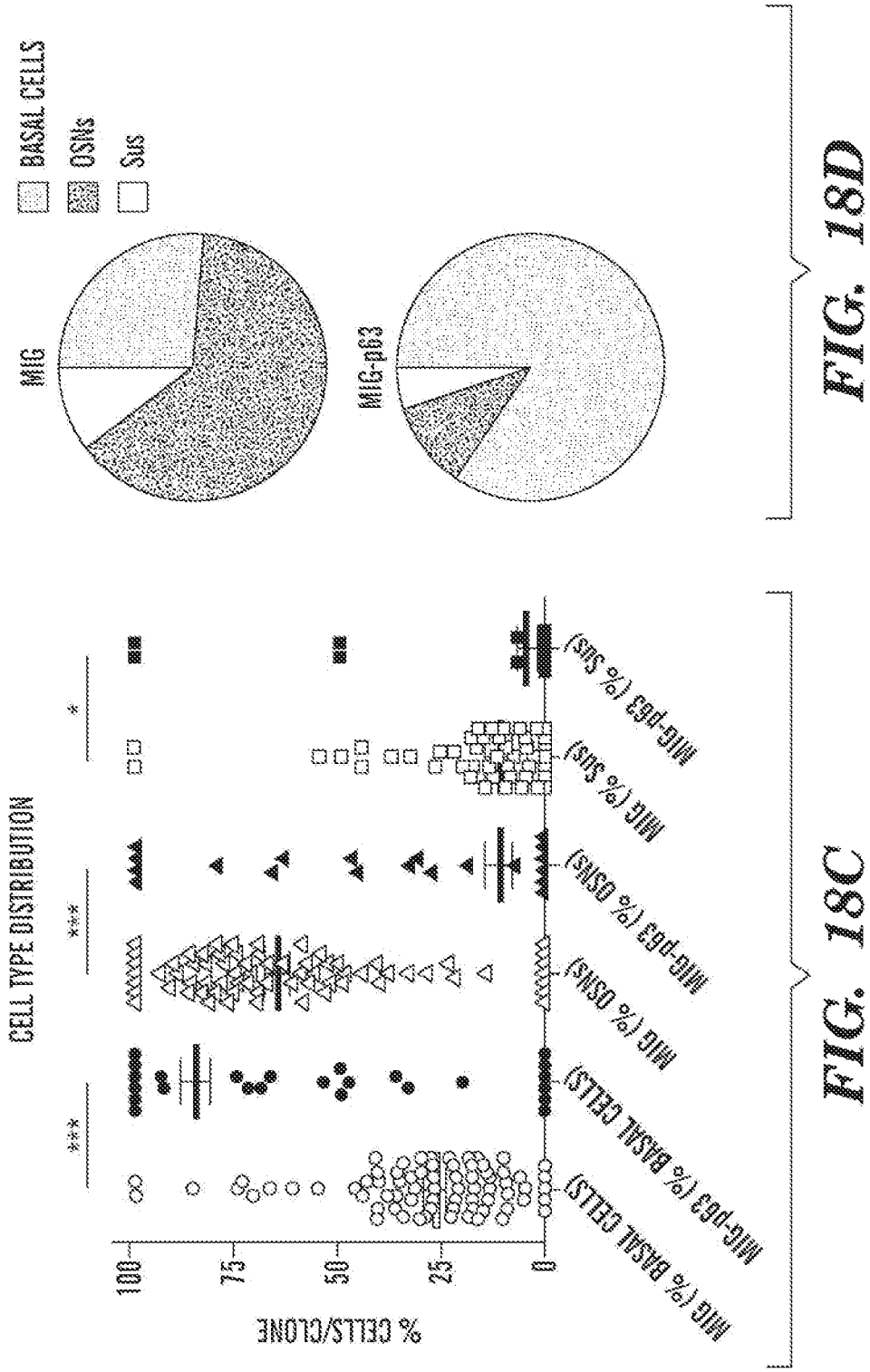

In contrast, if p63 expression is artificially maintained via transduction with a retrovirally-derived vector that encodes and drives constitutive expression of p63 then the HBCs do not activate and do not give rise to any other cell types whatsoever (FIG. 18). Thus, control of p63 expression is both necessary and sufficient to activate the dormant HBCs but is responsive to only a narrow range of signals, derived from the acutely injured tissue, and not replicated following transplantation to another animal.

Third, the expression of p63 in human olfactory epithelium acquired at autopsy in elderly individuals has been assayed. Human OE harvested at autopsy were assayed for various cellular markers. Area of neurogenic exhaustion in adjacent sections stained for neurons and other markers. OMP, which marks mature neurons, was almost completely absent, yet b4-tubulin, which marks respiratory epithelial cells (as visualized in respiratory epithelium in the same individual), was also absent, indicating that the apical cells remain sus cells and have not been replaced. Neuro-tubulin, which marks both mature and immature olfactory neurons, was also largely absent. A complete row of dormant, quiescent HBCs was marked by the expression of p63. In all sections examined, the nuclei were stained blue with the nuclear marker DAPI.

The results indicate that p63 expression is characteristic of HBCs in human tissue as well as rodent. Moreover, in olfactory epithelium where neurogenesis has become exhausted (as discussed above), the epithelium had not converted to respiratory epithelium, neurons were largely absent, the HBCs remained dormant, and they expressed p63. Thus, p63 is a target for therapeutic manipulation in patients suffering from hyposmia or anosmia due to aging.

Materials and Methods

Animals and procedures. K5.CreEr mice were provided by R. Reed and P. Chambon, p63fl/fl mice were provided by A. Mills, B6.129 F1 mice were bred at Tufts from C57.B6 and 129.SViMj mice, R26R(LacZ) and R26R(TdTomato)-Ai9 mice were purchased from Jackson labs.

Tamoxifen treatment was performed by intraperitoneal injection of 0.5 mg 4-hydroxytamoxifen or 300 mg/kg tamoxifen dissolved in corn oil.

Transplantation and retroviral infection assays were performed on anaesthetized B6.129 F1 male mice 24 hours after MeBr lesion. Briefly, the host mice were anaesthetized with a ketamine/xylazine/acepromazine cocktail and a tracheotomy was performed. The palate was elevated with PE120 tubing to confine the solution to the nasal cavity. Virus or donor cells were introduced into the nasal cavity through PE10 tubing and allowed to incubate within the cavity for 3 hours. During the incubation, mice were kept anaesthetized with ketamine/acepromazine injections PRN. After incubation, the solution was removed from the nasal cavity and the site of the tracheotomy was sutured. Mice remained under close (3x/day) post-operative observation and assessment.

Methyl bromide lesion was carried out by exposing mice to methyl bromide gas diluted in pure air within a sealed chamber. The concentration of MeBr was determined empirically for each given age and mouse strain and varied from 175-180 ppm.

All protocols governing the use of vertebrate animals were approved by the Committee for the Humane Use of Animals at Tufts University School of Medicine, where the animals were housed and experiments were conducted.

Tissue processing and staining. Mice were anaesthetized with an IP injection of triple cocktail of ketamine (37.5 mg/kg), xylazine (7.5 mg/kg), and acepromazine (1.25 mg/kg). Anaesthetized animals were transcardially flushed with PBS and perfused with 1% PLP. After dissection the tissue was post-fixed in 1% PLP under vacuum and decalcified in saturated EDTA overnight. All tissue was cryoprotected in 30% sucrose in PBS, embedded in OCT compound (Miles Inc., Elkhart, Ind.), and frozen in liquid nitrogen. 8 μm coronal sections were generated on a Leica cryostat, mounted on "Plus" slides (Fischer Scientific) and stored at −20° C. until needed.

Human autopsy tissue was obtained from NDR1 in formalin. Strips of olfactory mucosa, harvested from the lining of the nasal cavity below the cribriform plate were embedded in OCT<frozen and cryosectioned before immunostaining.

For immunostaining tissue sections were rinsed in PBS to remove OCT, puddled with citrate buffer, and steamed for 10 minutes in a commercial food steamer. Sections were blocked with 10% donkey serum/5% non-fat dry milk/4% BSA/0.1% TritonX-100 in PBS and incubated overnight in primary antibody. The following day the staining was visualized using fluorescently conjugated secondary antibodies or DAB chromagen development. Unless otherwise indicated, blue represents the nuclear counterstain DAPI.

X-gal staining was performed by incubating sections overnight in X-gal staining solution containing: 0.02% deoxycholic acid, 0.01% Nonidet P40, 20 mM K-ferrocyanide, 20 mM K-ferricyanide, 2 mM MgCl2, 1 mg/ml X-gal made up in PBS.

Quantification and Analysis. Quantification of clone size, clone composition, and cellular identity was performed from direct observation under a Nikon 800E epifluorescent microscope. The raw data were then analyzed using GraphPad Prism 5 software for statistical significance and graphical representation.

Retroviral Constructs. To generate retroviral vectors we modified MSCV.puro from Clontech. MSCV-IRES-GFP (MIG) was generated by replacing the PGK.puro selection cassette with an IRES-GFP cassette (using EcoRI and ClaI restriction sites). MIG-p63 was generated from this MIG backbone by cloning ΔNp63α into the BglII and XhoI restriction sites upstream of the IRES-GFP sequence. Full length ΔNp63α was provided in the pCMV-HA plasmid by S. Sinha.

What is claimed:

1. A method for activating a dormant horizontal basal cell (HBC) of the olfactory epithelium, or population thereof, to a state of multipotency comprising, reducing the level of ΔNp63 in the cell(s) by contacting the cell or population with an effective amount of an RNAi designed for inhibition of expression of ΔNp63, to thereby reduce the level of ΔNp63 in cell(s) to activate the cell(s) to a state of multipotency.

2. The method of claim 1, wherein the RNAi is a micro RNA.

3. The method of claim 2, wherein the microRNA is micro RNA 203.

4. The method of claim 1, wherein the cell(s) is in vivo, and contacting is by administering the RNAi in the form of a pharmaceutical composition to a subject to thereby contact the cell(s).

* * * * *